US008110361B2

(12) United States Patent
Laird et al.

(10) Patent No.: US 8,110,361 B2
(45) Date of Patent: Feb. 7, 2012

(54) DNA METHYLATION MARKERS ASSOCIATED WITH THE CPG ISLAND METHYLATOR PHENOTYPE (CIMP) IN HUMAN COLORECTAL CANCER

(75) Inventors: Peter W. Laird, South Pasadena, CA (US); Kimberly D. Siegmund, San Marino, CA (US); Mihaela Campan, Los Angeles, CA (US); Daniel J. Weisenberger, Playa del Rey, CA (US); Tiffany I. Long, Chino, CA (US)

(73) Assignee: University of Southern California USC Stevens Center for Innovation, Los Angeles, CA (US)

( * ) Notice: Subject to any disclaimer, the term of this patent is extended or adjusted under 35 U.S.C. 154(b) by 263 days.

(21) Appl. No.: 11/913,535

(22) PCT Filed: May 2, 2006

(86) PCT No.: PCT/US2006/017160
§ 371 (c)(1),
(2), (4) Date: Dec. 28, 2007

(87) PCT Pub. No.: WO2006/119434
PCT Pub. Date: Nov. 9, 2006

(65) Prior Publication Data
US 2009/0053706 A1 Feb. 26, 2009

Related U.S. Application Data

(60) Provisional application No. 60/677,181, filed on May 2, 2005.

(51) Int. Cl.
*C12Q 1/68* (2006.01)
(52) U.S. Cl. .................. 435/6.14; 435/6.11; 435/6.12
(58) Field of Classification Search .................. None
See application file for complete search history.

(56) References Cited

U.S. PATENT DOCUMENTS

| 5,565,552 | A | 10/1996 | Magda et al. |
| 5,567,810 | A | 10/1996 | Weis et al. |
| 5,574,142 | A | 11/1996 | Meyer, Jr. et al. |
| 5,585,481 | A | 12/1996 | Arnold, Jr. et al. |
| 5,587,371 | A | 12/1996 | Sessler et al. |
| 5,597,696 | A | 1/1997 | Linn et al. |
| 5,786,146 | A | 7/1998 | Herman et al. |
| 5,958,773 | A | 9/1999 | Monia et al. |
| 6,251,594 | B1 | 6/2001 | Gonzalgo et al. |
| 6,265,171 | B1 | 7/2001 | Herman et al. |
| 6,331,393 | B1 | 12/2001 | Laird et al. |
| 2003/0013091 | A1 | 1/2003 | Dimitrov |
| 2004/0265833 | A1* | 12/2004 | Lofton-Day et al. ........... 435/6 |

FOREIGN PATENT DOCUMENTS

| WO | WO 95/00669 | 1/1995 |
| WO | WO 95/15373 | 6/1995 |
| WO | WO 97/46705 | 12/1997 |
| WO | WO 99/28498 | 6/1999 |
| WO | WO 00/26401 | 5/2000 |
| WO | WO 02/077272 | 10/2002 |
| WO | WO 03/052135 | 6/2003 |
| WO | WO 2005/038051 | 4/2005 |

OTHER PUBLICATIONS

U.S. Appl. No. 60/677,181, filed May 2, 2005, Laird et al.
Belyavsky et al., "PCR-based cDNA library construction: general cDNA libraries at the level of a few cells," Nucleic Acids Research, 1989, pp. 2919-2983, vol. 17.
Database, "Homo sapiens cDNA clone Image: 6014407 5', mRNA sequence," XP002410381, retrieved from EMBL, Database accession No. bq422178, May 28, 2002 (1 page).
Eads et al., "CpG Island Hypermethylation in Human Colorectal Tumors Is Not Associated with DNA Methyltransferase Overexpression," Cancer Research, May 15, 1999, pp. 2302-2306, vol. 59.
Feil et al., "Methylation analysis on individual chromosomes: improved protocol for bisulphite genomic sequencing," Nucleic Acids Research, 1994, pp. 695-696, vol. 22.
Frommer et al., "A genomic sequencing protocol that yields a positive display of 5-methylcytosine residues in individual DNA strands," The Proceedings of the National Academy of Sciences, Mar. 1992, pp. 1827-1831, vol. 89.
Galfre et al., "Preparation of Monoclonal Antibodies: Strategies and Procedures," Methods in Enzymology, 1981, pp. 3-46, vol. 73.
Gonzalgo et al., "Identification and Characterization of Differentially Methylated Regions of Genomic DNA by Methylation-sensitive Arbitrarily Primed PCR," Cancer Research, Feb. 15, 1997, pp. 594-599, vol. 57.
Gonzalgo et al., Rapid quantitation of methylation differences at specific sites using methylation-sensitive single nucleotide primer extension (Ms-SNuPE), Nucleic Acids Research, 1997, pp. 2529-2531, vol. 25.
Grigg et al., "Sequencing 5-Methylcytosine Residues in Genomic DNA," BioEssays, Jun. 1994, pp. 431-436, vol. 16.

(Continued)

*Primary Examiner* — James Martinell
(74) *Attorney, Agent, or Firm* — Barry L. Davison; Davis Wright Tremaine LLP

(57) ABSTRACT

Particular aspects confirm the existence of a CpG island methylator phenotype (CIMP) in colorectal cancer, and provide novel validated DNA methylation markers associated with CIMP. Additional aspects provide novel methods and compositions for: determining CIMP status in colorectal cancers, determining the relationship between CIMP status and other molecular features of the cancers (e.g., BRAF mutation, KRAS mutation and MSI status); determining the relationship between CIMP status and other variables (e.g., age, sex, tumor location, family history, race, country of origin, tumor characteristics (including, tumor type, tumor grade, invasive margin characteristics, lymphocyte infiltration characteristics, direct spread, lymph node spread, venous spread and type of residual adjacent polyp, if present)); and determining, between subgroups defined by CIMP status and BRAF mutations, effects of selected risk factors (e.g., body mass index, smoking history, alcohol intake, dietary folate intake, folate metabolic enzyme polymorphisms and history of hormonal use).

29 Claims, 6 Drawing Sheets

OTHER PUBLICATIONS

Gut et al, "DNA and Matrix Assisted Laser Desorption Ionization Mass Spectrometry," Molecular Biology: Current Innovations and Future Trends, 1995, pp. 147-157, Horizon Scientific Press, Wymondham, United Kingdom.

Gut et al., "A procedure for selection DNA alkylation and detection by mass spectrometry," Nucleic Acids Research, 1995, pp. 1367-1373, vol. 23.

Heid et al., "Real Time Quantitative PCR," Genome Research, 1996, pp. 986-994, vol. 6.

Herman et al., "Methylation-specific PCR: A novel PCR assay for methylation status of CpG islands," The Proceedings of the National Academy of Sciences, Sep. 1996, pp. 9821-9826, vol. 93.

Issa, "CpG island methylator phenotype in cancer," Nature, 2004, pp. 988-993, vol. 4.

Karas et al., "Laser Desorption Ionization of Proteins with Molecular Masses Exceeding 10 000 Daltons," Analytical Chemistry, Oct. 15, 1988, pp. 2299-2301, vol. 60.

Koehler et al., "Continuous cultures of fused cells secreting antibody of predefined specificity," Nature, Aug. 7, 1975, pp. 495-496, vol. 256.

Krug et al., "First-Strand cDNA Synthesis Primed with Oligo(dT)," Methods in Enzymology, 1987, pp. 316-325, vol. 152.

Martin et al., "Genomic sequencing indicates a correlation between DNA hypomethylation in the 5' region of the pS2 gene and its expression in human breast cancer cell lines," Gene, 1995, pp. 261-265, vol. 157.

Ogino et al., "CpG island methylator phenotype (CIMP) of colorectal cancer is best characterized by quantitative DNA methylation analysis and prospective cohort studies," Gut, 2006, e-published on Jan. 11, 2006 (19 pages).

Ogino et al., "CpG island methylator phenotype (CIMP) of colorectal cancer is best characterized by quantitative DNA methylation analysis and prospective cohort studies," Gut, 2006, pp. 1000-1006, vol. 55.

Olek et al., "A modified and improved method for bisulphite based cytosine methylation analysis," Nucleic Acids Research, 1996, pp. 5064-5066, vol. 24.

Olek et al., "The pre-implantation ontogeny of the H19 methylation imprint," Nature Genetics, Nov. 1997, pp. 275-276, vol. 17.

Oue et al., "DNA methlation of multiple genes in gastric carcinoma: Association with histological type and CpG island methylator phenotype," Cancer Science, 2003, pp. 901-905, vol. 94.

Rein et al., "Identifying 5-methylcytosine and related modifications in DNA genomes," Nucleic Acids Research, 1998, pp. 2255-2264, vol. 26.

Sadri et al., "Rapid analysis of DNA methylation using new restriction enzyme sites created by bisulfite modification," Nucleic Acids Research, 1996, pp. 5058-5059, vol. 24.

Sanger et al., "DNA Sequencing with chain-terminating inhibitors," The Proceedings of the National Academy of Sciences, Dec. 1977, pp. 5463-5468, vol. 74.

Stites et al., "Clinical laboratory methods for detection of antigens and antibodies," *Basic and Clinical Immunology*, 7th ed., 1991, pp. 217-262, Appleton & Lange, Norwalk, Conn.

Strathdee et al., "Primary Ovarian Carcinomas Display Multiple Methylator Phenotypes Involving Known Tumor Suppressor Genes," American Journal of Pathology, 2001, pp. 1121-1127, vol. 158.

Toyota et al., "CpG island methylator phenotype in colorectal cancer," The Proceedings of the National Academy of Sciences, Jul. 1999, pp. 8681-8686, vol. 96.

Toyota et al., "Identification of Differentially Methylated Sequences in Colorectal Cancer by Methylated CpG Island Amplification," Cancer Research, May 15, 1999, pp. 2307-2312, vol. 59.

Van Der Krol et al., "Modulation of Eukaryotic Gene Expression by Complementary RNA or DNA Sequences," BioTechniques, 1988, pp. 958-976, vol. 6, No. 10.

Watson et al., "Isolation of Differentially Expressed Sequence Tags from Human Breast Cancer," Cancer Research, 1994, pp. 4598-4602, vol. 54.

Widschwendter et al., "Association of Breast Cancer DNA Methylation Profiles with Hormone Receptor Status and Response to Tamoxifen," Cancer Research, 2004, pp. 3807-3813, vol. 64.

Xiong et al., "COBRA: a sensitive and quantitative DNA methylation assay," Nucleic Acids Research, 1997, pp. 2532-2534, vol. 25, No. 12.

Yu et al., "Specific Inhibition of PCR by Non-Extendable Oligonucleotides Using a 5' to 3' Exonuclease-Deficient DNA Polymerase," BioTechniques, 1997, pp. 714-720, vol. 23, No. 4.

Zeschnigk et al., "Imprinted segments in the human genome: different DNA methylation pattersn in the Prader-Willi/Angelman syndrome region as determined by the genomic sequencing method," Human Molecular Genetics, 1997, pp. 387-395, vol. 6, No. 3.

Zeschnigk et al., "A single-tube PCR test for the diagnosis of Angelman and Prader-Willi syndrome based on allelic methylation differences at the SNRPN locus," European Journal of Human Genetics, Mar.-Apr. 1997, pp. 94-98, vol. 5, No. 2.

Zon, "Oligonucleotide Analogues as Potential Chemotherapeutic Agents," Pharmaceutical Research, 1988, pp. 539-549, Voume 5, No. 9.

* cited by examiner

DNA METHYLATION MARKERS ASSOCIATED WITH THE CPG ISLAND METHYLATOR PHENOTYPE (CIMP) IN HUMAN COLORECTAL CANCER

CROSS REFERENCE TO RELATED APPLICATIONS

The present application is a national submission under 35 U.S.C. 371, and claims the benefit of priority to International Application PCT/US2006/017160, filed 2 May 2006, which claims the benefit of priority to U.S. Provisional Patent Application No. 60/677,181, filed 2 May 2005, both of which are incorporated by reference herein in their entireties.

STATEMENT REGARDING FEDERAL SUPPORT

This work was supported by a NIH grant R01 CA075090, and the United States Government may have certain rights in this invention.

FIELD OF THE INVENTION

Aspects of the present invention relate generally to cancer and colorectal cancer, and more particularly to identification of, and diagnostic and/or prognostic use of novel validated DNA methylation markers associated with the CpG island methylator phenotype (CIMP) in colorectal cancer. The present invention also relates to genomic DNA sequences that exhibit altered expression patterns in disease states relative to normal. Particular embodiments provide, inter alia, novel methods, nucleic acids, nucleic acid arrays and kits useful for detecting, or for detecting and differentiating CIMP and/or cell proliferative disorders. Preferably, the methods, nucleic acids, nucleic acid arrays and kits for the detection and diagnosis of cell proliferative disorders are used for the diagnosis of CIMP, and in particular colorectal cancer.

SEQUENCE LISTING

A Sequence Listing, pursuant to 37 C.F.R. §1.52(e)(5), has been provided as part of this application on compact disc (1 of 1) as a 6.02 MB text file, entitled "47675-189 Sequence Listing.txt" ("180_0001.txt") and which is incorporated by reference herein in its entirety.

BACKGROUND

Cancer Epigenetics. Epigenetics refers to a switch between phenotypic states that is not based upon a change in genotype, such as a mutation, but is the result of a change in gene activity without any accompanying alteration of the DNA sequence. Simply put, this amounts to a stable change in gene expression. In cancer epigenetics, the most commonly observed situation is a change from a transcriptionally active gene to an epigenetically 'silenced' state. Epigenetic alterations are distinct from transitory changes in gene regulation, in that they involve relatively extensive, stable changes in chromatin structure, histone modification, associated protein composition, and in many cases, altered distribution of cytosine-5 DNA methylation at CpG dinucleotides in, for example, the promoter region of the gene. Of all of these molecular mechanisms, DNA methylation is the easiest to measure in archival samples, because cytosine methylation is retained in the genomic DNA throughout, for example, formalin-fixation, years of storage in paraffin blocks, and subsequent extraction from paraffin sections. Even heavily degraded, crosslinked DNA can be subjected successfully to DNA methylation analysis using, for example, bisulfite-based technique (e.g., with PCR amplicons, as is the case for the MethyLight™ technology).

The main targets for epigenetic gene silencing in cancer cells are promoter regions containing G:C- and CpG-rich stretches of DNA, called 'CpG islands.' CpG islands are G:C and CpG-rich stretches of DNA in the genome, often located in the vicinity of genes, and generally unmethylated in normal somatic tissues. Aberrant methylation of CpG islands has, for example, been documented in both benign and malignant human colorectal tumors and is associated with gene silencing.

It is important to note, however, that not all epigenetically silenced genes in cancer cells are tumor-suppressor genes, and that many of the affected CpG islands are not even located in promoter regions, and are not thought to affect gene expression (e.g., they may be in promoter regions of genes that are not expressed in either the normal or malignant cells of an organ giving rise to a malignancy). Yet, the occurrence of CpG island hypermethylation events is, in many cases, cancer-specific, suggesting a scenario in which the overall rate of CpG island hypermethylation during tumorigenesis needs to be sufficiently high to acquire the necessary hits at key loci, but at the same time perhaps affecting many other loci which are essentially innocent bystanders.

CIMP in colorectal cancer; prior art uncertainty and inconsistencies. A subset of colorectal tumors has been described to have an unusually high number of hypermethylated CpG islands, leading to the definition of a distinct phenotype, referred to as "CpG Island Methylator Phenotype", or "CIMP" (16, 21). Colorectal cancer has a lifetime incidence of 1 in 20, and CIMP cancers account for at least 15% of this, representing a large cohort of affected patients. Colorectal cancer has been traditionally been considered to be a single disease for the purposes of treatment, but recent evidence has suggested that there are different outcomes in sub-groups with distinct molecular features. Such CIMP+ colorectal tumors have been reported to have distinct profiles of genetic alterations, anatomic subsite, gender prevalence, histopathologic characteristics and clinical behavior.

However, a clear understanding of the CIMP phenomenon has been hampered by two complexities. First, the intricacy of the relationship between CIMP and microsatellite instability continues to result in different perspectives on the issue (38, 77). Second, the concept that CIMP affects only a subset of colorectal tumors and a subset of CpG islands, as opposed to all CpG islands known to be susceptible to hypermethylation, is not universally embraced or appreciated (38), and is further complicated by the fact that there are no firm rules for recognizing which CpG islands belong to the CIMP group. An initial panel of cancer-specifically methylated CpG island markers (21) has not been applied consistently in the literature, nor does it appear that all cancer-specifically methylated genes are affected by CIMP. Nevertheless, it seems clear that some CpG islands are more prone to cancer-specific hypermethylation than others. Thus, a lack of standardization in the classification methods used to define CIMP has resulted in varying and contradictory conclusions regarding, or example, the association of CIMP with a family history of cancer, and even the very existence of CIMP as a distinct subgroup of colorectal tumors. Not only has there been some ambiguity as to which CpG islands belong to the CIMP subset, but there has also been a lack of a uniform standard for applying this subset to the definition of CIMP status. The existence of unique CIMP-related etiologic and pathogenetic mechanisms can only be defined when this subgroup can be clearly and accurately identified. There are presently no clear guidelines for what constitutes CIMP-associated versus non-CIMP-associated CpG islands.

Therefore, there is a pronounced need in the art to further elucidate and understand the epidemiology and etiology of DNA methylation alterations in human colorectal cancer, and to clarify the uncertainties regarding the existence of CIMP and its classification. There is a pronounced need in the art to not only unambiguously confirm the existence of CIMP as a distinct subgroup of colorectal cancer, but also to establish an improved CIMP classification panel of methylation markers. There is a pronounced need in the art to provide compositions and methods for determining the relationship between CIMP status and molecular, demographic, and histopathologic features, and environmental risk factors. There is a pronounced in the art to understand the pathogenesis of this colorectal cancer subset and its association with risk factors so that we will be better placed to prevent its occurrence. There is a pronounced in the art to correctly identify cases which will best respond to particular therapies.

SUMMARY OF THE INVENTION

Applicants, as described herein, have provided definitive evidence for the existence of CIMP as a distinct trait among colorectal adenocarcinomas. Additionally, applicants have developed an improved method for the classification of CIMP. Furthermore, applicants have found that CIMP underlies almost all cases of sporadic MSI-H colorectal cancer and tumors with mutation of the BRAF oncogene.

Therefore, aspects of the present invention confirm the existence of a CpG island methylator phenotype (CIMP) in colorectal cancer, and provide novel validated DNA methylation markers associated with CIMP.

Additional aspects provide novel methods and compositions for determining CIMP status in colorectal cancers.

Particular aspects provide a panel of 14 CIMP genomic (preferably, particular CpG islands thereof described herein) markers corresponding to BCL2, BDNF, CACNA1G, CALCA, CRABP1, DLEC1, GATA3, HOXA1, IGF2, KL, NEUROG1, NR3C1, RUNX3, SOCS1 (Table 6), SEQ ID NOS:128-141, 114-127 and 100-113 (respective genomic, CpG island and amplicons, respectively) and a preferred sub panel of 5 genomic (preferably, particular CpG islands thereof described herein) markers (CACNA1G, IGF2, NEUROG1, RUNX3, and SOCS1), that provide, inter alia, an excellent classifier for CIMP status.

Additional preferred aspects provide a panel of three genomic and CpG island markers that identify KRAS mutant, BRAF wildtype tumors (CDKN2A, CRABP1 and NEUROG1); that is that are positively associated with KRAS mutation (after exclusion of BRAF mutant tumors, indicating that a separate KRAS-associated CIMP subgrouping exists with an overlapping set of methylation markers).

Further aspects provide novel methods and compositions for determining the relationship between CIMP status and other molecular features of the cancers including, but not limited to BRAF mutation, KRAS mutation and MSI status.

Additional aspects provide novel methods and compositions for determining the relationship between CIMP status and other variables including, but not limited to age, sex, tumor location, family history, race, country of origin, tumor characteristics (including, tumor type, tumor grade, invasive margin characteristics, lymphocyte infiltration characteristics, direct spread, lymph node spread, venous spread and type of residual adjacent polyp, if present).

Yet additional aspects provide novel methods and compositions for determining, between subgroups defined by CIMP status and BRAF mutations, effects of selected risk factors including, but not limited to body mass index, smoking history, alcohol intake, dietary folate intake, folate metabolic enzyme polymorphisms and history of hormonal use.

Further aspects of the present invention provide a foundation for a population-based study of CIMP, by providing a novel panel of very carefully selected methylation markers representing the CIMP subgroup, and having utility to classify CIMP.

DETAILED DESCRIPTION OF THE INVENTION

Figure 1:
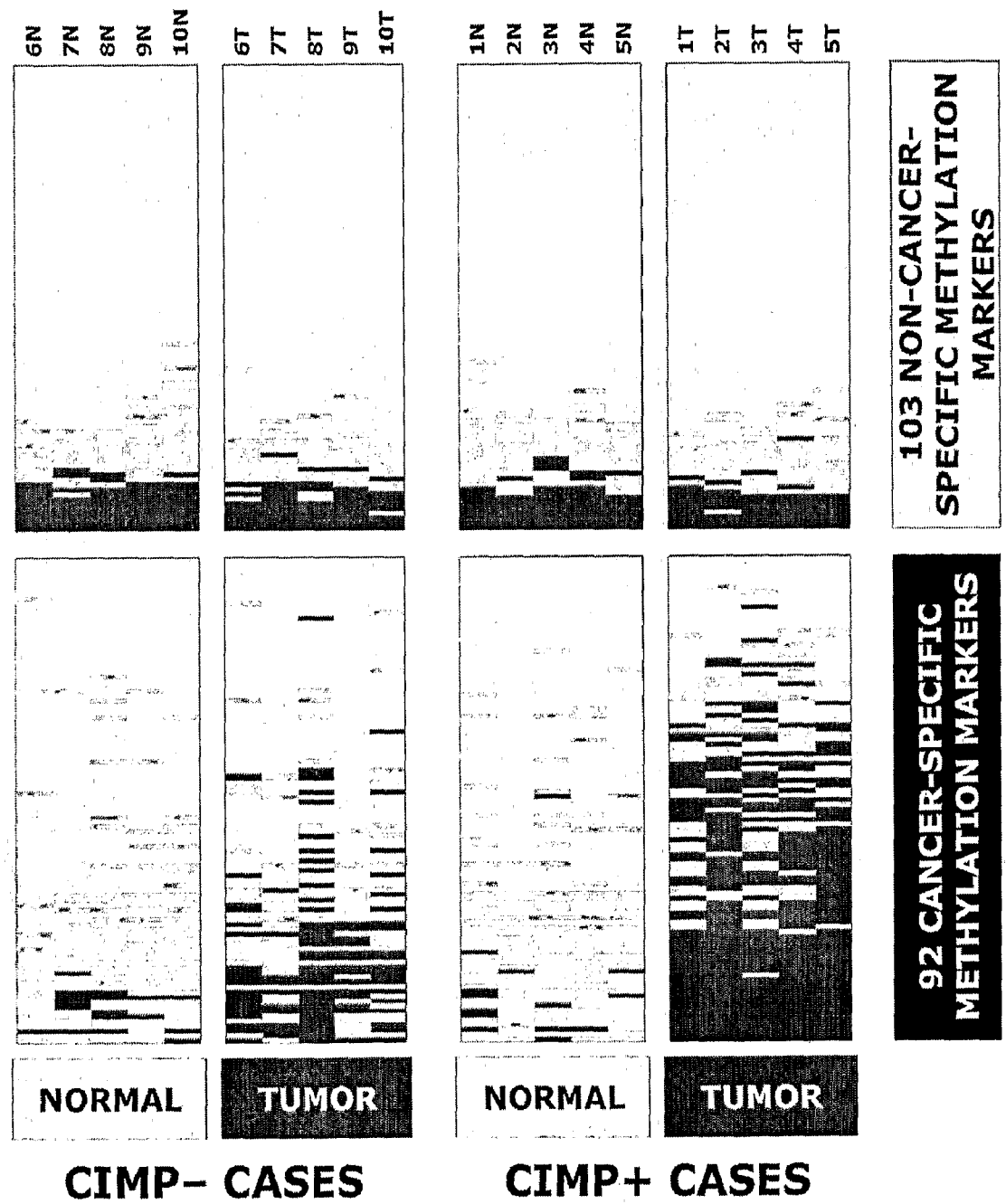
FIG. 1 shows an identification of Type C methylation markers. MethyLight™ analysis was performed for 195 MethyLight™ reactions on five CIMP+ and five CIMP− tumors as described in Methods (Example 1). Prior CIMP classification was performed as described in the Methods section "Tissue Samples". PMR values are indicated in color with a PMR of 0 (very light blue), less than 5 (light yellow), 5-50 (dark yellow), and above 50 (dark red). Genes selected for further evaluation are grouped at the bottom and sorted by increasing mean PMR from top to bottom.

Aspects of the present invention confirm the existence of a CpG island methylator phenotype (CIMP) in colorectal cancer, and provide novel validated DNA methylation markers associated with CIMP.

Additional aspects provide novel methods and compositions for determining CIMP status in colorectal cancers.

CIMP is a relatively new subclassification with an unknown underlying molecular defect. There is currently no external gold standard for defining CIMP, against which CIMP markers and panels can be compared and performance evaluated. Particular aspects disclose and describe a careful and methodical screen, starting with 195 different CpG islands, through a stepwise selection process involving the analysis of 245 different colorectal adenocarcinomas, and employing a battery of different cluster analysis routines, all of which identified the same subset of CIMP tumors, to arrive at a panel of 14 preferred CIMP markers (BCL2, BDNF, CACNA1G, CALCA, CRABP1, DLEC1, GATA3, HOXA1, IGF2, KL, NEUROG1, NR3C1, RUNX3, SOCS1) genomic markers (preferably, particular CpG islands thereof described herein) (TABLE 6), and a preferred sub panel of 5 markers (CACNA4G, IGF2, NEUROG1, RUNX3, and SOCS1) (preferably, particular CpG islands thereof described herein), that provide an excellent classifier for CIMP status.

Additional preferred aspects provide a panel of three genomic markers (CDKN2A, CRABP1 and NEUROG1) (preferably, particular CpG islands thereof described herein) that identify KRAS mutant, BRAF wildtype tumors.

Further aspects provide novel methods and compositions for determining the relationship between CIMP status and other molecular features of the cancers including, but not limited to BRAF mutation, KRAS mutation and MSI status.

Additional aspects provide novel methods and compositions for determining the relationship between CIMP status and other variables including, but not limited to age, sex, tumor location, family history, race, country of origin, tumor characteristics (including, tumor type, tumor grade, invasive margin characteristics, lymphocyte infiltration characteristics, direct spread, lymph node spread, venous spread and type of residual adjacent polyp, if present).

Yet additional aspects provide novel methods and compositions for determining, between subgroups defined by CIMP status and BRAF mutations, effects of selected risk factors including, but not limited to body mass index, smoking history, alcohol intake, dietary folate intake, folate metabolic enzyme polymorphisms and history of hormonal use.

TABLE 6

List of 14 Preferred CIMP markers, along with representative amplicons and respective associated coordinately-methylated CpG island sequences.

| HUGO Gene Nomenclature | Reaction Number | Reaction ID | GenBank Accession Number | MethyLight Amplicon Start (GenBank Numbering) | MethyLight Amplicon End (GenBank Numbering) | CpG Island Start (GenBank Numbering) | CpG Island End (GenBank Numbering) |
|---|---|---|---|---|---|---|---|
| BCL2 | HB-140 | BCL2-M1 | AY220759 | 1221 | 1304 | 746 | 1876 |
| BDNF | HB-258 | BDNF-M2 | AC103796 | 3794 | 3866 | 3351 | 4751 |
| CACNA1G | HB-158 | CACNA1G-M1 | AC021491 | 48345 | 48411 | 47327 | 49295 |
| CALCA | HB-166 | CALCA-M1 | X15943 | 1706 | 1806 | 1614 | 2359 |
| CRABP1 | HB-197 | CRABP1-M1 | AC011270 | 122223 | 122142 | 122717 | 120620 |
| DLEC1 | HB-225 | DLEC1-M1 | AP006309 | 19959 | 20088 | 19425 | 20529 |
| GATA3 | HB-327 | GATA3-M1 | AL390294 | 51880 | 51959 | 50613 | 54089 |
| HOXA1 | HB-268 | HOXA1-M2 | AC004079 | 78220 | 78138 | 79793 | 77693 |
| IGF2 | HB-319 | IGF2-M2 | AC132217 | 108633 | 108720 | 106219 | 110017 |
| KL | HB-175 | KL-M1 | AB009667 | 2062 | 2189 | 1239 | 3185 |
| NEUROG1 | HB-261 | NEUROG1-M1 | AC005738 | 75429 | 75342 | 76036 | 73946 |
| NR3C1 | HB-067 | NR3C1-M1 | AY436590 | 1786 | 1860 | 32 | 3034 |
| RUNX3 | HB-181 | RUNX3-M1 | AL023096 | 64762 | 64646 | 67973 | 63661 |
| SOCS1 | HB-042 | SOCS1-M1 | AC009121 | 108803 | 108888 | 107037 | 109517 |

Despite the lack of an external gold standard for CIMP classification, a comparison of cross-panel misclassification errors and the associations with other molecular features strongly indicates that the present novel panel outperforms a similar panel of five traditional markers derived from the initial CIMP classification paper (21) (MLH1, CDKN2A (p16$^{INK4A}$), MINT1, MINT2, and MINT31).

Applicants and others have reported a strong association between CIMP+ status in colorectal adenocarcinomas and mutation of the BRAF proto-oncogene (40, 42, 127, 131-133). With the present new CIMP classification panel, there is a remarkably strong association between CIMP+ status and BRAF mutation, with an odds ration of 203 (95% confidence interval=41,995), and a P-value of $1.6 \times 10^{-21}$ (see below).

In a particular study presented herein, 24 out of 26 mutant BRAF tumors were classified as CIMP+, while the 154 CIMP− tumors contained only two mutant BRAF tumors, along with 152 BRAF wildtype tumors (see also TABLE 4, Example 4).

TABLE 4

Distribution of covariates by New CIMP Panel.

| VARIABLE | | OVERALL N | % | CIMP+ (3-5 loci) N | % | CIMP− (0-2 loci) N | % | P-value |
|---|---|---|---|---|---|---|---|---|
| TOTAL | | 187 | 100% | 33 | 18% | 154 | 82% | |
| SEX | Male | 103 | 55% | 13 | 39% | 90 | 58% | |
| | Female | 84 | 45% | 20 | 61% | 64 | 42% | 0.05 |
| SUBSITE | Proximal | 57 | 33% | 19 | 59% | 38 | 27% | |
| | Distal | 118 | 67% | 13 | 41% | 105 | 73% | 0.0005 |
| | No Info | 12 | | | | | | |
| MSI | MSI-high | 21 | 11% | 12 | 36% | 9 | 6% | |
| STATUS | MSI-low | 19 | 10% | 4 | 12% | 15 | 10% | |
| | MSS | 147 | 79% | 17 | 52% | 130 | 84% | $3.1^{-5}$ |
| HNPCC | Yes | 8 | 4% | 0 | 0% | 8 | 5% | |
| STATUS | No | 179 | 96% | 33 | 100% | 146 | 95% | 0.35 |
| MLH1 | Yes | 16 | 9% | 13 | 39% | 3 | 2% | |
| METHYLATION | No | 171 | 91% | 20 | 61% | 151 | 98% | $2.6^{-9}$ |
| BRAF | Mutant | 26 | 14% | 24 | 73% | 2 | 1% | |
| MUTATION | WT | 161 | 86% | 9 | 27% | 152 | 99% | $1.6^{-21}$ |
| KRAS | Mutant | 55 | 31% | 3 | 10% | 52 | 35% | |
| MUTATION | WT | 123 | 69% | 28 | 90% | 95 | 65% | .002 |
| | No Info | 9 | | | | | | |
| MEAN AGE (SD)* | | 65.5 (12.9) | | 68.6 (12.7) | | 64.8 (12.9) | | 0.13 |

P-values are for likelihood ratio tests from logistic regression with CIMP status as the outcome. For the variable HNPCC we report the p-value from Fisher's exact test.
*Four CIMP− subjects are missing age.

Nevertheless, 9 out of 33 CIMP+ were wild-type for BRAF, indicating that BRAF mutant tumors represent a large subset of CIMP+ tumors, but that there are BRAF-independent CIMP+ tumors as well. Therefore, BRAF mutation appears to arise almost only in the context of CIMP+ status, indicating that this epigenetic phenomenon dominates over this particular genetic alteration in human colorectal cancer, which is a different conclusion from that reached in the art (see, e.g., 38).

Additionally, all 8 of the hereditary non-polyposis colorectal cancer (HNPCC)-associated MSI+ tumors were classified as CIMP−, while 12 out of 13 non-HNPCC MSI+ tumors were classified as CIMP+. On the other hand, 21 out of 33 of the CIMP+ tumors were MSI-low or MSS (see below). Therefore, non-HNPCC MSI+ colorectal tumors are a subset of CIMP+ tumors, but not the other way around, indicating that sporadic MSI+ colorectal cancer is largely attributable to the CIMP phenomenon. Thus, the present novel markers enables a well-executed population-based studies of CIMP, and a full etiologic understanding of MSI+ sporadic cancer.

Further aspects of the present invention, therefore, provide a foundation for a population-based study of CIMP, by providing a novel panel of very carefully selected methylation markers representing the CIMP subgroup, and having utility to classify CIMP.

Definitions

The term "Observed/Expected Ratio" ("O/E Ratio") refers to the frequency of CpG dinucleotides within a particular DNA sequence, and corresponds to the [number of CpG sites/(number of C bases×number of G bases)]/band length for each fragment.

The term "CpG island" refers to a contiguous region of genomic DNA that satisfies the criteria of (1) having a frequency of CpG dinucleotides corresponding to an "Observed/Expected Ratio">0.6, and (2) having a "GC Content">0.5. CpG islands are typically, but not always, between about 0.2 to about 1 KB, or to about 2 kb in length.

The term "methylation state" or "methylation status" refers to the presence or absence of 5-methylcytosine ("5-mCyt") at one or a plurality of CpG dinucleotides within a DNA sequence. Methylation states at one or more particular CpG methylation sites (each having two CpG dinucleotide sequences) within a DNA sequence include "unmethylated," "fully-methylated" and "hemi-methylated."

The term "hemi-methylation" or "hemimethylation" refers to the methylation state of a double stranded DNA wherein only one strand thereof is methylated.

The term 'AUC' as used herein is an abbreviation for the area under a curve. In particular it refers to the area under a Receiver Operating Characteristic (ROC) curve. The ROC curve is a plot of the true positive rate against the false positive rate for the different possible cut points of a diagnostic test. It shows the trade-off between sensitivity and specificity depending on the selected cut point (any increase in sensitivity will be accompanied by a decrease in specificity). The area under an ROC curve (AUC) is a measure for the accuracy of a diagnostic test (the larger the area the better, optimum is 1, a random test would have a ROC curve lying on the diagonal with an area of 0.5; for reference: J. P. Egan. Signal Detection Theory and ROC Analysis, Academic Press, New York, 1975).

The term "hypermethylation" refers to the average methylation state corresponding to an increased presence of 5-mCyt at one or a plurality of CpG dinucleotides within a DNA sequence of a test DNA sample, relative to the amount of 5-mCyt found at corresponding CpG dinucleotides within a normal control DNA sample.

The term "hypomethylation" refers to the average methylation state corresponding to a decreased presence of 5-mCyt at one or a plurality of CpG dinucleotides within a DNA sequence of a test DNA sample, relative to the amount of 5-mCyt found at corresponding CpG dinucleotides within a normal control DNA sample.

The term "microarray" refers broadly to both "DNA microarrays," and 'DNA chip(s),' as recognized in the art, encompasses all art-recognized solid supports, and encompasses all methods for affixing nucleic acid molecules thereto or synthesis of nucleic acids thereon.

"Genetic parameters" are mutations and polymorphisms of genes and sequences further required for their regulation. To be designated as mutations are, in particular, insertions, deletions, point mutations, inversions and polymorphisms and, particularly preferred, SNPs (single nucleotide polymorphisms).

"Epigenetic parameters" are, in particular, cytosine methylation. Further epigenetic parameters include, for example, the acetylation of histones which, however, cannot be directly analysed using the described method but which, in turn, correlate with the DNA methylation.

The term "bisulfite reagent" refers to a reagent comprising bisulfite, disulfite, hydrogen sulfite or combinations thereof, useful as disclosed herein to distinguish between methylated and unmethylated CpG dinucleotide sequences.

The term "Methylation assay" refers to any assay for determining the methylation state of one or more CpG dinucleotide sequences within a sequence of DNA.

The term "MS.AP-PCR" (Methylation-Sensitive Arbitrarily-Primed Polymerase Chain Reaction) refers to the art-recognized technology that allows for a global scan of the genome using CG-rich primers to focus on the regions most likely to contain CpG dinucleotides, and described by Gonzalgo et al., *Cancer Research* 57:594-599, 1997.

The term "MethyLight™" refers to the art-recognized fluorescence-based real-time PCR technique described by Eads et al., *Cancer Res.* 59:2302-2306, 1999.

The term "HeavyMethyl™" assay, in the embodiment thereof implemented herein, refers to an assay, wherein methylation specific blocking probes (also referred to herein as blockers) covering CpG positions between, or covered by the amplification primers enable methylation-specific selective amplification of a nucleic acid sample.

The term "HeavyMethyl™ MethyLight™" assay, in the embodiment thereof implemented herein, refers to a HeavyMethyl™ MethyLight™ assay, which is a variation of the MethyLight™ assay, wherein the MethyLight™ assay is combined with methylation specific blocking probes covering CpG positions between the amplification primers.

The term "Ms-SNuPE" (Methylation-sensitive Single Nucleotide Primer Extension) refers to the art-recognized assay described by Gonzalgo & Jones, *Nucleic Acids Res.* 25:2529-2531, 1997.

The term "MSP" (Methylation-specific PCR) refers to the art-recognized methylation assay described by Herman et al. *Proc. Natl. Acad. Sci. USA* 93:9821-9826, 1996, and by U.S. Pat. No. 5,786,146.

The term "COBRA" (Combined Bisulfite Restriction Analysis) refers to the art-recognized methylation assay described by Xiong & Laird, *Nucleic Acids Res.* 25:2532-2534, 1997.

The term "MCA" (Methylated CpG Island Amplification) refers to the methylation assay described by Toyota et al., *Cancer Res.* 59:2307-12, 1999, and in WO 00/26401A1.

The term "hybridisation" is to be understood as a bond of an oligonucleotide to a complementary sequence along the lines of the Watson-Crick base pairings in the sample DNA, forming a duplex structure.

"Stringent hybridisation conditions," as defined herein, involve hybridising at 68° C. in 5×SSC/5×Denhardt's solution/1.0% SDS, and washing in 0.2×SSC/0.1% SDS at room temperature, or involve the art-recognized equivalent thereof (e.g., conditions in which a hybridisation is carried out at 60° C. in 2.5×SSC buffer, followed by several washing steps at 37° C. in a low buffer concentration, and remains stable). Moderately stringent conditions, as defined herein, involve including washing in 3×SSC at 42° C., or the art-recognized equivalent thereof. The parameters of salt concentration and temperature can be varied to achieve the optimal level of identity between the probe and the target nucleic acid. Guidance regarding such conditions is available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

The terms "Methylation-specific restriction enzymes" or "methylation-sensitive restriction enzymes" shall be taken to mean an enzyme that selectively digests a nucleic acid dependant on the methylation state of its recognition site. In the case of such restriction enzymes which specifically cut if the recognition site is not methylated or hemimethylated, the cut will not take place, or with a significantly reduced efficiency, if the recognition site is methylated. In the case of such restriction enzymes which specifically cut if the recognition site is methylated, the cut will not take place, or with a significantly reduced efficiency if the recognition site is not methylated. Preferred are methylation-specific restriction enzymes, the recognition sequence of which contains a CG dinucleotide (for instance cgcg or cccggg). Further preferred for some embodiments are restriction enzymes that do not cut if the cytosine in this dinucleotide is methylated at the carbon atom C5.

"Non-methylation-specific restriction enzymes" or "non-methylation-sensitive restriction enzymes" are restriction enzymes that cut a nucleic acid sequence irrespective of the methylation state with nearly identical efficiency. They are also called "methylation-unspecific restriction enzymes."

The term "gene" shall be taken to include all transcript variants thereof (e.g. the term "NEUROG1" shall include for example its transcripts and any truncated transcript, etc) and all promoter and regulatory elements thereof. Furthermore as a plurality of SNPs are known within said gene the term shall be taken to include all sequence variants thereof.

The term "pre-cancerous" or "pre-neoplastic" and equivalents thereof shall be taken to mean any cellular proliferative disorder which is undergoing malignant transformation. Examples of such conditions include, in the context of colorectal cellular proliferative disorders, cellular proliferative disorders with a high degree of dysplasia and the following classes of adenomas:

Level 1: penetration of malignant glands through the muscularis mucosa into the submucosa, within the polyp head;

Level 2: the same submucosal invasion, but present at the junction of the head to the stalk;

Level 3: invasion of the stalk; and

Level 4: invasion of the stalk's base at the connection to the colonic wall (this level corresponds to stage Dukes A).

Exemplary Preferred Embodiments

In particular aspects, the present invention provides compositions and methods for at least one of: determining and/or classifying CIMP status in colorectal cancers; identifying KRAS mutant, BRAF wildtype tumors; determining the relationship between CIMP status and other molecular features of the cancers including, but not limited to BRAF mutation, KRAS mutation and MSI status; determining the relationship between CIMP status and other variables including, but not limited to age, sex, tumor location, family history, race, country of origin, tumor characteristics (including, tumor type, tumor grade, invasive margin characteristics, lymphocyte infiltration characteristics, direct spread, lymph node spread, venous spread and type of residual adjacent polyp, if present); determining, between subgroups defined by CIMP status and BRAF mutations, effects of selected risk factors including, but not limited to body mass index, smoking history, alcohol intake, dietary folate intake, folate metabolic enzyme polymorphisms and history of hormonal use; and providing a foundation for a population-based study of CIMP, by providing a novel panel of carefully selected methylation markers representing the CIMP subgroup, and having utility to classify CIMP.

Said methods comprising determining the methylation status or the expression levels of at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); SEQ ID NOS:128-141, 114-127 and 100-113 (respective genomic, CpG island and amplicons, respectively) in a biological sample isolated from said subject wherein underexpression and/or CpG methylation is indicative of the presence or class of said disorder. Said markers may be used for the methods listed above, and for diagnosis of neoplastic cellular proliferative disorders (cancer), including early detection during the pre-cancerous stages of the disease, and furthermore for the differentiation of neoplastic from benign cellular proliferative disorders. In particular aspects, the present invention discloses a method wherein a neoplastic cell proliferative disorder is distinguished from a benign cell proliferative disorder said method characterized in that underexpression and/or the presence of CpG methylation is indicative of the presence of a neoplastic cell proliferative disorder or pre-neoplastic disorder and the absence thereof is indicative of the presence of a benign cell proliferative disorder.

The markers of the present invention are particularly efficient in detecting or distinguishing between colorectal cell proliferative disorders, thereby providing improved means for the early detection, classification and treatment of said disorders.

In addition to the embodiments above wherein the methylation analysis of at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); SEQ ID NOS:128-141, 114-127 and 100-113 (respective genomic, CpG island and amplicons, respectively) is analysed, the invention presents further panels of genes comprising at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); SEQ ID NOS: 128-141, 114-127 and 100-113 (respective genomic, CpG island and amplicons, respectively) with novel utility for the detection of cancers, in particular colorectal cancer.

In a first further embodiment the present invention is based upon the analysis of CpG methylation status of at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); SEQ ID NOS:128-141, 114-127 and 100-113 (respective genomic, CpG island and amplicons, respectively).

Bisulfite modification of DNA is an art-recognized tool used to assess CpG methylation status. 5-methylcytosine is the most frequent covalent base modification in the DNA of eukaryotic cells. It plays a role, for example, in the regulation of the transcription, in genetic imprinting, and in tumorigenesis. Therefore, the identification of 5-methylcytosine as a component of genetic information is of considerable interest. However, 5-methylcytosine positions cannot be identified by sequencing, because 5-methylcytosine has the same base pairing behavior as cytosine. Moreover, the epigenetic information carried by 5-methylcytosine is completely lost during, e.g., PCR amplification.

The most frequently used method for analyzing DNA for the presence of 5-methylcytosine is based upon the specific reaction of bisulfite with cytosine whereby, upon subsequent alkaline hydrolysis, cytosine is converted to uracil which corresponds to thymine in its base pairing behavior. Significantly, however, 5-methylcytosine remains unmodified under these conditions. Consequently, the original DNA is converted in such a manner that methylcytosine, which originally could not be distinguished from cytosine by its hybridization behavior, can now be detected as the only remaining cytosine using standard, art-recognized molecular biological techniques, for example, by amplification and hybridization, or by sequencing. All of these techniques are based on differential base pairing properties, which can now be fully exploited.

The prior art, in terms of sensitivity, is defined by a method comprising enclosing the DNA to be analysed in an agarose matrix, thereby preventing the diffusion and renaturation of the DNA (bisulfite only reacts with single-stranded DNA), and replacing all precipitation and purification steps with fast dialysis (Olek A, et al., A modified and improved method for bisulfite based cytosine methylation analysis, *Nucleic Acids Res.* 24:5064-6, 1996). It is thus possible to analyse individual cells for methylation status, illustrating the utility and sensitivity of the method. An overview of art-recognized methods for detecting 5-methylcytosine is provided by Rein, T., et al., *Nucleic Acids Res.,* 26:2255, 1998.

The bisulfite technique, barring few exceptions (e.g., Zeschnigk M, et al., *Eur J Hum Genet.* 5:94-98, 1997), is currently only used in research. In all instances, short, specific fragments of a known gene are amplified subsequent to a bisulfite treatment, and either completely sequenced (Olek & Walter, *Nat. Genet.* 1997 17:275-6, 1997), subjected to one or more primer extension reactions (Gonzalgo & Jones, *Nucleic Acids Res.,* 25:2529-31, 1997; WO 95/00669; U.S. Pat. No. 6,251,594) to analyse individual cytosine positions, or treated by enzymatic digestion (Xiong & Laird, *Nucleic Acids Res.,* 25:2532-4, 1997). Detection by hybridisation has also been described in the art (Olek et al., WO 99/28498). Additionally, use of the bisulfite technique for methylation detection with respect to individual genes has been described (Grigg & Clark, *Bioessays,* 16:431-6, 1994; Zeschnigk M, et al., *Hum Mol. Genet.,* 6:387-95, 1997; Feil R, et al., *Nucleic Acids Res.,* 22:695-, 1994; Martin V, et al., *Gene,* 157:261-4, 1995; WO 9746705 and WO 9515373).

The present invention provides for the use of the bisulfite technique, in combination with one or more methylation assays, for determination of the methylation status of CpG dinucleotide sequences within at least one sequence selected from the group consisting of SEQ ID NOS:128-141, 114-127 and 100-113 (respective genomic, CpG island and amplicons, respectively). Genomic CpG dinucleotides can be methylated or unmethylated (alternatively known as up- and down-methylated respectively). However the methods of the present invention are suitable for the analysis of biological samples of a heterogeneous nature, e.g., a low concentration of tumor cells within a background of blood or stool. Accordingly, when analyzing the methylation status of a CpG position within such a sample the person skilled in the art may use a quantitative assay for determining the level (e.g., percent, fraction, ratio, proportion or degree) of methylation at a particular CpG position as opposed to a methylation state. Accordingly the term methylation status or methylation state should also be taken to mean a value reflecting the degree of methylation at a CpG position. Unless specifically stated the terms "hypermethylated" or "upmethylated" shall be taken to mean a methylation level above that of a specified cut-off point, wherein said cut-off may be a value representing the average or median methylation level for a given population, or is preferably an optimized cut-off level. The "cut-off" is also referred herein as a "threshold". In the context of the present invention the terms "methylated", "hypermethylated" or "upmethylated" shall be taken to include a methylation level above the cut-off be zero (0) % (or equivalents thereof) methylation for all CpG positions within and associated with (e.g. in promoter or regulatory regions) the genes or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); SEQ ID NOS:128-141, 114-127 and 100-113 (respective genomic, CpG island and amplicons, respectively).

According to the present invention, determination of the methylation status of CpG dinucleotide sequences BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively) has utility both in the diagnosis and characterization of CIMP.

Methylation Assay Procedures. Various methylation assay procedures are known in the art, and can be used in conjunction with the present invention. These assays allow for determination of the methylation state of one or a plurality of CpG dinucleotides (e.g., CpG islands) within a DNA sequence. Such assays involve, among other techniques, DNA sequencing of bisulfite-treated DNA, PCR (for sequence-specific amplification), Southern blot analysis, and use of methylation-sensitive restriction enzymes.

For example, genomic sequencing has been simplified for analysis of DNA methylation patterns and 5-methylcytosine distribution by using bisulfite treatment (Frommer et al., *Proc. Natl. Acad. Sci. USA* 89:1827-1831, 1992). Additionally, restriction enzyme digestion of PCR products amplified from bisulfite-converted DNA is used, e.g., the method described by Sadri & Hornsby (*Nucl. Acids Res.* 24:5058-5059, 1996), or COBRA (Combined Bisulfite Restriction Analysis) (Xiong & Laird, *Nucleic Acids Res.* 25:2532-2534, 1997).

COBRA. COBRA™ analysis is a quantitative methylation assay useful for determining DNA methylation levels at specific gene loci in small amounts of genomic DNA (Xiong & Laird, *Nucleic Acids Res.* 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (*Proc. Natl. Acad. Sci. USA* 89:1827-1831, 1992). PCR amplification of the bisulfite converted DNA is then performed using primers specific for the CpG islands of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples.

Typical reagents (e.g., as might be found in a typical COBRA™-based kit) for COBRA™ analysis may include, but are not limited to: PCR primers for specific gene (or bisulfite treated DNA sequence or CpG island); restriction enzyme and appropriate buffer; gene-hybridization oligonucleotide; control hybridization oligonucleotide; kinase labeling kit for oligonucleotide probe; and labeled nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

Preferably, assays such as "MethyLight™" (a fluorescence-based real-time PCR technique) (Eads et al., *Cancer Res.* 59:2302-2306, 1999), Ms-SNuPE™ (Methylation-sensitive Single Nucleotide Primer Extension) reactions (Gonzalgo & Jones, *Nucleic Acids Res.* 25:2529-2531, 1997), methylation-specific PCR ("MSP"; Herman et al., *Proc. Natl. Acad. Sci. USA* 93:9821-9826, 1996; U.S. Pat. No. 5,786,146), and methylated CpG island amplification ("MCA"; Toyota et al., *Cancer Res.* 59:2307-12, 1999) are used alone or in combination with other of these methods.

The "HeavyMethyl™" assay, technique is a quantitative method for assessing methylation differences based on methylation specific amplification of bisulfite treated DNA. Methylation specific blocking probes (also referred to herein as blockers) covering CpG positions between, or covered by the amplification primers enable methylation-specific selective amplification of a nucleic acid sample.

The term "HeavyMethyl™ MethyLight™" assay, in the embodiment thereof implemented herein, refers to a HeavyMethyl™ MethyLight™ assay, which is a variation of the MethyLight™ assay, wherein the MethyLight™ assay is combined with methylation specific blocking probes covering CpG positions between the amplification primers. The HeavyMethyl™ assay may also be used in combination with methylation specific amplification primers.

Typical reagents (e.g., as might be found in a typical MethyLight™-based kit) for HeavyMethyl™ analysis may include, but are not limited to: PCR primers for specific genes (or bisulfite treated DNA sequence or CpG island); blocking oligonucleotides; optimized PCR buffers and deoxynucleotides; and Taq polymerase.

MSP. MSP (methylation-specific PCR) allows for assessing the methylation status of virtually any group of CpG sites within a CpG island, independent of the use of methylation-sensitive restriction enzymes (Herman et al. *Proc. Natl. Acad. Sci. USA* 93:9821-9826, 1996; U.S. Pat. No. 5,786,146). Briefly, DNA is modified by sodium bisulfite converting all unmethylated, but not methylated cytosines to uracil, and subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific gene (or bisulfite treated DNA sequence or CpG island), optimized PCR buffers and deoxynucleotides, and specific probes.

MethyLight™. The MethyLight™ assay is a high-throughput quantitative methylation assay that utilizes fluorescence-based real-time PCR (TaqMan®) technology that requires no further manipulations after the PCR step (Eads et al., *Cancer Res.* 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed in a "biased" (with PCR primers that overlap known CpG dinucleotides) reaction. Sequence discrimination can occur both at the level of the amplification process and at the level of the fluorescence detection process.

The MethyLight™ assay may be used as a quantitative test for methylation patterns in the genomic DNA sample, wherein sequence discrimination occurs at the level of probe hybridization. In this quantitative version, the PCR reaction provides for a methylation specific amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the HeavyMethyl™ and MSP techniques), or with oligonucleotides covering potential methylation sites.

The MethyLight™ process can by used with any suitable probes e.g. "TaqMan®", Lightcycler® etc. . . . . . For example, double-stranded genomic DNA is treated with sodium bisulfite and subjected to one of two sets of PCR reactions using TaqMan® probes; e.g., with MSP primers and/or HeavyMethyl blocker oligonucleotides and TaqMan® probe. The TaqMan® probe is dual-labeled with fluorescent "reporter" and "quencher" molecules, and is designed to be specific for a relatively high GC content region so that it melts out at about 110° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical MethyLight™-based kit) for MethyLight™ analysis may include, but are not limited to: PCR primers for specific gene (or bisulfite treated DNA sequence or CpG island); TaqMan® or Lightcycler® probes; optimized PCR buffers and deoxynucleotides; and Taq polymerase.

The QM™ (quantitative methylation) assay is an alternative quantitative test for methylation patterns in genomic DNA samples, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the HeavyMethyl™ and MSP techniques), or with oligonucleotides covering potential methylation sites.

The QM process can by used with any suitable probes e.g. "TaqMan®", Lightcycler® etc. . . . in the amplification process. For example, double-stranded genomic DNA is treated with sodium bisulfite and subjected to unbiased primers and the TaqMan® probe. The TaqMan® probe is dual-labeled with fluorescent "reporter" and "quencher" molecules, and is designed to be specific for a relatively high GC content region so that it melts out at about 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system. Typical reagents (e.g., as might be found in a typical QM™-based kit) for QM™ analysis may include, but are not limited to: PCR primers for specific gene (or bisulfite treated DNA sequence or CpG island); TaqMan® or Lightcycler® probes; optimized PCR buffers and deoxynucleotides; and Taq polymerase.

Ms-SNuPE. The Ms-SNuPE™ technique is a quantitative method for assessing methylation differences at specific CpG sites based on bisulfite treatment of DNA, followed by single-nucleotide primer extension (Gonzalgo & Jones, *Nucleic Acids Res.* 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. Small amounts of DNA can be analyzed (e.g., microdissected pathology sections), and it avoids utilization of restriction enzymes for determining the methylation status at CpG sites.

Typical reagents (e.g., as might be found in a typical Ms-SNuPE™-based kit) for Ms-SNuPE™ analysis may include, but are not limited to: PCR primers for specific gene (or bisulfite treated DNA sequence or CpG island); optimized PCR buffers and deoxynucleotides; gel extraction kit; positive control primers; Ms-SNuPE™ primers for specific gene; reaction buffer (for the Ms-SNuPE reaction); and labelled nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

The Genomic Sequence According to SEQ ID NOS:128-141, 114-127 and 100-113 (Respective Genomic, CpG Island and Amplicons, Respectively), and Non-Naturally Occurring Treated Variants Thereof According to SEQ ID NOS:170-197, 226-253, 142-169 and 198-225, were Determined to have Novel Utility for the Detection, Classification and/or Treatment of CIMP, in Particular Colorectal Cell Proliferative Disorders In one embodiment the invention of the method comprises the following steps: i) contacting genomic DNA (preferably isolated from body fluids) obtained from the subject with at least one reagent, or series of reagents that distinguishes between methylated and non-methylated CpG dinucleotides within at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively) (including their promoter and regulatory regions); and ii) detecting, or detecting and distinguishing CIMP or colon proliferative disorders (e.g., afforded with a sensitivity of greater than or equal to 80% and a specificity of greater than or equal to 80%).

Preferably, the sensitivity is from about 75% to about 96%, or from about 80% to about 90%, or from about 80% to about 85%. Preferably, the specificity is from about 75% to about 96%, or from about 80% to about 90%, or from about 80% to about 85%.

Genomic DNA may be isolated by any means standard in the art, including the use of commercially available kits. Briefly, wherein the DNA of interest is encapsulated in by a cellular membrane the biological sample must be disrupted and lysed by enzymatic, chemical or mechanical means. The DNA solution may then be cleared of proteins and other contaminants, e.g., by digestion with proteinase K. The genomic DNA is then recovered from the solution. This may be carried out by means of a variety of methods including salting out, organic extraction or binding of the DNA to a solid phase support. The choice of method will be affected by several factors including time, expense and required quantity of DNA. All clinical sample types comprising neoplastic matter or pre-neoplastic matter are suitable for us e in the present method, preferred are cell lines, histological slides, biopsies, paraffin-embedded tissue, body fluids, stool, colonic effluent, urine, blood plasma, blood serum, whole blood, isolated blood cells, cells isolated from the blood and combinations thereof. Body fluids are the preferred source of the DNA; particularly preferred are blood plasma, blood serum, whole blood, isolated blood cells and cells isolated from the blood.

The genomic DNA sample is then treated with at least one reagent, or series of reagents that distinguishes between methylated and non-methylated CpG dinucleotides within at least one target region of the genomic DNA, wherein the target region comprises, or hybridizes under stringent conditions to a sequence of at least 16 contiguous nucleotides of at least one sequence selected from the group consisting of SEQ ID NOS:128-141, 114-127 and 100-113 (respective genomic, CpG island and amplicons, respectively), wherein said contiguous nucleotides comprise at least one CpG dinucleotide sequence.

It is particularly preferred that said reagent converts cytosine bases which are unmethylated at the 5'-position to uracil, thymine, or another base which is dissimilar to cytosine in terms of hybridisation behaviour. However in an alternative embodiment said reagent may be a methylation sensitive restriction enzyme.

Wherein the genomic DNA sample is treated in such a manner that cytosine bases which are unmethylated at the 5'-position are converted to uracil, thymine, or another base which is dissimilar to cytosine in terms of hybridization behavior It is preferred that this treatment is carried out with bisulfite (hydrogen sulfite, disulfite) and subsequent alkaline hydrolysis. Such a treatment results in the conversion of SEQ ID NOS:128-141, 114-127 and 100-113 (respective genomic, CpG island and amplicons, respectively) to SEQ ID NOS: 170-197 and 142-169, (respectively) wherein said CpG dinucleotides are methylated or SEQ ID NOS:226-253 and 198-225 wherein said CpG dinucleotides are unmethylated.

The treated DNA is then analysed in order to determine the methylation state of the target gene sequences (at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively) prior to the treatment). It is particularly preferred that the target region comprises, or hybridizes under stringent conditions to at least 16 contiguous nucleotides of at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively). It is preferred that the sequence of said genes according to SEQ ID NOS:128-141, 114-127 and 100-113 (respective genomic, CpG island and amplicons, respectively) are analysed. The method of analysis may be selected from those known in the art, including those listed herein. Particularly preferred are MethyLight™, MSP and the use of blocking oligonucleotides (HeavyMethyl™) as described herein. It is further preferred that any oligonucleotides used in such analysis (including primers, blocking oligonucleotides and detection probes) should be reverse complementary, identical, or hybridise under stringent or highly stringent conditions to an at least 16-base-pair long segment of the base sequences of one or more of SEQ ID NOS:170-197, 226-253, 142-169 and 198-225 and sequences complementary thereto.

Aberrant methylation, more specifically hypermethylation of the genes or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively) (including their promoter and/or regulatory regions) is associated with the presence of CIMP, and is particularly prevalent in colorectal carcinomas. Accordingly, in certain embodiments, wherein a biological sample presents within methylation as disclosed herein, said sample should be determined as CIMP.

Analysis of one the genes or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively) enables for the first time detecting, or detecting and distinguishing CIMP or colon cell proliferative disorders (e.g., afforded with a sensitivity of greater than or equal to 80% and a specificity of greater than or equal to 80%. Sensitivity is calculated as: (detected neoplasia/all neoplasia; e.g., (detected colon neoplasia/all colon neoplasia); and specificity is calculated as (non-detected negatives/total negatives)).

Preferably, the sensitivity is from about 75% to about 96%, or from about 80% to about 90%, or from about 80% to about 85%. Preferably, the specificity is from about 75% to about 96%, or from about 80% to about 90%, or from about 80% to about 85%.

For certain embodiments, colon neoplasia is herein defined as all colon malignancies and adenomas greater than 1 cm., or subsets thereof. Negatives can be defined as healthy individuals.

In one embodiment the method discloses the use of at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively) (or promoter and/or regulatory regions thereof) as a marker for detection and distinguishing of CIMP, etc. as described herein.

Said method may be enabled by means of any analysis of the expression of an RNA transcribed therefrom or polypeptide or protein translated from said RNA, preferably by means of mRNA expression analysis or polypeptide expression analysis. Accordingly the present invention also provides diagnostic assays and methods, both quantitative and qualitative for detecting the expression of at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively) in a subject and determining therefrom upon the presence or absence of, e.g., CIMP, etc., in said subject.

Aberrant expression of mRNA transcribed from the genes or genomic sequences selected from the group consisting of BCL2, BDNF, CACNA1G, CALCA, CRABP1, DLEC1, GATA3, HOXA4, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively) are associated with the presence of CIMP, cancer in a subject. According to particular aspects of the present invention, under expression (and/or presence methylation) is associated with the presence of CIMP, colon cancer, and vice versa over-expression (and/or absence of methylation) is associated with the absence of CIMP, colon cancer.

To detect the presence of mRNA encoding a gene or genomic sequence, a sample is obtained from a patient. The sample may be any suitable sample comprising cellular matter of the tumour. Suitable sample types include cell lines, histological slides, biopsies, paraffin-embedded tissue, body fluids, stool, colonic effluent, urine, blood plasma, blood serum, whole blood, isolated blood cells, cells isolated from the blood and all possible combinations thereof. It is preferred that said sample types are stool or body fluids selected from the group consisting colonic effluent, urine, blood plasma, blood serum, whole blood, isolated blood cells, cells isolated from the blood.

The sample may be treated to extract the RNA contained therein. The resulting nucleic acid from the sample is then analyzed. Many techniques are known in the state of the art for determining absolute and relative levels of gene expression, commonly used techniques suitable for use in the present invention include in situ hybridisation (e.g., FISH), Northern analysis, RNase protection assays (RPA), microarrays and PCR-based techniques, such as quantitative PCR and differential display PCR or any other nucleic acid detection method.

Particularly preferred is the use of the reverse transcription/polymerisation chain reaction technique (RT-PCR). The method of RT-PCR is well known in the art (for example, see Watson and Fleming, supra).

The RT-PCR method can be performed as follows. Total cellular RNA is isolated by, for example, the standard guanidium isothiocyanate method and the total RNA is reverse transcribed. The reverse transcription method involves synthesis of DNA on a template of RNA using a reverse transcriptase enzyme and a 3' end oligonucleotide dT primer and/or random hexamer primers. The cDNA thus produced is then amplified by means of PCR. (Belyavsky et al, Nucl Acid Res 17:2919-2932, 1989; Krug and Berger, Methods in Enzymology, Academic Press, N.Y., Vol. 152, pp. 316-325, 1987 which are incorporated by reference). Further preferred is the "Real-time" variant of RT-PCR, wherein the PCR product is detected by means of hybridisation probes (e.g. TaqMan, Lightcycler, Molecular Beacons & Scorpion) or SYBR green. The detected signal from the probes or SYBR green is then quantitated either by reference to a standard curve or by comparing the Ct values to that of a calibration standard. Analysis of housekeeping genes is often used to normalize the results.

In Northern blot analysis total or poly(A)+ mRNA is run on a denaturing agarose gel and detected by hybridisation to a labelled probe in the dried gel itself or on a membrane. The resulting signal is proportional to the amount of target RNA in the RNA population.

Comparing the signals from two or more cell populations or tissues reveals relative differences in gene expression levels. Absolute quantitation can be performed by comparing the signal to a standard curve generated using known amounts of an in vitro transcript corresponding to the target RNA. Analysis of housekeeping genes, genes whose expression levels are expected to remain relatively constant regardless of conditions, is often used to normalize the results, eliminating any apparent differences caused by unequal transfer of RNA to the membrane or unequal loading of RNA on the gel.

The first step in Northern analysis is isolating pure, intact RNA from the cells or tissue of interest. Because Northern blots distinguish RNAs by size, sample integrity influences the degree to which a signal is localized in a single band. Partially degraded RNA samples will result in the signal being smeared or distributed over several bands with an overall loss in sensitivity and possibly an erroneous interpretation of the data. In Northern blot analysis, DNA, RNA and oligonucleotide probes can be used and these probes are preferably labelled (e.g., radioactive labels, mass labels or fluorescent labels). The size of the target RNA, not the probe, will determine the size of the detected band, so methods such as random-primed labelling, which generates probes of variable lengths, are suitable for probe synthesis. The specific activity of the probe will determine the level of sensitivity, so it is preferred that probes with high specific activities, are used.

In an RNase protection assay, the RNA target and an RNA probe of a defined length are hybridised in solution. Following hybridisation, the RNA is digested with RNases specific for single-stranded nucleic acids to remove any unhybridized, single-stranded target RNA and probe. The RNases are inactivated, and the RNA is separated e.g. by denaturing polyacrylamide gel electrophoresis. The amount of intact RNA probe is proportional to the amount of target RNA in the RNA population. RPA can be used for relative and absolute quantitation of gene expression and also for mapping RNA structure, such as intron/exon boundaries and transcription start sites. The RNase protection assay is preferable to Northern blot analysis as it generally has a lower limit of detection.

The antisense RNA probes used in RPA are generated by in vitro transcription of a DNA template with a defined endpoint and are typically in the range of 50-600 nucleotides. The use of RNA probes that include additional sequences not homologous to the target RNA allows the protected fragment to be distinguished from the full-length probe. RNA probes are typically used instead of DNA probes due to the ease of generating single-stranded RNA probes and the reproducibility and reliability of RNA:RNA duplex digestion with RNases (Ausubel et al. 2003), particularly preferred are probes with high specific activities.

Particularly preferred is the use of microarrays. The microarray analysis process can be divided into two main parts. First is the immobilization of known gene sequences onto glass slides or other solid support followed by hybridisation of the fluorescently labelled cDNA (comprising the sequences to be interrogated) to the known genes immobilized on the glass slide (or other solid phase). After hybridisation, arrays are scanned using a fluorescent microarray scanner. Analysing the relative fluorescent intensity of different genes provides a measure of the differences in gene expression.

DNA arrays can be generated by immobilizing presynthesized oligonucleotides onto prepared glass slides or other solid surfaces. In this case, representative gene sequences are manufactured and prepared using standard oligonucleotide synthesis and purification methods. These synthesized gene sequences are complementary to the RNA transcript(s) of the genes of interest (in this case the genes or genomic sequences selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively) and tend to be shorter sequences in the range of 25-70 nucleotides. Alternatively, immobilized oligos can be chemically synthesized in situ on the surface of the slide. In situ oligonucleotide synthesis involves the consecutive addition of the appropriate nucleotides to the spots on the microarray; spots not receiving a nucleotide are protected during each stage of the process using physical or virtual masks. Preferably said synthesized nucleic acids are locked nucleic acids.

In expression profiling microarray experiments, the RNA templates used are representative of the transcription profile of the cells or tissues under study. RNA is first isolated from the cell populations or tissues to be compared. Each RNA sample is then used as a template to generate fluorescently labelled cDNA via a reverse transcription reaction. Fluorescent labelling of the cDNA can be accomplished by either direct labelling or indirect labelling methods. During direct labelling, fluorescently modified nucleotides (e.g., Cy®3- or Cy®5-dCTP) are incorporated directly into the cDNA during the reverse transcription. Alternatively, indirect labelling can be achieved by incorporating aminoallyl-modified nucleotides during cDNA synthesis and then conjugating an N-hydroxysuccinimide (NHS)-ester dye to the aminoallyl-modified cDNA after the reverse transcription reaction is complete. Alternatively, the probe may be unlabelled, but may be detectable by specific binding with a ligand which is labelled, either directly or indirectly. Suitable labels and methods for labelling ligands (and probes) are known in the art, and include, for example, radioactive labels which may be incorporated by known methods (e.g., nick translation or kinasing). Other suitable labels include but are not limited to biotin, fluorescent groups, chemiluminescent groups (e.g., dioxetanes, particularly triggered dioxetanes), enzymes, antibodies, and the like.

To perform differential gene expression analysis, cDNA generated from different RNA samples are labelled with Cy®3. The resulting labelled cDNA is purified to remove unincorporated nucleotides, free dye and residual RNA. Following purification, the labelled cDNA samples are hybridised to the microarray. The stringency of hybridisation is determined by a number of factors during hybridisation and during the washing procedure, including temperature, ionic strength, length of time and concentration of formamide. These factors are outlined in, for example, Sambrook et al. (Molecular Cloning: A Laboratory Manual, 2nd ed., 1989). The microarray is scanned post-hybridisation using a fluorescent microarray scanner. The fluorescent intensity of each spot indicates the level of expression of the analysed gene; bright spots correspond to strongly expressed genes, while dim spots indicate weak expression.

Once the images are obtained, the raw data must be analysed. First, the background fluorescence must be subtracted from the fluorescence of each spot. The data is then normalized to a control sequence, such as exogenously added nucleic acids (preferably RNA or DNA), or a housekeeping gene panel to account for any non-specific hybridisation, array imperfections or variability in the array set-up, cDNA labelling, hybridisation or washing. Data normalization allows the results of multiple arrays to be compared.

Another aspect of the invention relates to a kit for use in diagnosis of cancer in a subject according to the methods of the present invention, said kit comprising: a means for measuring the level of transcription of genes or genomic sequences selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively). In a preferred embodiment, the means for measuring the level of transcription comprise oligonucleotides or polynucleotides able to hybridise under stringent or moderately stringent conditions to the transcription products of a gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively). Preferably said oligonucleotides or polynucleotides are able to hybridise under stringent or moderately stringent conditions to at least one of the transcription products of a gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively). In one embodiment said oligonucleotides or polynucleotides comprise at least 9, 18 or 25 bases of a sequence complementary to or hybrising to at least one sequence selected from the group consisting of SEQ ID NOS:254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332 and 334 and sequences complementary thereto.

In a most preferred embodiment, the level of transcription is determined by techniques selected from the group of Northern Blot analysis, reverse transcriptase PCR, real-time PCR, RNAse protection, and microarray. In another embodiment of the invention the kit further comprises means for obtaining a biological sample of the patient. Preferred is a kit, which further comprises a container which is most preferably suitable for containing the means for measuring the level of transcription and the biological sample of the patient, and most preferably further comprises instructions for use and interpretation of the kit results.

In a preferred embodiment the kit comprises (a) a plurality of oligonucleotides or polynucleotides able to hybridise under stringent or moderately stringent conditions to the transcription products of at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively); (b) a container, preferably suitable for containing the oligonucleotides or polynucleotides and a biological sample of the patient comprising the transcription products wherein the oligonucleotides or polynucleotides can hybridise under stringent or moderately stringent conditions to the transcription products, (c) means to detect the hybridisation of (b); and optionally, (d) instructions for use and interpretation of the kit results. It is further preferred that said oligonucleotides or polynucleotides of (a) comprise in each case at least 9, 18 or 25 bases of a sequence complementary to or hybridising to at least one sequence selected from the group consisting of SEQ ID NOS:254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332 and 334 and sequences complementary thereto.

The kit may also contain other components such as hybridisation buffer (where the oligonucleotides are to be used as a probe) packaged in a separate container. Alternatively, where the oligonucleotides are to be used to amplify a target region, the kit may contain, packaged in separate containers, a polymerase and a reaction buffer optimised for primer extension mediated by the polymerase, such as PCR. Preferably said polymerase is a reverse transcriptase. It is further preferred that said kit further contains an Rnase reagent.

The present invention further provides for methods for the detection of the presence of the polypeptide encoded by said gene sequences in a sample obtained from a patient.

Aberrant levels of polypeptide expression of the polypeptides encoded by the genes or genomic sequences selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively) are associated with CIMP and/or the presence of colon cancer.

According to the present invention, under expression of said polypeptides is associated with the presence of CIMP and/or the presence of colon cancer. It is particularly preferred that said polypeptides are according to at least one of the amino acid sequences provided in SEQ ID NOS:255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333 and 335 polypeptides transcribed from the BCL2, BDNF, CACNA1G, CALCA, CRABP1, DLEC1, GATA3, HOXA1, IGF2, KL, NEUROG1, NR3C1, RUNX3, SOCS1 (Table 6) genes).

Any method known in the art for detecting polypeptides can be used. Such methods include, but are not limited to mass-spectrometry, immunodiffusion, immunoelectrophoresis, immunochemical methods, binder-ligand assays, immunohistochemical techniques, agglutination and complement assays (e.g., see Basic and Clinical Immunology, Sites and Terr, eds., Appleton & Lange, Norwalk, Conn. pp 217-262, 1991 which is incorporated by reference). Preferred are binder-ligand immunoassay methods including reacting antibodies with an epitope or epitopes and competitively displacing a labelled polypeptide or derivative thereof.

Certain embodiments of the present invention comprise the use of antibodies specific to the polypeptide encoded by a gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively). It is particularly preferred that said polypeptides are according to at least one of the amino acid sequences provided in SEQ ID NOS:255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333 and 335.

Such antibodies are useful for CIMP and/or cancer diagnosis. In certain embodiments production of monoclonal or polyclonal antibodies can be induced by the use of an epitope encoded by a polypeptide of SEQ ID NOS:255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333 and 335 as an antigene. Such antibodies may in turn be used to detect expressed polypeptides as markers for CIMP and/or cancer diagnosis. The levels of such polypeptides present may be quantified by conventional methods. Antibody-polypeptide binding may be detected and quantified by a variety of means known in the art, such as labelling with fluorescent or radioactive ligands. The invention further comprises kits for performing the above-mentioned procedures, wherein such kits contain antibodies specific for the investigated polypeptides.

Numerous competitive and non-competitive polypeptide binding immunoassays are well known in the art. Antibodies employed in such assays may be unlabelled, for example as used in agglutination tests, or labelled for use a wide variety of assay methods. Labels that can be used include radionuclides, enzymes, fluorescers, chemiluminescers, enzyme substrates or co-factors, enzyme inhibitors, particles, dyes and the like. Preferred assays include but are not limited to radioimmunoassay (RIA), enzyme immunoassays, e.g., enzyme-linked immunosorbent assay (ELISA), fluorescent immunoassays and the like. Polyclonal or monoclonal antibodies or epitopes thereof can be made for use in immunoassays by any of a number of methods known in the art.

In an alternative embodiment of the method the proteins may be detected by means of western blot analysis. Said analysis is standard in the art, briefly proteins are separated by means of electrophoresis, e.g., SDS-PAGE. The separated proteins are then transferred to a suitable membrane (or paper), e.g., nitrocellulose, retaining the spacial separation achieved by electrophoresis. The membrane is then incubated with a blocking agent to bind remaining sticky places on the membrane, commonly used agents include generic protein (e.g., milk protein). An antibody specific to the protein of interest is then added, said antibody being detectably labelled for example by dyes or enzymatic means (e.g., alkaline phosphatase or horseradish peroxidase). The location of the antibody on the membrane is then detected.

In an alternative embodiment of the method the proteins may be detected by means of immunohistochemistry (the use of antibodies to probe specific antigens in a sample). Said analysis is standard in the art, wherein detection of antigens in tissues is known as immunohistochemistry, while detection in cultured cells is generally termed immunocytochemistry. Briefly, the primary antibody to be detected by binding to its specific antigen. The antibody-antigen complex is then bound by a secondary enzyme conjugated antibody. In the presence of the necessary substrate and chromogen the bound enzyme is detected according to coloured deposits at the antibody-antigen binding sites. There is a wide range of suitable sample types, antigen-antibody affinity, antibody types, and detection enhancement methods. Thus optimal conditions for immunohistochemical or immunocytochemical detection must be determined by the person skilled in the art for each individual case.

One approach for preparing antibodies to a polypeptide is the selection and preparation of an amino acid sequence of all or part of the polypeptide, chemically synthesising the amino acid sequence and injecting it into an appropriate animal, usually a rabbit or a mouse (Milstein and Kohler Nature 256:495-497, 1975; Gulfre and Milstein, Methods in Enzymology: Immunochemical Techniques 73:1-46, Langone and Banatis eds., Academic Press, 1981 which are incorporated by reference in its entirety). Methods for preparation of the polypeptides or epitopes thereof include, but are not limited to chemical synthesis, recombinant DNA techniques or isolation from biological samples.

In the final step of the method the diagnosis of the patient is determined, whereby under-expression (of at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively) is indicative of the presence of CIMP and/or cancer. The term under-expression shall be taken to mean expression at a detected level less than a pre-determined cut off which may be selected from the group consisting of the mean, median or an optimised threshold value.

Another aspect of the invention provides a kit for use in diagnosis of CIMP and/or cancer in a subject according to the methods of the present invention, comprising: a means for detecting polypeptides at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively). Preferably the sequence of said polypeptides is as provided in SEQ ID NOS:255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333 and 335. The means for detecting the polypeptides comprise preferably antibodies, antibody derivatives, or antibody fragments. The polypeptides are most preferably detected by means of Western Blotting utilizing a labelled antibody. In another embodiment of the invention the kit further comprising means for obtaining a biological sample of the patient. Preferred is a kit, which further comprises a container suitable for containing the means for detecting the polypeptides in the biological sample of the patient, and most preferably further comprises instructions for use and interpretation of the kit results. In a preferred embodiment the kit comprises: (a) a means for detecting polypeptides at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively); (b) a container suitable for containing the said means and the biological sample of the patient comprising the polypeptides wherein the means can form complexes with the polypeptides; (c) a means to detect the complexes of (b); and optionally (d) instructions for use and interpretation of the kit results. It is preferred that said means for detecting polypeptides of at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively) are specific for at least one of the polypeptide sequences selected from SEQ ID NOS:255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333 and 335. The kit may also contain other components such as buffers or solutions suitable for blocking, washing or coating, packaged in a separate container.

Particular embodiments of the present invention provide a novel application of the analysis of methylation levels and/or patterns within said sequences that enables a precise detection, characterisation and/or treatment of CIMP and/or colorectal cell proliferative disorders. Early detection of CIMP is directly linked with disease prognosis, and the disclosed method thereby enables the physician and patient to make better and more informed treatment decisions.

Further Improvements

The present invention provides novel compositions and uses as disclosed herein for genomic (e.g., CpG island) markers corresponding to at least one of BCL2, BDNF, CACNA1G, CALCA, CRABP1, DLEC1, GATA3, HOXA1, IGF2, KL, NEUROG1, NR3C1, RUNX3, SOCS1 (Table 6) sequences corresponding to e.g., within SEQ ID NOS:128-141, 114-127 and 100-113 (respective genomic, CpG island and amplicons, respectively). Additional embodiments provide modified variants of e.g., within SEQ ID NOS:128-141, 114-127 and 100-113 (respective genomic, CpG island and amplicons, respectively), as well as oligonucleotides and/or PNA-oligomers for analysis of cytosine methylation patterns within e.g., within SEQ ID NOS:128-141, 114-127 and 100-113 (respective genomic, CpG island and amplicons, respectively).

An objective of the invention comprises analysis of the methylation state of one or more CpG dinucleotides within at least one sequence selected form the group consisting of e.g., within SEQ ID NOS:128-141, 114-127 and 100-113 (respective genomic, CpG island and amplicons, respectively) and sequences complementary thereto.

The disclosed invention provides treated nucleic acids, derived from genomic e.g., within SEQ ID NOS:128-141, 114-127 and 100-113 (respective genomic, CpG island and amplicons, respectively), wherein the treatment is suitable to convert at least one unmethylated cytosine base of the genomic DNA sequence to uracil or another base that is detectably dissimilar to cytosine in terms of hybridization. The genomic sequences in question may comprise one, or more consecutive methylated CpG positions. Said treatment preferably comprises use of a reagent selected from the group consisting of bisulfite, hydrogen sulfite, disulfite, and combinations thereof. In a preferred embodiment of the invention, the invention provides a non-naturally occurring modified nucleic acid comprising a sequence of at least 16 contiguous nucleotide bases in length of a sequence selected from the group consisting of SEQ ID NOS:170-197, 226-253, 142-169 and 198-225. In further preferred embodiments of the invention said nucleic acid is at least 50, 100, 150, 200, 250 or 500 base pairs in length of a segment of the nucleic acid sequence disclosed in SEQ ID NOS:170-197, 226-253, 142-169 and 198-225. Particularly preferred is a nucleic acid molecule that is identical or complementary to all or a portion of the sequences SEQ ID NOS:170-197, 226-253, 142-169 and 198-225 but not SEQ ID NOS:128-141, 114-127 and 100-113 (respective genomic, CpG island and amplicons, respectively) or other naturally occurring DNA.

It is preferred that said sequence comprises at least one CpG, TpA or CpA dinucleotide and sequences complementary thereto. The sequences of SEQ ID NOS:170-197, 226-253, 142-169 and 198-225 provide non-naturally occurring modified versions of the nucleic acid according to SEQ ID NOS:128-141, 114-127 and 100-113 (respective genomic, CpG island and amplicons, respectively), wherein the modification of each genomic sequence results in the synthesis of a nucleic acid having a sequence that is unique and distinct from said genomic sequence as follows. For each sense strand genomic DNA, e.g., SEQ ID NO:1, four converted versions are disclosed. A first version wherein "C" is converted to "T," but "CpG" remains "CpG" (i.e., corresponds to case where, for the genomic sequence, all "C" residues of CpG dinucleotide sequences are methylated and are thus not converted); a second version discloses the complement of the disclosed genomic DNA sequence (i.e. antisense strand), wherein "C" is converted to "T," but "CpG" remains "CpG" (i.e., corresponds to case where, for all "C" residues of CpG dinucleotide sequences are methylated and are thus not converted). The 'upmethylated' converted sequences of SEQ ID NOS: 128-141, 114-127 and 100-113 (respective genomic, CpG island and amplicons, respectively) correspond to SEQ ID NOS:170-197 and 142-169. A third chemically converted version of each genomic sequences is provided, wherein "C" is converted to "T" for all "C" residues, including those of "CpG" dinucleotide sequences (i.e., corresponds to case where, for the genomic sequences, all "C" residues of CpG dinucleotide sequences are unmethylated); a final chemically converted version of each sequence, discloses the complement of the disclosed genomic DNA sequence (i.e. antisense strand), wherein "C" is converted to "T" for all "C" residues, including those of "CpG" dinucleotide sequences (i.e., corresponds to case where, for the complement (antisense strand) of each genomic sequence, all "C" residues of CpG dinucleotide sequences are unmethylated). The 'downmethylated' converted sequences of SEQ ID NOS:128-141, 114-127 and 100-113 (respective genomic, CpG island and amplicons, respectively) correspond to SEQ ID NOS:226-253 and 198-225.

Significantly, heretofore, the nucleic acid sequences and molecules according SEQ ID NOS:170-197, 226-253, 142-169 and 198-225 were not implicated in or connected with the detection, classification or treatment of cellular proliferative disorders.

In an alternative preferred embodiment, the invention further provides oligonucleotides or oligomers suitable for use in the methods of the invention for detecting the cytosine methylation state within genomic or treated (chemically modified) DNA, according to SEQ ID NOS:128-141, 114-127 and 100-113 (respective genomic, CpG island and amplicons, respectively), SEQ ID NOS:170-197, 226-253, 142-169 and 198-225. Said oligonucleotide or oligomer nucleic acids provide novel diagnostic means. Said oligonucleotide or oligomer comprising a nucleic acid sequence having a length of at least nine (9) nucleotides which is identical to, hybridizes, under moderately stringent or stringent conditions (as defined herein above), to a treated nucleic acid sequence according to SEQ ID NOS:170-197, 226-253, 142-169 and 198-225 and/or sequences complementary thereto, or to a genomic sequence according to SEQ ID NOS:128-141, 114-127 and 100-113 (respective genomic, CpG island and amplicons, respectively) and/or sequences complementary thereto.

Thus, the present invention includes nucleic acid molecules (e.g., oligonucleotides and peptide nucleic acid (PNA) molecules (PNA-oligomers)) that hybridize under moderately stringent and/or stringent hybridization conditions to all or a portion of a sequence selected form the group consisting SEQ ID NOS:128-141, 114-127 and 100-113 (respective genomic, CpG island and amplicons, respectively), SEQ ID NOS:170-197, 226-253, 142-169 and 198-225 or to the complements thereof. Particularly preferred is a nucleic acid molecule that hybridizes under moderately stringent and/or stringent hybridization conditions to all or a portion of the sequences SEQ ID NOS:170-197, 226-253, 142-169 and 198-225 but not SEQ ID NOS:128-141, 114-127 and 100-113 (respective genomic, CpG island and amplicons, respectively) or other human genomic DNA.

The identical or hybridizing portion of the hybridizing nucleic acids is typically at least 9, 16, 20, 25, 30 or 35 nucleotides in length. However, longer molecules have inventive utility, and are thus within the scope of the present invention.

Preferably, the hybridizing portion of the inventive hybridizing nucleic acids is at least 95%, or at least 98%, or 100% identical to the sequence, or to a portion thereof of a sequence selected from the group consisting of SEQ ID NOS:128-141, 114-127 and 100-113 (respective genomic, CpG island and amplicons, respectively), SEQ ID NOS:170-197, 226-253, 142-169 and 198-225, or to the complements thereof.

Hybridizing nucleic acids of the type described herein can be used, for example, as a primer (e.g., a PCR primer), or a diagnostic and/or prognostic probe or primer. Preferably, hybridization of the oligonucleotide probe to a nucleic acid sample is performed under stringent conditions and the probe is 100% identical to the target sequence. Nucleic acid duplex or hybrid stability is expressed as the melting temperature or Tm, which is the temperature at which a probe dissociates from a target DNA. This melting temperature is used to define the required stringency conditions.

For target sequences that are related and substantially identical to the corresponding sequence of SEQ ID NOS:128-141, 114-127 and 100-113 (respective genomic, CpG island and amplicons, respectively) (such as allelic variants and SNPs), rather than identical, it is useful to first establish the lowest temperature at which only homologous hybridization occurs with a particular concentration of salt (e.g., SSC or SSPE). Then, assuming that 1% mismatching results in a 1° C. decrease in the Tm, the temperature of the final wash in the hybridization reaction is reduced accordingly (for example, if sequences having >95% identity with the probe are sought, the final wash temperature is decreased by 5° C.). In practice, the change in Tm can be between 0.5° C. and 1.5° C. per 1% mismatch.

Examples of inventive oligonucleotides of length X (in nucleotides), as indicated by polynucleotide positions with reference to, e.g., (NEUROG1 CpG Island; SEQ ID NO:124, include those corresponding to sets (sense and antisense sets) of consecutively overlapping oligonucleotides of length X, where the oligonucleotides within each consecutively overlapping set (corresponding to a given X value) are defined as the finite set of Z oligonucleotides from nucleotide positions:

n to (n+(X−1));

where n=1, 2, 3, . . . (Y−(X−1));

where Y equals the length (nucleotides or base pairs) of SEQ ID NO:124 (2,091);

where X equals the common length (in nucleotides) of each oligonucleotide in the set (e.g., X=20 for a set of consecutively overlapping 20-mers); and where the number (Z) of consecutively overlapping oligomers of length X for a given SEQ ID NO of length Y is equal to Y−(X−1). For example Z=2,091−19=2,072 for either sense or antisense sets of SEQ ID NO:124, where X=20.

Preferably, the set is limited to those oligomers that comprise at least one CpG, TpG or CpA dinucleotide.

Examples of inventive 20-mer oligonucleotides include the following set of 2,072 oligomers (and the antisense set complementary thereto), indicated by polynucleotide positions with reference to SEQ ID NO: 124:

1-20, 2-21, 3-22, 4-23, 5-24, . . . and 2,072-2,091.

Preferably, the set is limited to those oligomers that comprise at least one CpG, TpG or CpA dinucleotide.

Likewise, examples of inventive 25-mer oligonucleotides include the following set of 2,067 oligomers (and the antisense set complementary thereto), indicated by polynucleotide positions with reference to SEQ ID NO: 124:

1-25, 2-26, 3-27, 4-28, 5-29, . . . and 2,067-2,091.

Preferably, the set is limited to those oligomers that comprise at least one CpG, TpG or CpA dinucleotide.

The present invention encompasses, for each of SEQ ID NOS:128-141, 114-127 and 100-113 (respective genomic, CpG island and amplicons, respectively), SEQ ID NOS:170-197, 226-253, 142-169 and 198-225 (sense and antisense), multiple consecutively overlapping sets of oligonucleotides or modified oligonucleotides of length X, where, e.g., X=9, 10, 17, 20, 22, 23, 25, 27, 30 or 35 nucleotides.

The oligonucleotides or oligomers according to the present invention constitute effective tools useful to ascertain genetic and epigenetic parameters of the genomic sequences selected from the group consisting of SEQ ID NOS:128-141, 114-127 and 100-113 (respective genomic, CpG island and amplicons, respectively). Preferred sets of such oligonucleotides or modified oligonucleotides of length X are those consecutively overlapping sets of oligomers corresponding to SEQ ID NOS:128-141, 114-127 and 100-113 (respective genomic, CpG island and amplicons, respectively), SEQ ID NOS:170-197, 226-253, 142-169 and 198-225 (and to the complements thereof). Preferably, said oligomers comprise at least one CpG, TpG or CpA dinucleotide.

Particularly preferred oligonucleotides or oligomers according to the present invention are those in which the cytosine of the CpG dinucleotide (or of the corresponding converted TpG or CpA dinucleotide) sequences is within the middle third of the oligonucleotide; that is, where the oligonucleotide is, for example, 13 bases in length, the CpG, TpG or CpA dinucleotide is positioned within the fifth to ninth nucleotide from the 5′-end.

The oligonucleotides of the invention can also be modified by chemically linking the oligonucleotide to one or more moieties or conjugates to enhance the activity, stability or detection of the oligonucleotide. Such moieties or conjugates include chromophores, fluorophors, lipids such as cholesterol, cholic acid, thioether, aliphatic chains, phospholipids, polyamines, polyethylene glycol (PEG), palmityl moieties, and others as disclosed in, for example, U.S. Pat. Nos. 5,514,758, 5,565,552, 5,567,810, 5,574,142, 5,585,481, 5,587,371, 5,597,696 and 5,958,773. The probes may also exist in the form of a PNA (peptide nucleic acid) which has particularly preferred pairing properties. Thus, the oligonucleotide may include other appended groups such as peptides, and may include hybridization-triggered cleavage agents (Krol et al., *BioTechniques* 6:958-976, 1988) or intercalating agents (Zon, *Pharm. Res.* 5:539-549, 1988). To this end, the oligonucleotide may be conjugated to another molecule, e.g., a chromophore, fluorophor, peptide, hybridization-triggered cross-linking agent, transport agent, hybridization-triggered cleavage agent, etc.

The oligonucleotide may also comprise at least one art-recognized modified sugar and/or base moiety, or may comprise a modified backbone or non-natural internucleoside linkage.

The oligonucleotides or oligomers according to particular embodiments of the present invention are typically used in 'sets,' which contain at least one oligomer for analysis of each of the CpG dinucleotides of a genomic sequence selected from the group consisting of SEQ ID NOS:128-141, 114-127 and 100-113 (respective genomic, CpG island and amplicons, respectively) and sequences complementary thereto, or to the corresponding CpG, TpG or CpA dinucleotide within a sequence of the treated nucleic acids according to SEQ ID NOS:170-197, 226-253, 142-169 and 198-225 and sequences complementary thereto. However, it is anticipated that for economic or other factors it may be preferable to analyse a limited selection of the CpG dinucleotides within said sequences, and the content of the set of oligonucleotides is altered accordingly.

Therefore, in particular embodiments, the present invention provides a set of at least two (2) (oligonucleotides and/or PNA-oligomers) useful for detecting the cytosine methylation state in treated genomic DNA (SEQ ID NOS:170-197, 226-253, 142-169 and 198-225), or in genomic DNA (e.g., within SEQ ID NOS:128-141, 114-127 and 100-113 (respective genomic, CpG island and amplicons, respectively) and sequences complementary thereto). These probes enable diagnosis, classification and/or therapy of genetic and epigenetic parameters of liver and/or colorectal cell proliferative disorders. The set of oligomers may also be used for detecting single nucleotide polymorphisms (SNPs) in treated genomic DNA (SEQ ID NOS:170-197, 226-253, 142-169 and 198-225), or in genomic DNA (e.g., within SEQ ID NOS:128-141, 114-127 and 100-113 (respective genomic, CpG island and amplicons, respectively) and sequences complementary thereto).

In preferred embodiments, at least one, and more preferably all members of a set of oligonucleotides is bound to a solid phase.

In further embodiments, the present invention provides a set of at least two (2) oligonucleotides that are used as 'primer' oligonucleotides for amplifying DNA sequences of one of SEQ ID NOS:128-141, 114-127 and 100-113 (respective genomic, CpG island and amplicons, respectively), SEQ ID NOS:170-197, 226-253, 142-169 and 198-225 and sequences complementary thereto, or segments thereof.

It is anticipated that the oligonucleotides may constitute all or part of an "array" or "DNA chip" (i.e., an arrangement of different oligonucleotides and/or PNA-oligomers bound to a solid phase). Such an array of different oligonucleotide- and/or PNA-oligomer sequences can be characterized, for example, in that it is arranged on the solid phase in the form of a rectangular or hexagonal lattice. The solid-phase surface may be composed of silicon, glass, polystyrene, aluminium, steel, iron, copper, nickel, silver, or gold. Nitrocellulose as well as plastics such as nylon, which can exist in the form of pellets or also as resin matrices, may also be used. An overview of the Prior Art in oligomer array manufacturing can be gathered from a special edition of Nature Genetics (*Nature Genetics Supplement*, Volume 21, January 1999, and from the literature cited therein). Fluorescently labelled probes are often used for the scanning of immobilized DNA arrays. The simple attachment of Cy3 and Cy5 dyes to the 5'-OH of the specific probe are particularly suitable for fluorescence labels. The detection of the fluorescence of the hybridised probes may be carried out, for example, via a confocal microscope. Cy3 and Cy5 dyes, besides many others, are commercially available.

It is also anticipated that the oligonucleotides, or particular sequences thereof, may constitute all or part of an "virtual array" wherein the oligonucleotides, or particular sequences thereof, are used, for example, as 'specifiers' as part of, or in combination with a diverse population of unique labeled probes to analyze a complex mixture of analytes. Such a method, for example is described in US 2003/0013091 (U.S. Ser. No. 09/898,743, published 16 Jan. 2003). In such methods, enough labels are generated so that each nucleic acid in the complex mixture (i.e., each analyte) can be uniquely bound by a unique label and thus detected (each label is directly counted, resulting in a digital read-out of each molecular species in the mixture).

It is particularly preferred that the oligomers according to the invention are utilised for at least one of: determining and/or classifying CIMP status in colorectal cancers; identifying KRAS mutant, BRAF wildtype tumors; determining the relationship between CIMP status and other molecular features of the cancers including, but not limited to BRAF mutation, KRAS mutation and MSI status; determining the relationship between CIMP status and other variables including, but not limited to age, sex, tumor location, family history, race, country of origin, tumor characteristics (including, tumor type, tumor grade, invasive margin characteristics, lymphocyte infiltration characteristics, direct spread, lymph node spread, venous spread and type of residual adjacent polyp, if present); determining, between subgroups defined by CIMP status and BRAF mutations, effects of selected risk factors including, but not limited to body mass index, smoking history, alcohol intake, dietary folate intake, folate metabolic enzyme polymorphisms and history of hormonal use; and providing a foundation for a population-based study of CIMP, by providing a novel panel of carefully selected methylation markers representing the CIMP subgroup, and having utility to classify CIMP In particular aspects, this is enabled by use of said sets for the detection or detection and differentiation of one or more of the following classes of tissues: colorectal carcinoma, colon adenoma, inflammatory colon tissue, grade 2 dysplasia colon adenomas less than 1 cm, grade 3 dysplasia colon adenomas larger than 1 cm, normal colon tissue, non-colon healthy tissue and non-colon cancer tissue.

Particularly preferred are those sets of oligomers according to the Examples.

In the most preferred embodiment of the method, CIMP status is determined or classified. This is achieved by analysis of the methylation status of at least one target sequence comprising at least one CpG position said sequence comprising, or hybridizing under stringent conditions to at least 16 contiguous nucleotides of a sequence selected from the group consisting of SEQ ID NOS:128-141, 114-127 and 100-113 (respective genomic, CpG island and amplicons, respectively) and complements thereof. The present invention further provides a method for ascertaining genetic and/or epigenetic parameters of the genomic sequence according to SEQ ID NOS:128-141, 114-127 and 100-113 (respective genomic, CpG island and amplicons, respectively) within a subject by analysing cytosine methylation and single nucleotide polymorphisms. Said method comprising contacting a nucleic acid comprising e.g., within SEQ ID NOS:128-141, 114-127 and 100-113 (respective genomic, CpG island and amplicons, respectively) in a biological sample obtained from said subject with at least one reagent or a series of reagents, wherein said reagent or series of reagents, distinguishes between methylated and non-methylated CpG dinucleotides within the target nucleic acid.

In a preferred embodiment, said method comprises the following steps: In the first step, a sample of the tissue to be analysed is obtained. The source may be any suitable source, such as cell lines, histological slides, biopsies, paraffin-embedded tissue, body fluids, stool, colonic effluent, urine, blood plasma, blood serum, whole blood, isolated blood cells, cells isolated from the blood and all possible combinations thereof. It is preferred that said sources of DNA are stool or body fluids selected from the group consisting colonic effluent, urine, blood plasma, blood serum, whole blood, isolated blood cells, cells isolated from the blood.

The genomic DNA is then isolated from the sample. Genomic DNA may be isolated by any means standard in the art, including the use of commercially available kits. Briefly, wherein the DNA of interest is encapsulated in by a cellular membrane the biological sample must be disrupted and lysed by enzymatic, chemical or mechanical means. The DNA solution may then be cleared of proteins and other contaminants e.g. by digestion with proteinase K. The genomic DNA is then recovered from the solution. This may be carried out by means of a variety of methods including salting out, organic extraction or binding of the DNA to a solid phase support. The choice of method will be affected by several factors including time, expense and required quantity of DNA.

Wherein the sample DNA is not enclosed in a membrane (e.g. circulating DNA from a blood sample) methods standard in the art for the isolation and/or purification of DNA may be employed. Such methods include the use of a protein degenerating reagent e.g., chaotropic salt e.g. guanidine hydrochloride or urea; or a detergent e.g. sodium dodecyl sulphate (SDS), cyanogen bromide. Alternative methods include but are not limited to ethanol precipitation or propanol precipitation, vacuum concentration amongst others by means of a centrifuge. The person skilled in the art may also make use of devices such as filter devices, e.g., ultrafiltration, silica surfaces or membranes, magnetic particles, polystyrol particles, polystyrol surfaces, positively charged surfaces, and positively charged membranes, charged membranes, charged surfaces, charged switch membranes, charged switched surfaces.

Once the nucleic acids have been extracted, the genomic double stranded DNA is used in the analysis.

In the second step of the method, the genomic DNA sample is treated in such a manner that cytosine bases which are unmethylated at the 5'-position are converted to uracil, thymine, or another base which is dissimilar to cytosine in terms of hybridisation behaviour. This will be understood as 'pretreatment' or 'treatment' herein.

This is preferably achieved by means of treatment with a bisulfite reagent. The term "bisulfite reagent" refers to a reagent comprising bisulfite, disulfite, hydrogen sulfite or combinations thereof, useful as disclosed herein to distinguish between methylated and unmethylated CpG dinucleotide sequences. Methods of said treatment are known in the art (e.g., PCT/EP2004/011715, which is incorporated by reference in its entirety). It is preferred that the bisulfite treatment is conducted in the presence of denaturing solvents such as but not limited to n-alkylenglycol, particularly diethylene glycol dimethyl ether (DME), or in the presence of dioxane or dioxane derivatives. In a preferred embodiment the denaturing solvents are used in concentrations between 1% and 35% (v/v). It is also preferred that the bisulfite reaction is carried out in the presence of scavengers such as but not limited to chromane derivatives, e.g., 6-hydroxy-2, 5,7,8,-tetramethylchromane 2-carboxylic acid or trihydroxybenzoe acid and derivates thereof, e.g., Gallic acid (see: PCT/EP2004/011715 which is incorporated by reference in its entirety). The bisulfite conversion is preferably carried out at a reaction temperature between 30° C. and 70° C., whereby the temperature is increased to over 85° C. for short periods of times during the reaction (see: PCT/EP2004/011715 which is incorporated by reference in its entirety). The bisulfite treated DNA is preferably purified priori to the quantification. This may be conducted by any means known in the art, such as but not limited to ultrafiltration, preferably carried out by means of Microcon™ columns (manufactured by Millipore™). The purification is carried out according to a modified manufacturer's protocol (see: PCT/EP2004/011715 which is incorporated by reference in its entirety).

In the third step of the method, fragments of the treated DNA are amplified, using sets of primer oligonucleotides according to the present invention, and an amplification enzyme. The amplification of several DNA segments can be carried out simultaneously in one and the same reaction vessel. Typically, the amplification is carried out using a polymerase chain reaction (PCR). Preferably said amplificates are 100 to 2,000 base pairs in length. The set of primer oligonucleotides includes at least two oligonucleotides whose sequences are each reverse complementary, identical, or hybridise under stringent or highly stringent conditions to an at least 16-base-pair long segment of the base sequences of one of SEQ ID NOS:170-197, 226-253, 142-169 and 198-225 and sequences complementary thereto.

In an alternate embodiment of the method, the methylation status of pre-selected CpG positions within at least one nucleic acid sequences selected from the group consisting of SEQ ID NOS:128-141, 114-127 and 100-113 (respective genomic, CpG island and amplicons, respectively) may be detected by use of methylation-specific primer oligonucleotides. This technique (MSP) has been described in U.S. Pat. No. 6,265,171 to Herman. The use of methylation status specific primers for the amplification of bisulfite treated DNA allows the differentiation between methylated and unmethylated nucleic acids. MSP primers pairs contain at least one primer which hybridises to a bisulfite treated CpG dinucleotide. Therefore, the sequence of said primers comprises at least one CpG dinucleotide. MSP primers specific for non-methylated DNA contain a "T" at the position of the C position in the CpG. Preferably, therefore, the base sequence of said primers is required to comprise a sequence having a length of at least 9 nucleotides which hybridises to a treated nucleic acid sequence according to one of SEQ ID NOS:170-197, 226-253, 142-169 and 198-225 and sequences complementary thereto, wherein the base sequence of said oligomers comprises at least one CpG dinucleotide. A further preferred embodiment of the method comprises the use of blocker oligonucleotides (the HeavyMethyl™ assay). The use of such blocker oligonucleotides has been described by Yu et al., *BioTechniques* 23:714-720, 1997. Blocking probe oligonucleotides are hybridised to the bisulfite treated nucleic acid concurrently with the PCR primers. PCR amplification of the nucleic acid is terminated at the 5' position of the blocking probe, such that amplification of a nucleic acid is suppressed where the complementary sequence to the blocking probe is present. The probes may be designed to hybridize to the bisulfite treated nucleic acid in a methylation status specific manner. For example, for detection of methylated nucleic acids within a population of unmethylated nucleic acids, suppression of the amplification of nucleic acids which are unmethylated at the position in question would be carried out by the use of blocking probes comprising a 'CpA' or 'TpA' at the position in question, as opposed to a 'CpG' if the suppression of amplification of methylated nucleic acids is desired.

For PCR methods using blocker oligonucleotides, efficient disruption of polymerase-mediated amplification requires that blocker oligonucleotides not be elongated by the polymerase. Preferably, this is achieved through the use of blockers that are 3'-deoxyoligonucleotides, or oligonucleotides derivitized at the 3' position with other than a "free" hydroxyl group. For example, 3'-O-acetyl oligonucleotides are representative of a preferred class of blocker molecule.

Additionally, polymerase-mediated decomposition of the blocker oligonucleotides should be precluded. Preferably, such preclusion comprises either use of a polymerase lacking 5'-3' exonuclease activity, or use of modified blocker oligonucleotides having, for example, thioate bridges at the 5'-terminii thereof that render the blocker molecule nuclease-resistant. Particular applications may not require such 5' modifications of the blocker. For example, if the blocker- and primer-binding sites overlap, thereby precluding binding of the primer (e.g., with excess blocker), degradation of the blocker oligonucleotide will be substantially precluded. This is because the polymerase will not extend the primer toward, and through (in the 5'-3' direction) the blocker—a process that normally results in degradation of the hybridized blocker oligonucleotide.

A particularly preferred blocker/PCR embodiment, for purposes of the present invention and as implemented herein, comprises the use of peptide nucleic acid (PNA) oligomers as blocking oligonucleotides. Such PNA blocker oligomers are ideally suited, because they are neither decomposed nor extended by the polymerase.

Preferably, therefore, the base sequence of said blocking oligonucleotides is required to comprise a sequence having a length of at least 9 nucleotides which hybridises to a treated nucleic acid sequence according to one of SEQ ID NOS:170-197, 226-253, 142-169 and 198-225 and sequences complementary thereto, wherein the base sequence of said oligonucleotides comprises at least one CpG, TpG or CpA dinucleotide.

The fragments obtained by means of the amplification can carry a directly or indirectly detectable label. Preferred are labels in the form of fluorescence labels, radionuclides, or detachable molecule fragments having a typical mass which can be detected in a mass spectrometer. Where said labels are mass labels, it is preferred that the labelled amplificates have a single positive or negative net charge, allowing for better delectability in the mass spectrometer. The detection may be carried out and visualized by means of, e.g., matrix assisted laser desorption/ionization mass spectrometry (MALDI) or using electron spray mass spectrometry (ESI).

Matrix Assisted Laser Desorption/Ionization Mass Spectrometry (MALDI-TOF) is a very efficient development for the analysis of biomolecules (Karas & Hillenkamp, *Anal Chem.*, 60:2299-301, 1988). An analyte is embedded in a light-absorbing matrix. The matrix is evaporated by a short laser pulse thus transporting the analyte molecule into the vapor phase in an unfragmented manner. The analyte is ionized by collisions with matrix molecules. An applied voltage accelerates the ions into a field-free flight tube. Due to their different masses, the ions are accelerated at different rates. Smaller ions reach the detector sooner than bigger ones. MALDI-TOF spectrometry is well suited to the analysis of peptides and proteins. The analysis of nucleic acids is somewhat more difficult (Gut & Beck, *Current Innovations and Future Trends,* 1:147-57, 1995). The sensitivity with respect to nucleic acid analysis is approximately 100-times less than for peptides, and decreases disproportionally with increasing fragment size. Moreover, for nucleic acids having a multiply negatively charged backbone, the ionization process via the matrix is considerably less efficient. In MALDI-TOF spectrometry, the selection of the matrix plays an eminently important role. For desorption of peptides, several very efficient matrixes have been found which produce a very fine crystallisation. There are now several responsive matrixes for DNA, however, the difference in sensitivity between peptides and nucleic acids has not been reduced. This difference in sensitivity can be reduced, however, by chemically modifying the DNA in such a manner that it becomes more similar to a peptide. For example, phosphorothioate nucleic acids, in which the usual phosphates of the backbone are substituted with thiophosphates, can be converted into a charge-neutral DNA using simple alkylation chemistry (Gut & Beck, *Nucleic Acids Res.* 23: 1367-73, 1995). The coupling of a charge tag to this modified DNA results in an increase in MALDI-TOF sensitivity to the same level as that found for peptides. A further advantage of charge tagging is the increased stability of the analysis against impurities, which makes the detection of unmodified substrates considerably more difficult.

In the fourth step of the method, the amplificates obtained during the third step of the method are analysed in order to ascertain the methylation status of the CpG dinucleotides prior to the treatment.

In embodiments where the amplificates were obtained by means of MSP amplification, the presence or absence of an amplificate is in itself indicative of the methylation state of the CpG positions covered by the primer, according to the base sequences of said primer.

Amplificates obtained by means of both standard and methylation specific PCR may be further analysed by means of based-based methods such as, but not limited to, array technology and probe based technologies as well as by means of techniques such as sequencing and template directed extension.

In one embodiment of the method, the amplificates synthesised in step three are subsequently hybridized to an array or a set of oligonucleotides and/or PNA probes. In this context, the hybridization takes place in the following manner: the set of probes used during the hybridization is preferably composed of at least 2 oligonucleotides or PNA-oligomers; in the process, the amplificates serve as probes which hybridize to oligonucleotides previously bonded to a solid phase; the non-hybridized fragments are subsequently removed; said oligonucleotides contain at least one base sequence having a length of at least 9 nucleotides which is reverse complementary or identical to a segment of the base sequences specified in the present Sequence Listing; and the segment comprises at least one CpG, TpG or CpA dinucleotide. The hybridizing portion of the hybridizing nucleic acids is typically at least 9, 15, 20, 25, 30 or 35 nucleotides in length. However, longer molecules have inventive utility, and are thus within the scope of the present invention.

In a preferred embodiment, said dinucleotide is present in the central third of the oligomer. For example, wherein the oligomer comprises one CpG dinucleotide, said dinucleotide is preferably the fifth to ninth nucleotide from the 5'-end of a 13-mer. One oligonucleotide exists for the analysis of each CpG dinucleotide within a sequence selected from the group consisting of SEQ ID NOS:128-141, 114-127 and 100-113 (respective genomic, CpG island and amplicons, respectively), and the equivalent positions within SEQ ID NOS: 170-197, 226-253, 142-169 and 198-225.

Said oligonucleotides may also be present in the form of peptide nucleic acids. The non-hybridised amplificates are then removed. The hybridised amplificates are then detected. In this context, it is preferred that labels attached to the amplificates are identifiable at each position of the solid phase at which an oligonucleotide sequence is located.

In yet a further embodiment of the method, the genomic methylation status of the CpG positions may be ascertained by means of oligonucleotide probes (as detailed above) that are hybridised to the bisulfite treated DNA concurrently with the PCR amplification primers (wherein said primers may either be methylation specific or standard).

A particularly preferred embodiment of this method is the use of fluorescence-based Real Time Quantitative PCR (Heid et al., *Genome Res.* 6:986-994, 1996; also see U.S. Pat. No. 6,331,393) employing a dual-labelled fluorescent oligonucleotide probe (TaqMan™ PCR, using an ABI Prism 7700 Sequence Detection System, Perkin Elmer Applied Biosystems, Foster City, Calif.). The TaqMan™ PCR reaction employs the use of a non-extendible interrogating oligonucleotide, called a TaqMan™ probe, which, in preferred embodiments, is designed to hybridise to a CpG-rich sequence located between the forward and reverse amplification primers. The TaqMan™ probe further comprises a fluorescent "reporter moiety" and a "quencher moiety" covalently bound to linker moieties (e.g., phosphoramidites) attached to the nucleotides of the TaqMan™ oligonucleotide. For analysis of methylation within nucleic acids subsequent to bisulfite treatment, it is required that the probe be methylation specific, as described in U.S. Pat. No. 6,331,393, (hereby incorporated by reference in its entirety) also known as the MethyLight™ assay. Variations on the TaqMan™ detection methodology that are also suitable for use with the described invention include the use of dual-probe technology (Lightcycler™) or fluorescent amplification primers (Sunrise™ technology). Both these techniques may be adapted in a manner suitable for use with bisulfite treated DNA, and moreover for methylation analysis within CpG dinucleotides.

In a further preferred embodiment of the method, the fourth step of the method comprises the use of template-directed oligonucleotide extension, such as MS-SNuPE as described by Gonzalgo & Jones, *Nucleic Acids Res.* 25:2529-2531, 1997.

In yet a further embodiment of the method, the fourth step of the method comprises sequencing and subsequent sequence analysis of the amplificate generated in the third step of the method (Sanger F., et al., *Proc Natl Acad Sci USA* 74:5463-5467, 1977).

Best Mode

In a preferred embodiment of the method, the genomic nucleic acids are isolated and treated according to the first three steps of the method outlined above, namely:

a) obtaining, from a subject, a biological sample having subject genomic DNA;

b) extracting or otherwise isolating the genomic DNA;

c) treating the genomic DNA of b), or a fragment thereof, with one or more reagents to convert cytosine bases that are unmethylated in the 5-position thereof to uracil or to another base that is detectably dissimilar to cytosine in terms of hybridization properties; and wherein d) amplifying subsequent to treatment in c) is carried out in a methylation specific manner, namely by use of methylation specific primers or blocking oligonucleotides, and further wherein e) detecting of the amplificates is carried out by means of a real-time detection probe, as described above.

Preferably, where the subsequent amplification of d) is carried out by means of methylation specific primers, as described above, said methylation specific primers comprise a sequence having a length of at least 9 nucleotides which hybridises to a treated nucleic acid sequence according to one of SEQ ID NOS:170-197, 226-253, 142-169 and 198-225 and sequences complementary thereto, wherein the base sequence of said oligomers comprise at least one CpG dinucleotide.

Step e) of the method, namely the detection of the specific amplificates indicative of the methylation status of one or more CpG positions of at least one sequences of the group comprising SEQ ID NOS:128-141, 114-127 and 100-113 is carried out by means of real-time detection methods as described above.

Additional embodiments of the invention provide a method for the analysis of the methylation status of genomic DNA according to the invention (e.g., within SEQ ID NOS:128-141, 114-127 and 100-113 (respective genomic, CpG island and amplicons, respectively), and complements thereof) without the need for bisulfite conversion. Methods are known in the art wherein a methylation sensitive restriction enzyme reagent, or a series of restriction enzyme reagents comprising methylation sensitive restriction enzyme reagents that distinguishes between methylated and non-methylated CpG dinucleotides within a target region are utilized in determining methylation, for example but not limited to DMH.

In the first step of such additional embodiments, the genomic DNA sample is isolated from tissue or cellular sources. Genomic DNA may be isolated by any means standard in the art, including the use of commercially available kits. Briefly, wherein the DNA of interest is encapsulated in by a cellular membrane the biological sample must be disrupted and lysed by enzymatic, chemical or mechanical means. The DNA solution may then be cleared of proteins and other contaminants, e.g., by digestion with proteinase K. The genomic DNA is then recovered from the solution. This may be carried out by means of a variety of methods including salting out, organic extraction or binding of the DNA to a solid phase support. The choice of method will be affected by several factors including time, expense and required quantity of DNA. All clinical sample types comprising neoplastic or potentially neoplastic matter are suitable for use in the present method, preferred are cell lines, histological slides, biopsies, paraffin-embedded tissue, body fluids, stool, colonic effluent, urine, blood plasma, blood serum, whole blood, isolated blood cells, cells isolated from the blood and combinations thereof. Body fluids are the preferred source of the DNA; particularly preferred are blood plasma, blood serum, whole blood, isolated blood cells and cells isolated from the blood.

Once the nucleic acids have been extracted, the genomic double-stranded DNA is used in the analysis.

In a preferred embodiment, the DNA may be cleaved prior to treatment with methylation sensitive restriction enzymes. Such methods are known in the art and may include both physical and enzymatic means. Particularly preferred is the use of one or a plurality of restriction enzymes which are not methylation sensitive, and whose recognition sites are AT rich and do not comprise CG dinucleotides. The use of such enzymes enables the conservation of CpG islands and CpG rich regions in the fragmented DNA. The non-methylation-specific restriction enzymes are preferably selected from the group consisting of MseI, BfaI, Csp6I, Tru1I, Tvu1I, Tru9I, Tvu9I, MaeI and XspI. Particularly preferred is the use of two or three such enzymes. Particularly preferred is the use of a combination of MseI, BfaI and Csp6I.

The fragmented DNA may then be ligated to adaptor oligonucleotides in order to facilitate subsequent enzymatic amplification. The ligation of oligonucleotides to blunt and sticky ended DNA fragments is known in the art, and is carried out by means of dephosphorylation of the ends (e.g., using calf or shrimp alkaline phosphatase) and subsequent ligation using ligase enzymes (e.g., T4 DNA ligase) in the presence of dATPs. The adaptor oligonucleotides are typically at least 18 base pairs in length.

In the third step, the DNA (or fragments thereof) is then digested with one or more methylation sensitive restriction enzymes. The digestion is carried out such that hydrolysis of the DNA at the restriction site is informative of the methylation status of a specific CpG dinucleotide of at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively).

Preferably, the methylation-specific restriction enzyme is selected from the group consisting of Bsi E1, Hga I HinPI, Hpy99I, Ava I, Bce AI, Bsa HI, BisI, BstUI, BshI236I, AccII, BstFNI, McrBC, GlaI, MvnI, HpaII (HapII), HapII, AciI, SmaI, HinPII, HpyCH4IV, EagI and mixtures of two or more of the above enzymes. Preferred is a mixture containing the restriction enzymes BstUI, HpaII, HpyCH4IV and HinP1I.

In the fourth step, which is optional but a preferred embodiment, the restriction fragments are amplified. This is preferably carried out using a polymerase chain reaction, and said amplificates may carry suitable detectable labels as discussed above, namely fluorophore labels, radionuclides and mass labels. Particularly preferred is amplification by means of an amplification enzyme and at least two primers comprising, in each case a contiguous sequence at least 16 nucleotides in length that is complementary to, or hybridizes under moderately stringent or stringent conditions to a sequence selected from the group consisting of SEQ ID NOS:128-141, 114-127 and 100-113 (respective genomic, CpG island and amplicons, respectively), and complements thereof. Preferably said contiguous sequence is at least 16, 20 or 25 nucleotides in length. In an alternative embodiment said primers may be complementary to any adaptors linked to the fragments.

In the fifth step the amplificates are detected. The detection may be by any means standard in the art, for example, but not limited to, gel electrophoresis analysis, hybridisation analysis, incorporation of detectable tags within the PCR products, DNA array analysis, MALDI or ESI analysis. Preferably said detection is carried out by hybridisation to at least one nucleic acid or peptide nucleic acid comprising in each case a contiguous sequence at least 16 nucleotides in length that is complementary to, or hybridizes under moderately stringent or stringent conditions to a sequence selected from the group consisting of SEQ ID NOS:128-141, 114-127 and 100-113 (respective genomic, CpG island and amplicons, respectively), and complements thereof. Preferably said contiguous sequence is at least 16, 20 or 25 nucleotides in length.

Subsequent to the determination of the methylation state or level of the genomic nucleic acids the presence, absence or class of CIMP and/or cellular proliferative disorder (e.g., colon cancer) is deduced based upon the methylation state or level of at least one CpG dinucleotide sequence of at least one sequence selected from the group consisting of SEQ ID NOS:128-141, 114-127 and 100-113 (respective genomic, CpG island and amplicons, respectively), or an average, or a value reflecting an average methylation state of a plurality of CpG dinucleotide sequences of at least one sequence selected from the group consisting of SEQ ID NOS:128-141, 114-127 and 100-113 (respective genomic, CpG island and amplicons, respectively) wherein methylation is associated with CIMP and/or cellular proliferative disorder (e.g., colon cancer). Wherein said methylation is determined by quantitative means the cut-off point for determining said the presence of methylation is preferably zero (i.e. wherein a sample displays any degree of methylation it is determined as having a methylated status at the analysed CpG position). Nonetheless, it is foreseen that the person skilled in the art may wish to adjust said cut-off value in order to provide an assay of a particularly preferred sensitivity or specificity. Accordingly said cut-off value may be increased (thus increasing the specificity), said cut off value may be within a range selected form the group consisting of 0%-5%, 5%-10%, 10%-15%, 15%-20%, 20%-30% and 30%-50%. Particularly preferred are the cut-offs 10%, 15%, 25%, and 30%.

In an alternative embodiment of the method wherein a panel of genes comprising BCL2, BDNF, CACNA1G, CALCA, CRABP1, DLEC1, GATA3, HOXA1, IGF2, KL, NEUROG1, NR3C1, RUNX3, SOCS1 (Table 6), subsequent to the determination of the methylation state of the genomic nucleic acids the presence, absence or subclass of CIMP and/or colon proliferative disorders, in particular colorectal cell proliferative disorder is deduced based upon the methylation state of at least one CpG dinucleotide sequence of SEQ ID NOS:128-141, 114-127 and 100-113 (respective genomic, CpG island and amplicons, respectively), or an average, or a value reflecting an average methylation state of a plurality of CpG dinucleotide sequences thereof wherein hypermethylation is associated with CIMP and/or colorectal cancer.

Diagnostic and Prognostic Assays for CIMP and/or Cellular Proliferative Disorders The present invention enables diagnosis of events which are disadvantageous to patients or individuals in which important genetic and/or epigenetic parameters within at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively) may be used as markers. Said parameters obtained by means of the present invention may be compared to another set of genetic and/or epigenetic parameters, the differences serving as the basis for a diagnosis and/or prognosis of events which are disadvantageous to patients or individuals.

More specifically the present invention enables the screening of at-risk populations for the early detection of cancers, most preferably CIMP and/or colorectal carcinomas. Furthermore, in certain aspects, the present invention enables the differentiation of neoplastic (e.g. malignant) from benign (i.e. non-cancerous) cellular proliferative disorders. For example, in certain embodiments, it enables the differentiation of a colorectal carcinoma from small colon adenomas or polyps. Neoplastic cellular proliferative disorders present decreased methylation (i.e. decreased expression) within at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively), as opposed to said benign disorders which do not.

Specifically, the present invention provides for diagnostic and classification CIMP and/or cancer assays based on measurement of differential expression (preferably methylation) of one or more CpG dinucleotide sequences of at least one sequence selected from the group consisting of SEQ ID NOS:128-141, 114-127 and 100-113 (respective genomic, CpG island and amplicons, respectively) that comprise such a CpG dinucleotide sequence. Typically, such assays involve obtaining a sample from a subject, performing an assay to measure the expression of at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively), preferably by determining the methylation status of at least one sequence selected from the group consisting of SEQ ID NOS:128-141, 114-127 and 100-113 (respective genomic, CpG island and amplicons, respectively), derived from the sample, relative to a control sample, or a known standard and making a diagnosis based thereon.

In particular preferred embodiments, inventive oligomers are used to assess the CpG dinucleotide methylation status, such as those based on SEQ ID NOS:128-141, 114-127 and 100-113 (respective genomic, CpG island and amplicons, respectively), SEQ ID NOS:170-197, 226-253, 142-169 and 198-225 or arrays thereof, as well as in kits based thereon and useful for the diagnosis and/or classification of cellular proliferative disorders.

Kits

Moreover, an additional aspect of the present invention is a kit comprising: a means for determining methylation of at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively). The means for determining methylation comprise preferably a bisulfite-containing reagent; one or a plurality of oligonucleotides consisting whose sequences in each case are identical, are complementary, or hybridise under stringent or highly stringent conditions to a 9 or more preferably 18 base long segment of a sequence selected from SEQ ID NOS:170-197, 226-253, 142-169 and 198-225; and optionally instructions for carrying out and evaluating the described method of methylation analysis. In one embodiment the base sequence of said oligonucleotides comprises at least one CpG, CpA or TpG dinucleotide.

In a further embodiment, said kit may further comprise standard reagents for performing a CpG position-specific methylation analysis, wherein said analysis comprises one or more of the following techniques: MS-SNuPE, MSP, MethyLight™, HeavyMethyl, COBRA, and nucleic acid sequencing. However, a kit along the lines of the present invention can also contain only part of the aforementioned components.

In a preferred embodiment the kit may comprise additional bisulfite conversion reagents selected from the group consisting: DNA denaturation buffer; sulfonation buffer; DNA recovery reagents or kits (e.g., precipitation, ultrafiltration, affinity column); desulfonation buffer; and DNA recovery components.

In a further alternative embodiment, the kit may contain, packaged in separate containers, a polymerase and a reaction buffer optimised for primer extension mediated by the polymerase, such as PCR. In another embodiment of the invention the kit further comprising means for obtaining a biological sample of the patient. Preferred is a kit, which further comprises a container suitable for containing the means for determining methylation of at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively) in the biological sample of the patient, and most preferably further comprises instructions for use and interpretation of the kit results. In a preferred embodiment the kit comprises: (a) a bisulfite reagent; (b) a container suitable for containing the said bisulfite reagent and the biological sample of the patient; (c) at least one set of primer oligonucleotides containing two oligonucleotides whose sequences in each case are identical, are complementary, or hybridise under stringent or highly stringent conditions to a 9 or more preferably 18 base long segment of a sequence selected from SEQ ID NOS:170-197, 226-253, 142-169 and 198-225; and optionally (d) instructions for use and interpretation of the kit results. In an alternative preferred embodiment the kit comprises: (a) a bisulfite reagent; (b) a container suitable for containing the said bisulfite reagent and the biological sample of the patient; (c) at least one oligonucleotides and/or PNA-oligomer having a length of at least 9 or 16 nucleotides which is identical to or hybridises to a pre-treated nucleic acid sequence according to one of SEQ ID NOS:170-197, 226-253, 142-169 and 198-225 and sequences complementary thereto; and optionally (d) instructions for use and interpretation of the kit results.

In an alternative embodiment the kit comprises: (a) a bisulfite reagent; (b) a container suitable for containing the said bisulfite reagent and the biological sample of the patient; (c) at least one set of primer oligonucleotides containing two oligonucleotides whose sequences in each case are identical, are complementary, or hybridise under stringent or highly stringent conditions to a 9 or more preferably 18 base long segment of a sequence selected from SEQ ID NOS:170-197, 226-253, 142-169 and 198-225; (d) at least one oligonucleotides and/or PNA-oligomer having a length of at least 9 or 16 nucleotides which is identical to or hybridises to a pre-treated nucleic acid sequence according to one of SEQ ID NOS:170-197, 226-253, 142-169 and 198-225 and sequences complementary thereto; and optionally (e) instructions for use and interpretation of the kit results.

The kit may also contain other components such as buffers or solutions suitable for blocking, washing or coating, packaged in a separate container.

Typical reagents (e.g., as might be found in a typical COBRA™-based kit) for COBRA™ analysis may include, but are not limited to: PCR primers for at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively); restriction enzyme and appropriate buffer; gene-hybridization oligo; control hybridization oligo; kinase labeling kit for oligo probe; and labeled nucleotides. Typical reagents (e.g., as might be found in a typical MethyLight™-based kit) for MethyLight™ analysis may include, but are not limited to: PCR primers for the bisulfite converted sequence of at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively); bisulfite specific probes (e.g., TaqMan™ or Lightcycler™); optimized PCR buffers and deoxynucleotides; and Taq polymerase.

Typical reagents (e.g., as might be found in a typical Ms-SNuPE™-based kit) for Ms-SNuPE™ analysis may include, but are not limited to: PCR primers for specific gene (or bisulfite treated DNA sequence or CpG island); optimized PCR buffers and deoxynucleotides; gel extraction kit; positive control primers; Ms-SNuPE™ primers for the bisulfite converted sequence of at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively); reaction buffer (for the Ms-SNuPE reaction); and labelled nucleotides.

Typical reagents (e.g., as might be found in a typical MSP-based kit) for MSP analysis may include, but are not limited to: methylated and unmethylated PCR primers for the bisulfite converted sequence of or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively), optimized PCR buffers and deoxynucleotides, and specific probes.

Moreover, an additional aspect of the present invention is an alternative kit comprising a means for determining methylation of at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively), wherein said means comprise preferably at least one methylation specific restriction enzyme; one or a plurality of primer oligonucleotides (preferably one or a plurality of primer pairs) suitable for the amplification of a sequence comprising at least one CpG dinucleotide of a sequence selected from SEQ ID NOS:128-141, 114-127 and 100-113 (respective genomic, CpG island and amplicons, respectively); and optionally instructions for carrying out and evaluating the described method of methylation analysis. In one embodiment the base sequence of said oligonucleotides are identical, are complementary, or hybridise under stringent or highly stringent conditions to an at least 18 base long segment of a sequence selected from SEQ ID NOS:128-141, 114-127 and 100-113 (respective genomic, CpG island and amplicons, respectively).

In a further embodiment said kit may comprise one or a plurality of oligonucleotide probes for the analysis of the digest fragments, preferably said oligonucleotides are identical, are complementary, or hybridise under stringent or highly stringent conditions to an at least 16 base long segment of a sequence selected from SEQ ID NOS:128-141, 114-127 and 100-113 (respective genomic, CpG island and amplicons, respectively).

In a preferred embodiment the kit may comprise additional reagents selected from the group consisting: buffer (e.g., restriction enzyme, PCR, storage or washing buffers); DNA recovery reagents or kits (e.g., precipitation, ultrafiltration, affinity column) and DNA recovery components.

In a further alternative embodiment, the kit may contain, packaged in separate containers, a polymerase and a reaction buffer optimised for primer extension mediated by the polymerase, such as PCR. In another embodiment of the invention the kit further comprising means for obtaining a biological sample of the patient. In a preferred embodiment the kit comprises: (a) a methylation sensitive restriction enzyme reagent; (b) a container suitable for containing the said reagent and the biological sample of the patient; (c) at least one set of oligonucleotides one or a plurality of nucleic acids or peptide nucleic acids which are identical, are complementary, or hybridise under stringent or highly stringent conditions to an at least 9 base long segment of a sequence selected from SEQ ID NOS:128-141, 114-127 and 100-113 (respective genomic, CpG island and amplicons, respectively); and optionally (d) instructions for use and interpretation of the kit results.

In an alternative preferred embodiment the kit comprises: (a) a methylation sensitive restriction enzyme reagent; (b) a container suitable for containing the said reagent and the biological sample of the patient; (c) at least one set of primer oligonucleotides suitable for the amplification of a sequence comprising at least one CpG dinucleotide of a sequence selected from SEQ ID NOS:128-141, 114-127 and 100-113 (respective genomic, CpG island and amplicons, respectively); and optionally (d) instructions for use and interpretation of the kit results.

In an alternative embodiment the kit comprises: (a) a methylation sensitive restriction enzyme reagent; (b) a container suitable for containing the said reagent and the biological sample of the patient; (c) at least one set of primer oligonucleotides suitable for the amplification of a sequence comprising at least one CpG dinucleotide of a sequence selected from SEQ ID NOS:128-141, 114-127 and 100-113 (respective genomic, CpG island and amplicons, respectively); (d) at least one set of oligonucleotides one or a plurality of nucleic acids or peptide nucleic acids which are identical, are complementary, or hybridise under stringent or highly stringent conditions to an at least 9 base long segment of a sequence selected from SEQ ID NOS:128-141, 114-127 and 100-113 (respective genomic, CpG island and amplicons, respectively) and optionally (e) instructions for use and interpretation of the kit results.

The kit may also contain other components such as buffers or solutions suitable for blocking, washing or coating, packaged in a separate container.

The invention further relates to a kit for use in providing a diagnosis of the presence of a cell proliferative disorder in a subject by means of methylation-sensitive restriction enzyme analysis. Said kit comprises a container and a DNA microarray component. Said DNA microarray component being a surface upon which a plurality of oligonucleotides are immobilized at designated positions and wherein the oligonucleotide comprises at least one CpG methylation site. At least one of said oligonucleotides is specific for the at least one gene or genomic sequence selected from the group consisting of BCL2, BDNF, CACNA1G, CALCA, CRABP1, DLEC1, GATA3, HOXA1, IGF2, KL, NEUROG1, NR3C1, RUNX3, SOCS1 (Table 6); e.g., within SEQ ID NOS:128-141, 114-127 and 100-113 (respective genomic, CpG island and amplicons, respectively) and comprises a sequence of at least 15 base pairs in length but no more than 200 bp of a sequence according to one of SEQ ID NOS:128-141, 114-127 and 100-113 (respective genomic, CpG island and amplicons, respectively). Preferably said sequence is at least 15 base pairs in length but no more than 80 bp of a sequence according to one of SEQ ID NOS:128-141, 114-127 and 100-113 (respective genomic, CpG island and amplicons, respectively). It is further preferred that said sequence is at least 20 base pairs in length but no more than 30 bp of a sequence according to one of SEQ ID NOS:128-141, 114-127 and 100-113 (respective genomic, CpG island and amplicons, respectively).

Said test kit preferably further comprises a restriction enzyme component comprising one or a plurality of methylation-sensitive restriction enzymes.

In a further embodiment said test kit is further characterized in that it comprises at least one methylation-specific restriction enzyme, and wherein the oligonucleotides comprise a restriction site of said at least one methylation specific restriction enzymes.

The kit may further comprise one or several of the following components, which are known in the art for DNA enrichment: a protein component, said protein binding selectively to methylated DNA; a triplex-forming nucleic acid component, one or a plurality of linkers, optionally in a suitable solution; substances or solutions for performing a ligation e.g. ligases, buffers; substances or solutions for performing a column chromatography; substances or solutions for performing an immunology based enrichment (e.g. immunoprecipitation); substances or solutions for performing a nucleic acid amplification e.g. PCR; a dye or several dyes, if applicable with a coupling reagent, if applicable in a solution; substances or solutions for performing a hybridization; and/or substances or solutions for performing a washing step.

The described invention further provides a composition of matter useful for detecting, differentiation and distinguishing between colon cell proliferative disorders. Said composition comprising at least one nucleic acid 18 base pairs in length of a segment of the nucleic acid sequence disclosed in SEQ ID NOS:170-197, 226-253, 142-169 and 198-225, and one or more substances taken from the group comprising: 1-5 mM Magnesium Chloride, 100-500 µM dNTP, 0.5-5 units of taq polymerase, bovine serum albumen, an oligomer in particular an oligonucleotide or peptide nucleic acid (PNA)-oligomer, said oligomer comprising in each case at least one base sequence having a length of at least 9 nucleotides which is complementary to, or hybridizes under moderately stringent or stringent conditions to a pretreated genomic DNA according to one of the SEQ ID NOS:170-197, 226-253, 142-169 and 198-225 and sequences complementary thereto. It is preferred that said composition of matter comprises a buffer solution appropriate for the stabilization of said nucleic acid in an aqueous solution and enabling polymerase based reactions within said solution. Suitable buffers are known in the art and commercially available.

In further preferred embodiments of the invention said at least one nucleic acid is at least 50, 100, 150, 200, 250 or 500 base pairs in length of a segment of the nucleic acid sequence disclosed in SEQ ID NOS:170-197, 226-253, 142-169 and 198-225.

While the present invention has been described with specificity in accordance with certain of its preferred embodiments, the following examples serve only to illustrate the invention and are not intended to limit the invention within the principles and scope of the broadest interpretations and equivalent configurations thereof.

Example 1

Rationale, Samples and Methods for Studies of CpG Island Methylator Phenotype in Human Colorectal Cancer Rationale. As reviewed above, a lack of uniform standards and systematic marker development has created confusion and uncertainty in the field regarding the precise classification of the CpG Island Methylator Phenotype (CIMP).

Unsupervised two-dimensional cluster analysis of DNA methylation data for large numbers of markers and large numbers of tumor samples can be a useful tool to identify such distinct correlated subsets of tumors and markers. Although microarray-based methods for screening CpG island hypermethylation have been developed, most are not limited to Type C loci, and most are not readily applied to large numbers of tumor samples, which is required to obtain stable clusters.

Therefore, to resolve the controversy surrounding the validity of a distinct CpG island methylator phenotype, we explored the DNA methylation behavior of human colorectal tumors using automated real-time PCR-based MethyLight™, which is capable of rapidly assessing the methylation status of more than 100 different CpG islands on more than 100 different tissue samples. Specifically, an initial systematic evaluation of DNA methylation markers was conducted by the present applicants to address the following three issues:

First, and most importantly, a confirmation that CIMP could be recognized as a distinct subgroup of colorectal cancer was needed. Although the CIMP trait is widely accepted in the scientific community, and has been reported as a distinct entity by a very large number of independent laboratories, a recently published influential report suggests that CpG island hypermethylation frequency is a continuous trait in human colorectal cancer, without a clearly defined separate subgroup of tumors with frequent CpG island hypermethylation (38). It was thus of interest to confirm whether this report was due to the inclusion of a large number of CpG islands that do not belong to the CIMP subset, or whether there is indeed little justification for separating out a distinct subset of colorectal cancers. To avoid bias either for or against the existence of CIMP, applicants started a multi-step screen with 195 unique MethyLight™ CpG island hypermethylation assays available in applicants' laboratory, and used both previously characterized CIMP+ and CIMP− tumors to select cancer-specific methylation markers for further evaluation (see below). Furthermore, applicants used a battery of cluster analysis routines to evaluate whether CIMP tumors form a distinct grouping, and used several different gene selection algorithms, including gene filter, logistic regression, classification and regression trees (CART) (140) and gene shaving (141) to choose potential CIMP markers for further consideration (see below).

Second, a CIMP analysis technology platform was needed that could accommodate the difficult requirements of a large-scale study, including i) compatibility with very limited amounts of formalin-fixed, paraffin-embedded tissue (a single 5-µm microscopic slide), ii) robust performance, regardless of DNA quantity and quality (traditional gel-based methylation-specific PCR (MSP) is DNA quality and quantity-dependent), and iii) automatable analysis, to accommodate large numbers of specimens, while minimizing human error, cross contamination, and post-PCR contamination (see below).

Third, if CIMP could be verified, then the question as to whether the existing classification panels of markers were sufficient, or whether better panels could be developed needed to be evaluated. Applicants perceived in advance that the evaluation of classification panels would be particularly problematic without an external gold standard for CIMP classification. Therefore, a cross-panel misclassfication error rate strategy was selected by applicants to best confront this challenge (see below).

These issues needed to be resolved to enable the characterization of CIMP in a large-scale population-based studies.
Materials and Methods Colorectal Cancer Specimens. DNA samples were drawn from the Walter Paulson Tumour Bank, a consecutive series of over 800 colorectal cancer cases collected at the Royal Brisbane and Womens Hospital between 1989 and 2004. Patients gave informed consent in writing to the use of their bowel tissue for research. The study was approved by the Royal Brisbane Hospital Human Research Ethics Committee, the Bancroft Centre Ethics Committee and the USC Institutional Review Board. Tumors were collected at surgery and representative sections for research were removed by a pathologist. DNA was extracted using a modification of the salt precipitation technique of Miller et al.[13]. The first screen (FIG. 1) included five CIMP+ tumors, and five CIMP− tumors, which had been previously assessed for their CIMP status using a panel of four MINT loci (1, 2, 12 and 31) and MLH1, analyzed by combined bisulfite restriction analysis (COBRA) and three Type C genes (p14/ARF, CDKN2A (p16), MGMT), analyzed by gel-based methylation specific PCR (MSP)[14]. CIMP+ tumors were defined as having 80-100% of the markers methylated, while the five CIMP− tumors had an average of only 11% of markers methylated. Other tumor characteristics were obtained by standard techniques. KRAS (K-ras) mutation analysis at codons 12 and 13 was performed using direct automated sequencing of a fragment containing codon 12 and 13 in exon 1 of the KRAS gene, amplified using a touchdown PCR cycle and hotstart protocol. BRAF (B-raf) mutation analysis at codon 600 (V600E; formerly V599E[15]) was performed by a real-time PCR-based allelic discrimination method, as described[16]. Microsatellite instability was determined as described[17]. Eight cases of MSI-H cancer showed features consistent with HNPCC including young age of onset (average 44, range 31-53), family history, lack of MSH2 expression by tumor immunohistochemistry (n=4), and germline mutation of a mismatch repair gene (n=4).

DNA Methylation Analysis Technology. Treatment of genomic DNA with sodium bisulfite, followed by alkaline treatment converts unmethylated cytosines to uracil, while leaving methylated cytosine residues intact was used. Sequence variants at a particular locus can subsequently be analyzed by PCR amplification with primers designed to anneal with bisulfite-converted DNA. The benefit of sodium-bisulfite-based assays is that they require very small amounts of DNA and consequently, are compatible with DNA obtained from microdissected paraffin-embedded tissue samples (8, 145-158). However, until the development of the MethyLight™ assay (6-8, 20, 106), bisulfite-based DNA methylation detection required gel electrophoresis and many of the techniques also employed restriction enzyme digestion, radiolabeled dNTPs, or hybridization probes. These labor-intensive steps limited the use of these methods for high-throughput analyses. More recently, sodium-bisulfite-based microarray platforms have been developed. However, these platforms still require separate PCR amplification of each target locus to hybridize with the chip. With MethyLight™ technology, the methylation analysis is complete, as soon as the PCR reaction is finished. With microarray-based detection, the PCR amplificates need to be subsequently hybridized to the microarray, the hybridization signal needs to be captured, and then interpreted to yield DNA methylation measurements. Therefore, compared to MethyLight™, the current chip-based platforms are neither more cost-effective, nor less labor-intensive. More importantly, however, MethyLight™ is much better suited for the analysis of challenging samples, such as formalin-fixed paraffin-embedded samples with small amounts of highly degraded cross-linked DNA. The average amplicon size for reactions developed in applicants' laboratory is about 80 bp, which is well below the median amplifiable fragment size from formalin-fixed tissues. The MethyLight™ technique has been cross-validated with several other DNA methylation analysis techniques, including COBRA and bisulfite genomic sequencing(6). MethyLight™ is rapidly becoming the method of choice for large-scale automated DNA methylation studies requiring high sensitivity (8, 20, 98, 99, 106, 161-174), and has been adopted by many other laboratories.

Therefore, genomic DNA was treated with sodium bisulfite and subsequently analyzed by MethyLight™ as described[18,19]. A complete list of all MethyLight™ reactions is provided in TABLE 1 (supplemental table 1). MethyLight™ data are reported as a ratio between the value derived from the real-time PCR standard curve plotted as log (quantity) versus threshold C(t) value for the methylation reaction and likewise for a methylation-independent control reaction. However, since such a ratio is dimensionless, can vary from gene to gene, and is affected by many experimental parameters, such as primer and probe batches, it is useful to normalize this ratio to the ratio obtained for a constant reference sample. M.SssI-treated genomic DNA, frozen in aliquots, was used as a constant reference sample to determine this ratio and to derive the standard curve[20]. Thus, the Percent of Methylated Reference ("PMR") can be defined as $100*(METHYLATED\ REACTION/CONTROL\ REACTION)_{sample}/(METHYLATED\ REACTION/CONTROL\ REACTION)_{M.SssI-Reference}$, in which "METHYLATED REACTION" refers to the methylation measurement at a particular locus and "CONTROL REACTION" refers to the methylation-independent measurement using the control reaction[20]. Applicants have developed an improved normalization control reaction based on dispersed Alu repeats[18]. For the data supplied in FIG. 1, COL2A1 was used as a normalization control reaction[21]. For the data in FIG. 2, the mean of PMR values derived with COL2A1 and ALU was used. For the data in FIGS. 3, 4 and 5, PMR values were derived exclusively using the ALU normalization control reaction. This ALU normalization reaction is methylation independent[18], and not the methylation-dependent ALU reactions, which we have also previously described[18]. Applicants currently rely on the ALU normalization reaction, since it is less prone to fluctuations caused by aneuploidy and copy number changes affecting single-copy normalization reactions.

Selection of Type C Markers. Applicants screened all 195 available MethyLight™ markers in the Laird laboratory to identify Type C markers in colorectal cancer. Most of these markers had been developed for other purposes, including studies of esophageal cancer, lung cancer, pancreatic cancer, ovarian cancer, brain cancer and neurodegenerative disorders. Therefore, this starting collection is not likely to be biased with respect to CIMP analysis. Applicants used five CIMP+ tumors, and five CIMP− tumors, which had been previously assessed for their CIMP status as described above. Applicants used three criteria to select Type C markers for further evaluation. First, any marker for which the highest PMR value among these 20 samples was less than 2 was excluded. Second, any marker for which the mean PMR for tumor samples was at least twice that of normal samples was included. Third, any marker for which all normal samples had a PMR<2 and for which all tumor samples had a PMR>2 was included. Both the second and third criteria were applied separately to both the CIMP+ tumors and CIMP− tumors as well as to all ten cases collectively. A marker was included if it passed at least one of the criteria in any of the three sample comparisons (CIMP−, CIMP+, or both). Applicants applied this relatively relaxed, inclusive marker filter primarily to eliminate non-cancer-specifically methylated markers, not to identify top marker candidates. This marker screen resulted in a collection of 92 reactions that passed this first screen for tumor-specificity. Among these 92 reactions were five methylation markers (CDKN2A (p16), MLH1, MINT1, MINT2, and MINT31) that have been commonly used to define CIMP status.

Cluster Analysis. For the hierarchical cluster analysis shown in FIG. 2, applicants grouped the PMR values for each marker into quartiles. Applicants used Manhattan distance and average linkage to perform the clustering[7]. Two distinct clusters were identified. Applicants also performed three other clustering routines (not shown). For the second clustering routine, applicants defined loci with PMR values above 10 as methylated and counted the number of methylated loci for each tumor. The resulting index was clustered using PAM (partitioning around medioids)[7]. The number of clusters was selected by choosing the number that gave the highest average silhouette width. This method selected two clusters. The third method, the Gaussian mixture model[8], was fit using the top nine principal components of the log-transformed data (ln (PMR+1)). These nine principal components explained 78% of the variability in the DNA methylation data. Using the BIC curve to select the number of clusters, applicants selected four. The final method, PAM, was also fit to the log-transformed data. Again two clusters were suggested by the average silhouette width. Using these four different algorithms applicants saw remarkable overlap in subjects that fell into what applicants call our CIMP+ cluster. A subset of six individuals was defined as CIMP+ by all four clustering methods. Another seven individuals are identified as CIMP+ by at least one method. The remaining 35 subjects were classified as CIMP– by all methods. Scaling the data before conducting the principal components analysis, or before clustering with PAM, had little effect on the results.

CIMP Marker Selection. Applicants used the different cluster routines described above to classify tumors as either CIMP+ or CIMP–. This yielded similar but distinct classifications of CIMP+ or CIMP–. Applicants then applied three different marker selection algorithms (gene filter, classification and regression trees (CART)[22], logistic regression) to these classifications to identify those markers that best identify CIMP. For each marker selection algorithm, applicants ranked the importance of each marker for each definition of CIMP and selected the five markers for each algorithm that ranked the highest across all definitions of CIMP. Applicants also applied a fourth marker selection algorithm (gene shaving[23]) designed to select the markers that explain the most variability in the data without knowledge of CIMP status.

For the gene filter approach, applicants ranked the individual markers based on their ability to predict CIMP+ using the Wilcoxon test. Multivariable models to predict CIMP+ were created using CART and logistic regression. For logistic regression, forward stepwise regression to was used to select the five most significant markers for each outcome. CART selected at most two markers before the CIMP+ group was perfectly identified for each of the four gene cluster algorithms. Each of the first three approaches was fit to each of the definitions of CIMP+. The markers were ranked in terms of importance and those achieving the highest rank across all CIMP definitions were selected. For gene shaving, we shaved off 10% of the markers at each step. A total of 36 markers (39%) are identified as explaining the most variability in the tumor samples. From this subset, applicants selected the five markers that explained the most variability in the samples.

The four CIMP marker selection algorithms described above each generated five top CIMP marker candidates. The union of markers from the overlapping sets comprised a panel of 9 CIMP-predicting markers. Although the five most popular traditional CIMP markers (CDKN2A (p16), MINT1, MINT2, MINT31, and MLH1) all participated in the 92-marker cluster routines and marker selection strategies, none of these five markers was selected as one of the top five candidates in any of the marker selection algorithms.

As an added precaution, in addition to the nine CIMP-specific markers selected above, applicants also included the five best Type-C markers among the CIMP-specific markers, selected using a gene filter approach, since the CIMP marker selection strategies described above were driven by a relatively small number of CIMP+ tumors. Inappropriately retained markers would be expected to drop out at subsequent screening steps. Using a PMR of 10 to define positive methylation, applicants found the subset of markers that had no methylation in adjacent normal tissue (N=31 markers, all PMR values <10). In this subset, applicants ranked markers by the number of samples that showed positive methylation (PMR>10) in tumor tissue. Fourteen markers show more frequent methylation in tumor tissue than in normal tissue (all p<0.008). Five of the fourteen markers are markers that have been selected as CIMP-predicting (CRABP1, NR3C1, BCL2, BDNF, CACNA1G). The remaining nine are correlated with the selected markers. Applicants selected the top five Type C markers that were not already selected in a previous panel.

Figure 6:
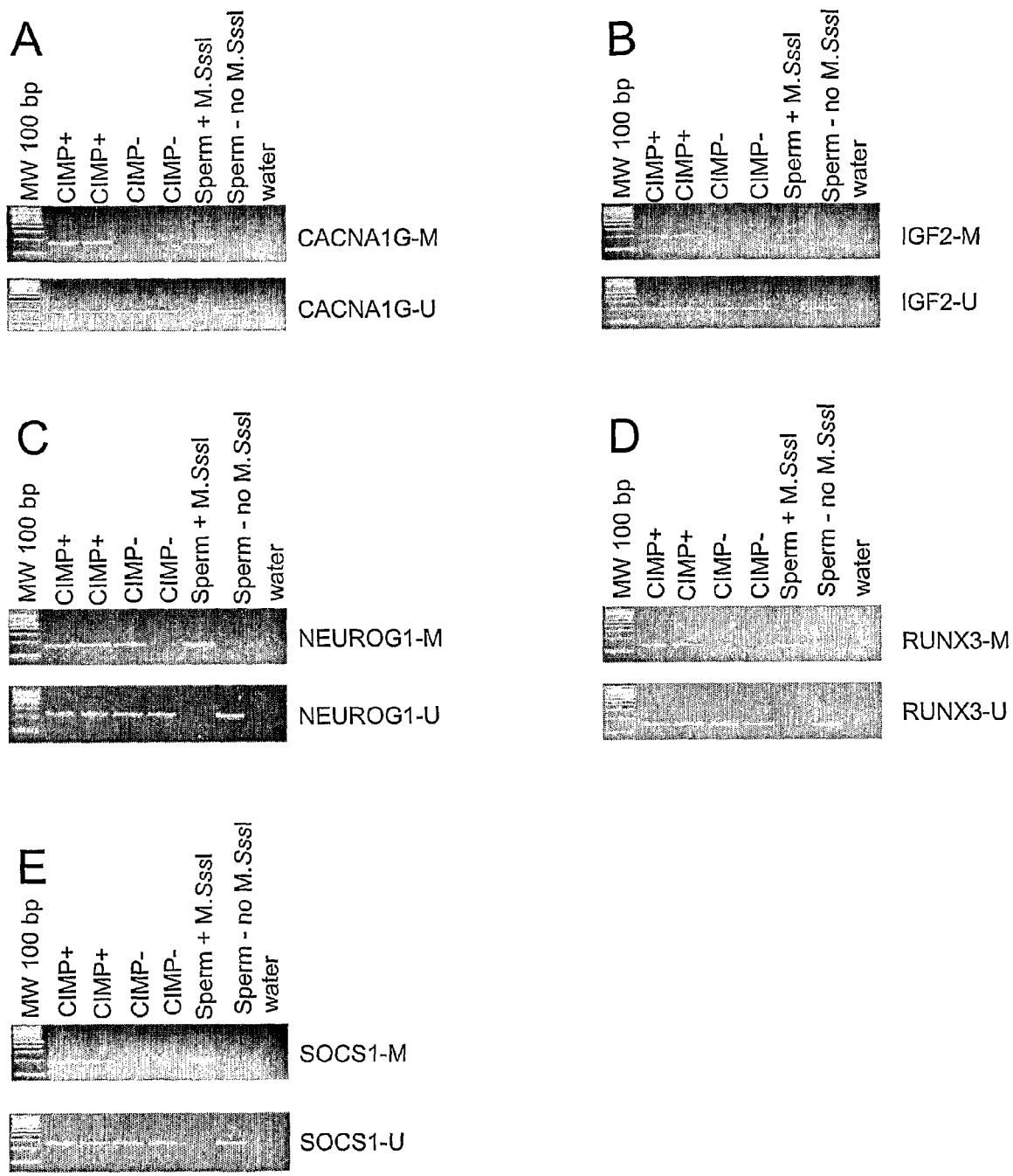
FIG. 6 shows, according to particular aspects, methylation-specific PCR (MSP) of a New CIMP Panel on CIMP+ and CIMP− colon tumor DNA samples. MSP reactions specific for the methylated (M) and the unmethylated (U) bisulfite-converted DNA sequences were designed for each gene in the New CIMP Panel: (A) CACNA1G, (B) IGF2, (C) NEUROG1, (D) RUNX3 and (E) SOCS1. Each MSP reaction was evaluated on two CIMP+ and two CIMP− bisulfite-converted colon tumor DNA samples using AmpliTaq Gold DNA polymerase (Applied Biosystems). Human sperm DNA and human sperm DNA treated in vitro with the M.SssI CpG methylase served as negative and positive methylation controls, respectively, for each MSP reaction. The PCR products were visualized by UV illumination after electrophoresis on 3% agarose gels and ethidium bromide staining. A 100 base pair molecular weight ladder was used to assess the PCR product size. MSP reactions tend to be less specific, but more sensitive than MethyLight reactions, since they lack the additional methylation specificity conferred by the MethyLight probe. This difference may be particularly noticeable for the less specific markers in our panel, such as NEUROG1 (highest percentage of methylated tumors in FIGS. 4 and 5). One CIMP− tumor was methylated for the NEUROG1 marker, consistent with MethyLight™ results obtained for this tumor. The threshold of three methylated markers out of a panel of five markers for the definition of CIMP-positive tumors was developed for the equivalent MethyLight™ reactions. The optimal threshold may differ when using the MSP versions of these markers. The MSP primer and probe sequences are described in the table of MSP primers on page 3.

New CIMP Classification Panel. Applicants dichotomized all PMR values at 10 to simplify panel assembly and to allow for an easier translation of our panels to gel-based MSP[24], which outputs only nominal data (methylated or unmethylated) (FIG. 6). The dichotomization threshold of PMR=10 was chosen as a point sufficiently above background measurements of methylation, using the MethyLight™ technique, possibly reflecting low rates of stochastic hypermethylation, yet well below the much higher PMR values generally obtained for hypermethylation observed for most markers in colorectal tumors. This definition yields 85% specificity in normal mucosa for the CIMP-specific markers identified in the clustering analysis routines. Applicants strove to identify as small a panel as possible that would accurately identify CIMP+ tumors, since this would provide the most cost-effective screening method for CIMP status. Based on the results obtained in FIG. 4, applicants considered a panel of five markers to be sufficient to detect bimodal methylation distribution among tumors, and to thus provide reasonably accurate CIMP classification ability. Applicants subsequently also tested larger panels of ten markers but found very little gain in classification accuracy. To select the best possible five-marker panel from the 14 markers shown in FIG. 3, applicants evaluated all 2,002 possible five-marker panels by measuring a panel's ability to identify CIMP by its bimodal appearance. Statistically, bimodal appearance is measured by the proportion of total variability of our index (0-5 methylated loci) explained by our classification rule (3-5 methylated loci=CIMP+, 0-2 methylated loci=CIMP–). The larger the variance explained, the more bimodal the distribution. The threshold of three or more methylated loci for defining CIMP+ tumors was established by minimizing the within group sum of squared errors. Applicants also considered MethyLight™ reaction performance characteristics of each individual marker. Among the most important reaction characteristics is the real-time PCR threshold cycle (C(t) value) on a standardized sample of fully methylated DNA, which is a measure of reaction sensitivity and efficiency. This measure is of particular importance for the analysis of samples containing borderline quantities of DNA. Applicants also considered the delta C(t) value for methylated, versus unmethylated human genomic reference DNA samples—a measure of methylation specificity for the reaction. As a final criterion, applicants also considered a bimodal distribution of the PMR values for the individual markers—markers with a large fraction of intermediate methylation measurements will more likely cause misclassification than markers that are more bimodal in their distribution of PMR values. One of the criteria that was specifically not considered is the functional consequence of the CpG island hypermethylation event. Applicants hypothesize that CIMP represents an epigenetic control defect and that many of the markers that may best reflect this defect may be of no functional significance to tumorigenesis. The five-marker panel that best satisfied all of the criteria described above and retained a high ranking in their ability to explain the percent of variance by the CIMP definition consisted of CACNA1G, IGF2, NEUROG1, RUNX3, and SOCS1 (TABLE 2 (supplemental table 2)).

TABLE 1

(supplementary table 1); Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| ABCB1 | ABCB1-M1B | HB-051 | MDR1; PGY1/AT P-binding cassette, sub-family B (MOR/TAP), member 1 | Y | N | 7q21.1 | TCGGGTCGGG AGTAGTTATT TG | CGACTATACT CAACCCACGC C | 6FAM-AGGCTATTCC TACCCAACCA ATCAACCTC A-BHQ-1 | Ehrlich, M. et al. Oncogene 21, 6694-6702 (2002) |
| APC | APC-M1B | HB-153 | Adenomatous polyposiscoli | Y | N | 5q21-q22 | GAACCAAAAC GCTCCCCAT | TTATATGTCG GTTACGTGCG TTTATAT | 6FAM-CCCGTCGAAA ACCCGCCGAT TA-BHQ-1 | Eads, C. A. et al. Cancer Res 61, 3410-3418 (2001) |
| APEX1 | APEX1-M1B | HB-090 | APEX nuclease (multifunctional DNA repair enzyme 1) | N | N | 14q11.2-q12 | CGTATTTGTA TCGGTTCGAT GGTA | GCGCATTCTT CGACCACG | 6FAM-CAAACGCGCC TCTAATCACG TAACCAAAT-BHQ-1 | GenBank Number AL355075; Amplicon Location: 64818-64684 |
| APP | APP-M1B | HB-266 | Amyloid beta (A4) precursor protein (protease nexin-II, Alzheimer disease) | N | N | 21q21.2 | AACGAAATGC GGATAAAAAC GTAT | TCGTCCCCGT AAACTTAAAT CATC | 6FAM-CCCGCAAACC TCCCGAAAAT ATCGTATAA A-BHQ-1 | GenBank Number 08767S; Amplicon Location: 8572-8667 |
| ARF/CDKN2A | ARF-M1B | HB-196 | P14 ARF; alternate reading frame of CDKN2A | Y | N | 9p21 | ACGGGCGTTT TCGGTAGTT | CCGAACCTCC AAAATCTCGA | 6FAM-CGACTCTAAA CCCTACGCAC GCGAAA-BHQ-1 | Eads, C. A. et al. Cancer Res 61, 3410-3418 (2001) |
| ARPC1B | ARPC1B-M1B | HB-186 | Actin related protein 2/3 complex, subunit 1B, 41 kDa; ARC41 | N | N | 7q22.1 | TGCGCGGGTA TCGGTAGTAT | ACCTAAAACA ACGATCGCGA AAT | 6FAM-CAAATCCCGC CCTCCCTTCG AAAT-BHQ-1 | GenBank Number AC004922; Amplicon Location: 57135-57206 |
| ATM | ATM-M1B | HB-179 | Ataxia telangiectasia mutated (includes complementation groups A, C and D) | N | N | 11q22-q23 | ACGGAGAAAA GAAGTCGTGG TC | GCGACGATAA CTACAACGCA AAT | 6FAM-CGACTCCTCT CGCCTCCTCC CG-BHQ-1 | GenBank Number U82828; Amplicon Location: 10785-10854 |

TABLE 1-continued (supplementary table 1): Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| ATR | ATR-M1B | HB-180 | Ataxia telangiectasia and Rad3 related; FRP1; SCKL; SCKL1 | N | N | 3q22-q24 | AGCGGTTTTC GGGAGAGT | GAATCCCGA CGTCTCCAAA | 6FAM-CGACGCCCGA CGAAACCGTA TAA-BHQ-1 | GenBank Number AC134509; Amplicon Location: 59222-59312 |
| AXIN1 | AXIN1-M1B | HB-227 | Axin 1 | N | N | 16p13.3 | CGGTTTTTGT AGTTGTTTCG TGTT | CGACGCGATA ACCGCTTAAA | 6FAM-ATCCGAAACC TCGAACGCGT CTCG-BHQ-1 | GenBank Number AE006463; Amplicon Location: 84738-84807 |
| BCL2 | BCL2-M1B | HB-140 | Bcl-2; B-cell CLL/lymphoma2 | Y | Y | 18q21.3 | TCGTATTTCG GGATTCGGTC | AACTAAACGC AAACCCCGC | 6FAM-ACGACGCCGA AAACAACCGA AATCTACA-BHQ-1 | Widschwendter, M. et al Cancer Res 64, 3807-3813 (2004) |
| BDNF | BDNF-M2B | HB-258 | Brain derived neurotrpohic factor | Y | Y | 11p13 | CGTATCGGGT TGGTTTTTT GTT | CGCCCGCTCG CTATCC | 6FAM-CCGTAACGCC TCGAACTCCC GA-BHQ-1 | GenBank Number AC103796; Amplicon Location: 3794-3866 |
| BRCA1 | BRCA1-M1B | HB-045 | Breast cancer 1, early onset; RNF53; BRCC1 | N | N | 17q21 | GAGAGGTTGT TGTTTAGCGG TAGTT | CGCCCAATCG CAATTTTAAT | 6FAM-CCGCGCTTTT CCGTTACCAC GA-BHQ-1 | Fiegl, H. et al Cancer Epidemiol Biomarkers Prev 13, 882-888 (2004) |
| BRCA2 | BRCA2-M1B | HB-126 | breast cancer 2, early onset | N | N | 13q12.3 | CGTTACGGCG TTACGTGGT | CCGCCTCTAC CGCCTAATTT | 6FAM-CGGCCACAA ACCCGCG-BHQ-1 | GenBank Number AL445212; Amplicon Location: 83637-83703 |
| CACNA1G | CACNA1G-M1B | HB-518 | Calcium channel, voltage-dependent, alpha 1G subunit | Y | Y | 17q22 | TTTTTTCGTT TCGCGTTTAG GT | CTCGAAACGA CTTCGCCG | 6FAM-AAATAACGCC GAATCCGACA ACCGA-BHQ-1 | GenBank Number AC021491; Amplicon Location: 48345-48411 |

TABLE 1-continued (supplementary table 1): Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| CALCA | CALCA-M1B | HB-166 | Calcitonin/calcitonin-related polypeptide, alpha; CALC1 | Y | Y | 11p15.2-p15.1 | GTTTTGGAAG TATGAGGGTG ACG | TTCCGCCGC TATAAATCG | 6FAM-ATTCCGCCAA TACACAACAA CCAATAAAC G-BHQ-1 | Eads, C. A. et al. Cancer Res 61, 3410-3418 (2001) |
| CCND1 | CCND1-M1B | HB-146 | Cyclin D1 (PRAD1: parathyroid adenomatosis 1); BCL1; D11S287E | N | N | 11q13 | GGTAATTTCG TCGTAGGGTA GGC | GAACGCCAAA CGCCCGA | 6FAM-ACCCAAAAAC CATCCCTAAA ACGCCG-BHQ-1 | GenBank Number AF511593; Amplicon Location: 1211-1293 |
| CCND2 | CCND2-M1B | HB-040 | Cyclin D2 | Y | N | 12p13 | GGAGGGTCGG CGAGGAT | TCCTTTCCCC GAAAACATAA AA | 6FAM-CACGCTCGAT CCTTCGCCC G-BHQ-1 | Ehrlich, M. et al. Oncogene 21, 6694-6702 (2002) |
| CDH1 | CDH1-M2B | HB-050 | E-cadherin (epithelial)/Cadherin 1, type 1 | N | N | 16q.22.1 | AGGGTTATCG CGTTTATGCG | TTCACTTACC GACCACAACC A | 6FAM-ACTAACGACC CGCCACCCG A-BHQ-1 | GenBank Number AC099314; Amplicon Location: 80648-80743 |
| CDH13 | CDH13-M1B | HB-075 | H-Cadherin/Cadherin 13, H-cadherin (heart)/T-cadherin; CDHH | Y | N | 16q24.2-q24.3 | AATTTCGTTC GTTTTGTGCG T | CTACCCGTAC CGAACGATCC | 6FAM-AACGCAAAAC GCGCCCGAC A-BHQ-1 | Fiegl, H. et al Cancer Epidemiol Biomarkers Prev 13, 882-888 (2004) |
| CDK2AP1 | CDK2AP1-M1B | HB-226 | CDK2-associated protein 1; DOC-1 (Deleted in oral cancer); DORC1; ST19 | N | N | 12p14.1 | CGCGGAAAGT TTGCGGT | CGACTTTTT ATTATCGACG ACTC | 6FAM-CGACAAATAT AACCGTCCGC GCCCTA-BHQ-1 | GenBank Number AC068768; Amplicon Location: 51406-51526 |
| CDKN1A | CDKN1A-M1B | HB-230 | Cyclin-dependent kinase inhibitor 1A; p21; Cip1p21; CIP1; SDI1; WAF1; CAAP20; CDKN1 | N | N | 6p21.2 | CGCGTTCGGT TTGCGTAT | TTATAATCCC GCTCTCCGCC | 6FAM-AAATCTCCGA CACATCCCGA CTCTCGT-BHQ-1 | GenBank Number Z85996; Amplicon Location: 3463-3554 |

TABLE 1-continued (supplementary table 1): Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| CDKN1C | CDKN1C-M2B | HB-329 | Cyclin-dependent kinase inhibitor 1C (p57, Kip2)/ BWS; WBS; BWCR; KIP2 | Y | N | 11p15.5 | TCGAGTAGGG CGCGAATTAG | GTCCCGAAAT CCCCGAAT | 6FAM-AACTAATCAA CGAAAAACTC CTAACCGCGC T-BHQ-1 | GenBank Number A0013791; Amplicon Location: 57564-57638 |
| CDKN2A | CDKN2A-M2B | HB-081 | p16/Cyclin-dependent kinase inhibitor 2A; CDKN2; CDK4I; p16; INK4a; MTS1; CMM2 | Y | Y | 9p21 | TGGAGTTTTC GGTTGATTGG TT | AACAACGCCC GCACCTCCT | 6FAM-ACCCGACCCC GAACCGCG-BHQ-1 | Eads, C. A. et al. Cancer Res 61, 3410-3418 (2001) |
| CDKN2B | CDKN2B-M1B | HB-173 | p15/Cyclin-dependent kinase inhibitor 2B; P15; MTS2; INK4B | N | N | 9p21 | AGGAGGAGA GAGTGCGTCG | CGAATAATCC ACCGTTAACC G | 6FAM-TTAACGACAC TCTTCCCTTC TTTCCCACG-BHQ-1 | Eads, C. A. et al. Cancer Res 61, 3410-3418 (2001) |
| CDX1 | CDX1-M1B | HB-195 | Caudal type homeo box transcription factor | N | N | 5q31-q33 | TGAGCGGTTG TTCGTCGTC | AAATCCCCCG CGCATACTA | 6FAM-CCTAAAACCG CCGCTACCG ACCG-BHQ-1 | GenBank Number A0005895; Amplicon Location: 35199-35266 |
| CGA | CGA1-M1B | HB-237 | Glycoprotein hormones, alpha polypeptide; GPHa; GPHA1 | N | N | 6q12-q21 | GGGTTTTTG TAGGATGTGT TTAGG | AACTACAATT ACTAAAAACT CATAAAAACGA AACT | 6FAM-TCCCTCTTCG AATCCACAAT CAACCG-BHQ-1 | GenBank Number AL138827; Amplicon Location: 56007-56096 |
| CHFR | CHFR-M1B | HB-190 | Checkpoint with forkhead and ring domains; FLJ10796 | Y | N | 12q24.33 | CGGGAGTTTT TATGGGCGT | AACCGTCCCC AAAACTACGA C | 6FAM-CCTCGACCCG CTCCATCGAA ATTCA-BHQ-1 | GenBank Number AC127070; Amplicon Location: 62442-62545 |
| CLDN1 | CLDN1-M1B | HB-059 | Claudin-1 | N | N | 3q28-q29 | CGGTGAGTCG TTTTGAAATC G | ACGCAAAACC GCTAAACGC | 6FAM-GATTTAAAAC AACTCCCGCC GCCTCA-BHQ-1 | GenBank Number A0009520; Amplicon Location: 27434-27530 |

TABLE 1-continued (supplementary table 1): Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| CLIC4 | CLIC4-M1B | HB-062 | Chloride intracellular channel 4 | N | N | 1p36.11 | GGCGGTGTTG AGGAGTTGA | CCGATTCCCG CCGTACTAC | 6FAM-CGCTAAACTA TCCGAAATCG AACTAACCAC G-BHQ-1 | GenBank Number AL117424; Amplicon Location: 47-119 |
| COL1A2 | COL1A2-M1B | HB-193 | Collagen, type I, alpha 2; OI4 | Y | N | 7q22.1 | CGGTAGTAGG AGGTTTCGGT TAAGT | CCTAAATCAC CGACGAAAAT ATCA | 6FAM-CGAACGCCAA CATACAATCG TAACCAATAC CT-BHQ-1 | GenBank Number AF004877; Amplicon Location: 2302-2390 |
| CRABP1 | CRABP1-M1B | HB-197 | Cellular retinoic acid binding protein 1; RBP5; CRABP; CRABPI; CRABP-I | Y | Y | 15q24 | TCGAAATTTT CGTTGTTGCG T | TATCCGTACC TACCGCCGC | 6FAM-ACCATACCCAA CTTCGCCGACA CCTAA-BHQ-1 | GenBank Number A0011270; Location: 122142-122223 |
| CTNNB1 | CTNNB1-M1B | HB-170 | Catenin (cadherin-associated protein), beta 1, 88 kDa; CTNNB | N | N | 3p22-21.3 | GGAAAGGCGC GTCGAGT | TCCCCTATCC CAAACCCG | 6FAM-CGGCGTTTC CCGAACCG-BHQ-1 | Eads, C. A. et al. Cancer Res 61, 3410-3418 (2001) |
| CTSD | CTSD-M1B | HB-147 | Cathepsin D (lysosomal aspartyl protease); CPSD | N | N | 11p15.5 | TACGTTTCGC GTAGGTTTGG A | TCGTAAAACG ACCCACCCTA A | 6FAM-CCTATCCCGA CCGCCGGA-BHQ-1 | GenBank Number AC068580; Amplicon Location: 43076-43166 |
| CXADR | CXADR-M1B | HB-054 | Coxsackie virus and adenovirus receptor; CAR | N | N | 21q11.2 | TACGCGGTTG GAGAAGTCG | ATAAACTCGC GTCACTTCGA | 6FAM-AACGACCCGA ACCGACTAC GAACG-BHQ-1 | Ehrlich, M. et al. Oncogene 21, 6694-6702 (2002) |
| CYP1B1 | CYP1B1-M1B | HB-078 | Cytochrome P450, family 1, subfamily B, polypeptide 1; GLC3A; CP1B | Y | N | 2p21 | GTGCGTTTGG ACGGGAGTT | AACGGACCT AACAAAACGA A | 6FAM-CGCCGCACAC CAAACCGCT T-BHQ-1 | Fiegl, H. et al Cancer Epidemiol Biomarkers Prev 13, 882-888 (2004) |

TABLE 1-continued (supplementary table 1); Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| CYP27B1 | CYB27B1-M1B | HB-223 | Cytochrome P450, family 27, subfamily B, polypeptide 1; CYP1; VDD1; PDDR | Y | N | 12q14.1 | GGGATAGTTAGAGAGAACGGATGTTT | CCGAATATAACCACACCGCC | 6FAM-CCAACCTCAACTCGCCTTTCCTTATTTCA-BHQ-1 | GenBank Number AY288916; Amplicon Location: 1728-1805 |
| DAPK1 | DAPK1-M1B | HB-046 | Death-associated protein kinase 1 | N | N | 9q34.1 | TCGTCGTCGTTTCGGTTAGTT | TCCCTCCGAAACGCTATCG | 6FAM-CGACCATAAACGCCAACGCCG-BHQ-1 | Muller, H.M. et al. Cancer Lett209, 231-236 (2004) |
| DCC | DCC-M1B | HB-178 | Deleted in colorectal carcinomas | Y | N | 18q21.3 | GGGTTCGGCGCGTGT | CGAAAAATACAAAAACCAACTTAAATACC | 6FAM-ACCAAAAATCGCAACGAACGACAACACT-BHQ-1 | GenBank Number AC011155; Amplicon Location: 118286-118444 |
| DCLRE1C | DCLRE1C-M1B | HB-133 | ARTEMIS/hypothetical protein FLJ11360; artemis protein; DNA cross-link repair 1C (PSO2 homolog, S. cerevisiae); SNM1C; A-SCID | N | N | 10p13 | CGAAGCGCGGGTGATTTA | AAAATCCGAAAACCGAAAACAA | 6FAM-ATCCGATCGAATTCTAAACGCCCGCTACT-BHQ-1 | GenBank Number AL360083; Amplicon Location: 54518-54603 |
| DDB1 | DDB1-M1B | HB-116 | Damage-specific DNA binding protein 1, 127 kDa | N | N | 11q12-q13 | GGGCGGAGGTAGCGGT | CCCGTCGAAACTCGAACG | 6FAM-CCAACAACGCGCAACGAACTCCA-BHQ-1 | GenBank Number AC090584; Amplicon Location: 203224-203324 |
| DIRAS3 | DIRAS3-M1b | HB-043 | Ras homolog gene family, memeber I/NOEY2; DIRAS family; GTP-binding RAS-like 3; ARHI | N | N | 1p31 | GCGTAAGCGGAATTTATGTTGT | CCGGCGATTTTATATTCCGACTT | 6FAM-CGACAAAAACGACAAATACGAAACGCAAA-BHQ-1 | Previously described as ARHI in Fiegl, H. et al Cancer Epidemiol Biomarkers Prev 13, 882-888 (2004) |
| DLC1 | DLC1-M1B | HB-218 | Deleted in liver cancer 1; HP; ARHGAP7; STARD12; FLJ21120; DLC-1; p122-RhoGAP | Y | N | 8p22-p21.3 | AGTAAGGATGCGTTGAGGATCG | ACGACTCGACTTCCGCGTC | 6FAM-AACCCACGACGACACCCGAAACG-BHQ-1 | GenBank Number AC015641; Amplicon Location: 115709-115784 |

TABLE 1-continued (supplementary table 1); Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| DLEC1 | DLEC-M1B | HB-225 | Deleted in lung and esophageal cancer 1 | Y | Y | 3p22-p21.3 | TCGTTGCGTA TTTAAGATAT TTCGTATT | CGTAACGCTC ATTCTCGCTA CC | 6FAM-TAATCAAACT TACGCTCACT TCGTCGCCG-BHQ-1 | GenBank Number AP006309; Amplicon Location: 19959-20088 |
| DNAJC15 | DNAJC15-M1B | HB-048 | DnaJ (Hsp40) homolog, subfamily C, member 15; DNAJD1; MCJ | N | N | 13q13 | TTTCGGGTCG TTTTGTTATG G | ACTACAAATA CTCAACGTAA CGCAAACT | 6FAM-TCGCCAACTA AAACGATAAC ACCAGAAC A-BHQ-1 | Previously described as MCJ in Ehrlich, M. et al. Oncogene 21, 6694-6702 (2002) |
| DPH1 | DPH1-M1B | HB-049 | Dipthamide Biosynthesis Protein 2, S. crevisiae, Homolog-Like 1; Candidate tumor suppressor in ovarian cancer 2 (OVCA2); DHP2L1; DPH2L | N | N | 17p13.3 | ACGCGAGAGAG CGTAGATATT G | CCGCCCAACG GAATATCCC | 6FAM-CCCGCTAACC GATCGACGAT CGA-BHQ-1 | GenBank Number AC090617; Amplicon Location: 196988-197057 |
| DRD1 | DRD1-M1B | HB-252 | Dopamine receptor D1 | Y | N | 5q35.1 | GGCGCGCGTT GGTTC | TACCCGTAAA ACGCCTATAC TCACC | 6FAM-CTCGCAAAAA AAACGCGAC GCAACTA-BHQ-1 | GenBank Number AC091393; Amplicon Location: 111358-111429 |
| DRD2 | DRD2-M1B | HB-253 | Dopamine receptor D2 | Y | N | 11q23 | GAAGTCGGAA ATTTTGGTCG C | ATCTCGAAAA AACACTTCCC CC | 6FAM-ACACCCAAAC GCGAAACCCG AAACT-BHQ-1 | GenBank Number AP002840; Amplicon Location: 110939-111008 |
| EBF3 | EBF3-M1B | HB-229 | COE3; Early B-cell factor 3; DKFZp667B0210 | Y | N | 10q26 | GTAGGATATT GCGGGATCGT TC | GCAACACTCA CTACCCCGTT TAT | 6FAM-TCTTTAAAAC AAACGAACCG CGCCAA-BHQ-1 | GenBank Number AL354950; Amplicon Location: 144175-144252 |

TABLE 1-continued (supplementary table 1): Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| EPM2AIP1 | EPM2AIP1-M1B | HB-152 | EPM2A (laforin) interacting protein 1; KIAA0766; FLJ11207 | Y | N | 3p21.3 | CGTTATATAT CGTTCGTAGT ATTCGTGTTT | CTATCGCCG CCTCATCGT | 6FAM-CCGGACGTCA AACGCCACTA CG-BHQ-1 | Eads, C. A. et al. Cancer Res 61, 3410-3418 (2001) |
| ERBB2 | ERBB2-M1B | HB-233 | Epidermal growth factor receptor (erythroblastic leukemia viral (v-erb-b) oncogene homolog, avian); NGL; HER-2; NEU | N | N | 17q21.1 | AGTGTGAGAA CGGTTGTAG GTAATTTAG | CCCTCTCTTC GCGCAAAC | 6FAM-AAATACGTCC GTCCTAACGC CGAAACG-BHQ-1 | GenBank Number AC079199; Amplicon Location: 44277-44352 |
| ERCC1 | ERCC1-M1B | HB-110 | Excision repair cross-complementing rodent repair deficiency, complementation group 1 (includes overlapping antisense sequence) | Y | N | 19q13.2-q13.3 | GGGCGAGTCG AAGGTGG | CTCCGAAAAC TCCATAACGT CAA | 6FAM-CCCAACGCTA AAAACTCTAT AACGCCACG-BHQ-1 | GenBank Number M63796; Amplicon Location: 22178-22088 |
| ERCC2 | ERCC2-M1B | HB-105 | Excision repair cross-complementing rodent repair deficiency, complementation group 2 (xeroderma pigmentosum D; XPD) | N | N | 19qq13.3 | CGAGTTTTCG AGGATGTTTA CGA | CCGACCGAAC CTATACAACG AAAT | 6FAM-ACCCGCCTC CCTCATAAAT ATTCAACGA A-BHQ-1 | GenBank Number AC092309; Amplicon Location: 4166-4250 |
| ERCC4 | ERCC4-M1B | HB-111 | Excision repair cross-complementing rodent repair deficiency, complementation group 4; RAD1; XPF | N | N | 16p13.3-p13.11 | TCGACCGATT GTTATGGCG | CCGTCAATAT CGAACAATTC CA | 6FAM-CACCAACTAT CGCTCGTACT CCAACACG-BHQ-1 | GenBank Number L76568; Amplicon Location: 2113-2184 |
| ERCC5 | ERCC5-M1B | HB-109 | Excision repair cross-complementing rodent repair deficiency, complementation group 5 (xeroderma pigmentosum, complementation | N | N | 13q22 | TAAGCGTAGA AAATATACGT TATGTGCG | CCCGCTCGAT TTCCGTCT | 6FAM-CGACGCCAA AACGAAAACT CCG-BHQ-1 | GenBank Number AL157769; Amplicon Location: 130480-130556 |

TABLE 1-continued (supplementary table 1): Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| | | | group G (Cockayne syndrome)); ERCM2; XPGC | | | | | | | |
| ERCC6 | ERCC6-M1B | HB-114 | Excision repair cross-complementing rodent repair deficiency, complementation group 6 (PGBD3); CKN2; CSB; RAD26 | N | | 10q11 | ACGTAAGTAG AAAGGCGTTG TTGAG | CGACTCCGAC TTCTACTAAT ACGAAA | 6FAM-CCCGTAACGC ATACGCCTAA CTCAACG-BHQ-1 | GenBank Number AC073366; Amplicon Location: 164190-164315 |
| ERCC8 | ERCC8-M1B | HB-113 | Excision repair cross-complementing rodent repair deficiency, complementation group 8 (ERCC8); Cockayne syndrome 1 (classical), CKN1; CSA | N | | 5q12.1 | GGTTAAGGCG TTTAGAGTCG GG | TCATACGACA CTTAAAATAT CACCGAAA | 6FAM-CCCTTCACTC TAACATCGAA ACCCTACCC G-BHQ-1 | GenBank Number AC073546; Amplicon Location: 21088-21200 |
| ESR1 | ESR1-M1B | HB-164 | Estrogen Receptor Alpha; NR3A1; Era | Y | | 6q25.1 | GGCGTTCGTT TTGGGATTG | GCCGACACGC GAACTCTAA | 6FAM-CGATAAAACC GAACGACCCG ACGA-BHQ-1 | Eads, C. A. et al. Cancer Res 60, 5021-5026 (2000) |
| ESR2 | ESR2-M1B | HB-165 | Estrogen receptor 2 (ER beta); MR3A2; Erb | Y | | 14q | TTTGAAATTT GTAGGGCGAA GAGTAG | ACCCGTCGCA ACTCGAATAA | 6FAM-CCACCCAACG CTCGCCG-BHQ-1 | Fiegl, H. et al Cancer Epidemiol Biomarkers Prev 13, 882-888 (2004) |
| FAF1 | FAF1-M1B | HB-304 | Fas (TNFRSF6) associated factor 1; CGI-03; hFAF1 | N | | 1p33 | CGTTTTGCGG TTTTACGTGA | CAACGCAAAA ATCCTAACCG AA | 6FAM-CGCGGCGCTCA ACGCTTAACA AAAAATA-BHQ-1 | GenBank Number AL359977; Amplicon Location: 63234-63308 |
| FBXW7 | FBXW7-M1B | HB-151 | F-box and WD-40 domain protein 7 (archipelago) | N | | 4q31.23 | TGTCGTTGCG GTTGGGAT | CGAAATAAA TAACTACTCC GCGATAA | 6FAM-ACGCCAAAAC TTCTACCTCG | GenBank Number AC023424; Amplicon |

TABLE 1-continued (supplementary table 1): Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| | | | homolog, Drosophila); AGO; FLJ11071; SEL10; FBW7; CDC4; FBXW6 | | | | | | TCCCGTAA-BHQ-1 | Location: 113422-113545 |
| FHIT | FHIT-M2B | HB-041 | Fragile Histidine Triad; FRA3B; AP3Aase | Y | N | 3p14.2 | GGCGCGGGTT TGGG | CGCCCCGTAA ACGACG | 6FAM-CACTAAACTC GAAATAATA ACCTAACGCG CG-BHQ-1 | GenBank Number AC097357; Amplicon Location: 121650-121724 |
| GABRA2 | GABRA2-M1B | HB-254 | Gamma-aminobutyric acid A, receptor, alpha 2 | Y | N | 4p12 | TCGTCGGAGG AGCGGA | AACCTCTCGA AAACCCCAAC A | 6FAM-ACGACTTCGA AAAACAACCC GAAACTACG-BHQ-1 | GenBank Number AC095060; Amplicon Location: 42382-42455 |
| GAD1 | GAD1-M2B | HB-256 | Glutamine decarboxylase 1 (67 kda) | Y | N | 2q31 | CGATTGGTTC GGCGTAGAAA | CCCTCCGATA TACAAAACCC C | 6FAM-CCCGCACAAC TCTCGCTTCT CTTTACAA-BHQ-1 | GenBank Number AC007405; Amplicon Location: 70850-70932 |
| GATA3 | GATA3-M1B | HB-327 | GATA binding protein 3/HDR; MGC5445 | Y | Y | 10p15 | TGTATCGGGA CGGAATCGTT | ACGCGCGCTC TAACCCTT | 6FAM-AAATATAACC GCGACTCCTA CCAATTCATT CG-BHQ | GenBank Number AL390294; Amplicon Location: 51880-51959 |
| GATA4 | GATA4-M1B | HB-323 | GATA binding protein 4 | Y | N | 8p23.1-8p22 | GATGGTGGTC GCGTGAAGTT A | TTCCCTCCAT ATACGAACTA CCG | 6FAM-CCTATCCCGA ATCCGTCAAT CCCG-BHQ-1 | GenBank Number AC069185; Amplicon Location: 28557-28630 |
| GATA5 | GATA5-M1B | HB-326 | GATA binding protein 5; bB379O24.1 | Y | N | 20q13.33 | AGTTACGTGA TTTTGGTAGG TTTTGTT | TAATCCGAAC TCCGCGCTA | 6FAM-CCCGTATCGT ACGTCCTTAT CGCCAAA-BHQ | GenBank Number AL499627; Amplicon Location: 19744-19828 |

TABLE 1-continued (supplementary table 1); Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| GDNF | GDNF-M1B | HB-221 | Glial cell derived neurotrophic factor | Y | N | 5p13.1-p12 | CGGTAGTTGT CGTTGAGTCG TTC | AACAACCGCC GCTACTTTAA ATA | 6FAM-CCGCGGTCGC GCTCTTAACT AAAA-BHQ-1 | GenBank Number AC008869; Amplicon Location: 108758-108866 |
| GRIN2B | GRIN2B-M1B | HB-250 | Glutamate receptor, ionotrophic, N-methyl-D-aspartate 2B (NR3); NMDAR2B | Y | N | 12p12 | GTCGGATTTA CGCGTCGAGT | CTACCGCCGC GCTAAAATAC | 6FAM-ACCCACGAAA CTTCACCTAC AACGTATCG-BHQ-1 | GenBank Number AC007916; Amplicon Location: 111645-111727 |
| GSTP1 | GSTP1-M1B | HB-172 | Glutathione-S transferase pi1; FAEES; GST3 | Y | N | 11q13 | GTCGGCGTCG TGATTTAGTA TTG | AAACTACGAC GACGAAACTC CAA | 6FAM-AAACCTCGCG ACCTCCGAAC CTTATAAAA-BHQ-1 | Eads, C. A. et al. Cancer Res 61, 3410-3418 (2001) |
| HIC1 | HIC1-M1B | HB-168 | Hypermethylated in cancer 1; ZBTB29 | Y | N | 17p13.3 | GTTAGCGCGGT TAGGGCGTC | CCGAACGCCT CCATCGTAT | 6FAM-CAACATCGTC TACCCAACAC ACTCTCCTAC G-BHQ-1 | Eads, C. A. et al. Cancer Res 61, 3410-3418 (2001) |
| HLA-G | HLA-G-M1B | HB-215 | HLA-G histocompatibility antigen, class I, G | N | N | 6p21.3 | CACCCCCATA TACGCGCTAA | GGTCGTTACG TTTCGGGTAG TTTA | 6FAM-CGGCGCTCACA CGCTCAAAAA CCT-BHQ-1 | Muller, H. M. et al Ann NY Acad Sci 1022, 44-49 (2004) |
| HOXA1 | HOXA1-M2B | HB-268 | Homeo box A1; HOX1F | Y | Y | 7p15 | TTGTTTATTA GGAAGCGGTC GTC | TCGAACCATA AAATTACAAC TTTCCA | 6FAM-TCGTACGCGA TCAAGCCAA CAATTA-BHQ-1 | GenBank Number AC004079; Amplicon Location: 78138-78220 |
| HOXA10 | HOXA10-M1B | HB-270 | Homeo box A10; HOX1H | N | N | 7p15-p14 | TGTATTGATG GGTTAGGAGA CGTATT | CCCACCAACC CACGTTAAAA CA | 6FAM-CAACTCCCGA CCTTCGAACC AAAATATCG-BHQ-1 | GenBank Number AC004080; Amplicon Location: 47850-47933 |

TABLE 1-continued (supplementary table 1); Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence$^a$ | Source |
|---|---|---|---|---|---|---|---|---|---|---|
| HOXA11 | HOXA11-M1B | HB-270 | Homeo box A11; HOX1I | N | N | 7p15-p14 | TTTTGTTTTC GATTTTAGTC GGAAT | TAATCAAATC ACCGTACAAA TCGAAC | 6FAM-ACCACCAAAC AACACCATCC ACGACTTCA-BHQ-1 | GenBank Number AC004080; Amplicon Location: 59150-59249 |
| HRAS | HRAS-M1B | HB-144 | V-Ha-ras Harvey rat sarcoma viral oncogene homolog; HRAS1 | N | N | 11p15.5 | GAGGCGATGAC GGAATATAAG TTGG | CGTCCACAAA ATAATTCTAA ATCAACTAA | 6FAM-CACTCTTACC CACACCGCCG ACG-BHQ-1 | Widschwendter, M. et al Cancer Res 64, 3807-3813 (2004) |
| HSD17B4 | HSD17B4-M1B | HB-066 | 17beta-hydroxysteroid dehydrogenase IV | N | N | 5q21 | TATCGTTGAG GTTCGACGGG | TCCAACCTTC GCATACTCAC C | 6FAM-CCCGCGCCGA TAACCAATAC CA-BHQ-1 | Muller, H. M. et al. Cancer Lett 209, 231-236 (2004) |
| ICAM1 | ICAM1B-M1B | HB-076 | Intercellular adhesion molecule 1 (CD54), human rhinovirus receptor; BB2; CD54 | N | N | 19p13.3-p13.2 | GGTTAGCGAG GGAGGATGAT T | TCCCCTCCGA AACAAATACT ACAA | 6FAM-TTCCGAACTA ACAAAATACC CGAACCGAA A-BHQ-1 | Ehrlich, M. et al. Oncogene 21, 6694-6702 (2002) |
| IFNG | IFNG-M1M | HB-313 | Interferon Gamma | N | N | 12q14 | TGAAGAGTTA ATATTTTATT AGGGCGAA | TTCCTTTAAA CTCCTTTAAA TCCTTTAACG | 6FAM-ACAAACCCAT TATACCCACC TA-MGBNFQ | GenBank Number AF375790; Amplicon Location: 1245-1407 |
| IGF2 | IGF2-M2B | HB-319 | IGF2: Insulin-like growth factor 2 (somatomedin A) | Y | N | 11p15.5 | GAGCGGTTTC GGTGTCGTTA | CCAACTCGAT TTAACCGAC G | 6FAM-CCCTCTACCG TCGCGAACCC GA-BHQ-1 | GenBank Number AC132217; Amplicon Location: 108633-108720 |
| IGSF4 | IGSF4-M1B | HB-069 | Immunoglobulin superfamily, member 4; TSLC1; NECL2; ST17; BL2; SYNCAM; IGSF4A | Y | N | 11q23.2 | GGGTTTCGGA GGTAGTTAAC GTC | CACTAAAATC CGCTCGACAA CAC | 6FAM-ACACTCGCCA TATCGAACAC CTACCTCAA A-BHQ-1 | Widschwendter, M. et al Cancer Res 64, 4472-4480 (2004) |
| ITGA4 | ITGA4-M1B | HB-321 | integrin, alpha 4 (antigen CD49D, alpha 4 subunit of VLA-4 receptor); CD49D | Y | N | 2q31-q32 | TGCGGAGGCG TAGGGTC | CAACCGAAAT TCCCCAACG | 6FAM-CCTACACCG CGGTAAACA AAAACG-BHQ-1 | GenBank Number AC020595; Amplicon Location: 146566-146639 |

TABLE 1-continued (supplementary table 1): Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| JUP | JUP-M1B | HB-203 | Junction Plakoglobin; CTNNG; PDGB; PKGB; DPIII | Y | N | 17q21 | GGATAGCGAA TTGAGTTCGG C | CTCTTCGCCT TTTATTCGAT TACTAAAT | 6FAM-AACAACCGCC GCCCGACCA-BHQ-1 | GenBank Number AC109319; Amplicon Location: 81609-81699 |
| KL | KL-M1B | HB-175 | human Klotho gene | Y | Y | 13q12 | AGTTTCGTTT TCGCGTAGTA TGTTC | CGCCCGACTC CGCAC | 6FAM-CGAACGACGC GACGAAACGC T-BHQ-1 | GenBank Number AB009667; Amplicon Location: 2062-2189 |
| LDLR | LDLR-M1B | HB-219 | Low density lipoprotein receptor (familial hypercholesterolemia) | N | N | 19p13.3 | GATATCGGTT TTTTAATTCG TGAAGTT | TTCACCGAAA ACCCAAATAC AA | 6FAM-ATCAAAATCGC CTACCCTAAC GACACTTTC G-BHQ-1 | GenBank Number AC011485; Amplicon Location: 90572-90674 |
| LIG3 | LIG3-M1B | HB-091 | ligase III, DNA, ATP-dependent | N | N | 17q11.2-q12 | GTCGCGGGTA GTTTACGACG | CGACCTTAAC TCTTACGCCT ACG | 6FAM-CGCTACCTCC CGCTCTAAAA CCCGA-BHQ-1 | GenBank Number AC022903; Amplicon Location: 14538-14629 |
| LPHN2 | LPHN2-M1B | HB-202 | Latrophilin 2; LEC1; LPHH1; KIAA0786 | Y | N | 1p31.1 | GAGGATTAG CGCGTAGTGA GTG | AATCCCGAA CTCTACCTCC A | 6FAM-CCCATTAACA CACCCATTCA ACCGCTAA-BHQ-1 | GenBank Number AL358939; Amplicon Location: 143237-143336 |
| LZTS1 | LZTS1-M1B | HB-200 | Leucine zipper, putative tumor suppressor 1 F37; FEZ1 | N | N | 8p22 | GCGGGCTTGT AGGGACG | CGCGCGCTAA CTCTTCTACG | 6FAM-ATTACCGCCT TTAAACTCCG AACCCTCCA-BHQ-1 | GenBank Number AC025853; Amplicon Location: 24463-24547 |
| MBD2 | MBD2-M1B | HB-142 | Methyl-CpG binding domain protein 2 | N | N | 18q21 | AGGCGAGAT AAGATGGTCG T | CCCTCCTACC CGAAACGTAA C | 6FAM-CGACCACCGC CTCTTTAAAT CCTCCAAA-BHQ-1 | GenBank Number AC093462; Amplicon Location: 143589-143667 |
| MBD4 | MBD4-M1B | HB-083 | Methyl-CpG binding domain protein 2 | N | N | 3q21-q22 | TCGTGTTTAT CGAGTAGGGT | TCGATTACAA CCCGATACCG | 6FAM-CACACCCTAA | GenBank Number AF449212; |

TABLE 1-continued (supplementary table 1); Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| | | | | | | | TCG | TAA | ACGTTACGAC GCTAAACTC G-BHQ-1 | Amplicon Location: 59852-59967 |
| MGMT | MGMT1-M2B | HB-160 | O-6-methylguanine-DNA methyltransferase | Y | N | 10q26 | GCGTTTCGAC GTTCGTAGGT | CACTCTTCCG AAAACGAAAC ACG | 6FAM-CCGAAACGAT ACGCACCGCG A-BHQ-1 | Virmani, A. K. et al. Cancer Epidemiol Biomarkers Prev11, 291-297 (2002) |
| MINT1 | MINT1-M1B | HB-161 | Colon cancer diferentially methylated CpG island genomic sequence; PROTEIN 2C (SV2C) in rats | Y | Y | 5q13-14 | GGGTTGAGGT TTTTGTTAG CG | CCCCTCTAAA CTTCACAACC TCG | 6FAM-CTACTTCGCC TAACCTAACG CACAACAAAC G-BHQ-1 | GenBank Number AC026774; Amplicon Location: 44288-44415 |
| MINT2 | MINT2-M1B | HB-187 | Colon cancer differentially methylated CpG island genomic sequence | Y | Y | 2p22-21 | TTGAGTGGCG CGTTTCGT | TCCCCGCCTA AACCAACC | 6FAM-CTTACGCCAC CGCCTCCGA-BHQ-1 | GenBank Number AC007238; Amplicon Location: 74436-74524 |
| MINT31 | MINT31-M1B | HB-162 | Colon cancer differentially methylated CpG island genomic sequence | Y | Y | 17q22 | GTCGTCGGCG TTATTTTAGA AAGTT | CACCGACGCC CAACACA | 6FAM-ACGCTCCGCT CCCGAATACC CA-BHQ-1 | GenBank Number AC021491; Amplicon Location: 50060-50130 |
| MLH1 | MLH1-M2B | HB-150 | Mut L Homolog 1 (E. coli) (colon cancer, nonpolyposis type 2); COCA2 | Y | Y | 3p21.3 | AGGAAGAGCG GATAGCGATT T | TCTTCGTCCC TCCCTAAAAC G | 6FAM-CCCGCTACCT AAAAAAATAT ACGCTTACGC G-BHQ-1 | Fiegl, H. et al Cancer Epidemiol Biomarkers Prev 13, 882-888 (2004) |
| MLH3 | MLH3-M1B | HB-099 | MutL (E. coli) homolog 3 | Y | N | 14q24.3 | TGATGATGGT TGCGCGTAGT | CGACCGCCAA AACCGC | 6FAM-CGAAACCCTC GCGCATCCG A-BHQ-1 | GenBank Number AL049780; Amplicon Location: 110441-110511 |
| MMS19L | MMS19L-M1B | HB-117 | MMS19 (MET18 S. cerevisiae)-like: MET-18, hMMS19 | N | N | 10q24-10q25 | TTAGGTAGAA GTCGGTAGGT ACGTGA | ATAACTCGA AACGAACTC TCCGC | 6FAM-CGCCTCCCGA ACCAATCTCC | GenBank Number AL359388; Amplicon |

TABLE 1-continued (supplementary table 1); Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| | | | | | | | | | G-BHQ-1 | Location: 11495-11598 |
| MSH2 | MSH2-M1B | HB-095 | MutS (E. coli) homolog 2 (colon cancer, nonpolyposis type 1); COCA1 | N | | 2p22-p21 | TTTTAGTGCG GAGGTACGGG | AAACGATCCT TCCGAAACCA AA | 6FAM-CCGCACAAAC ACCAACGTTC CG-BHQ-1 | GenBank Number AC079775; Amplicon Location: 98483-98569 |
| MSH4 | MSH4-M1B | HB-096 | MutS (E. coli) homolog 4 | N | | 1p31 | CGGATTTTAG GAGATTTTAT AGAGTCG | CCGATCGCCC GCAAC | 6FAM-AACGTACCAA AACAAATAAA TACAAAAACC ACCTAAACCG G-BHQ-1 | GenBank Number AL359206; Amplicon Location: 16910-17000 |
| MSH5 | MSH5-M1B | HB-097 | MutS (E. coli) homolog 5 | N | | 6p21.3 | TTCGTGGCGG TCGGTTA | CCGCCATCGC AACGTT | 6FAM-CCCGCCTTTT CAATAACCTA AATCGCTAC A-BHQ-1 | GenBank Number AC020768; Amplicon Location: 68650-68732 |
| MSH6 | MSH6-M1B | HB-084 | MutS (E. coli) homolog 6; GTBP | Y | | 2p16 | GGAGTGTTTC GGTTCGGTTA GT | CTACCGCCGA ACGCCTAAA | 6FAM-CCCTTCCCTC ACGCCGCGA-BHQ-1 | GenBank Number AC006509; Amplicon Location: 34144-34228 |
| MT1A | MT1A-M1B | HB-205 | Metallothionein 1A; MT1S; K01383 | Y | | 16q13 | CGTGTTTTCG TGTTATTGTG TACG | CTCGCTATCG CCTTACCTAT CC | 6FAM-TCCACACCTA AATCCCTTCG ACCCACT-BHQ-1 | GenBank Number AC106779; Amplicon Location: 18175-18254 |
| MT1G | MT1G-M1B | HB-204 | Metallothionein 1G | Y | | 16q13 | CGTTTAAGGG ATTTGTATTT GGTTTAT | CCGCTAAATC CGCACCG | 6FAM-CGCGATCCCG ACCTAAACTA TACGCA-BHQ-1 | GenBank Number AC026461; Amplicon Location: 19549-19625 |
| MT2A | MT2A-M1B | HB-206 | Metallothionein 2A; Metallothionein-II; MT2 | Y | | 16q13 | GCGTTTTCGT CGTGTGTATA GTTT | TTCCCAAATC CGCTTTCA | 6FAM-CGGCGCTAA CGACTCAAAT TCG-BHQ-1 | GenBank Number AC026461; Amplicon Location: 79477-79565 |

TABLE 1-continued (supplementary table 1); Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| MT3 | MT3-M1B | HB-207 | Metallothionien 3 (growth inhibitory factor (neurotrophic)) | Y | N | 16q13 | GGTTTTAGGG TTTATGTCGA GGAGA | CCGCGCGTCC AATTACTTA | 6FAM-AAAACCCGTT CACCGCCTCC AACTACTA-BHQ-1 | GenBank Number AC026461; Amplicon Location: 98167-98241 |
| MTHFR | MTHFR-M1B | HB-058 | 5,10-methylenetetrahydrofolate reductase (NADPH) | N | N | 1p36.3 | TGGTAGTGAG AGTTTTAAAG ATAGTTCGA | CGCCTCATCT TCTCCCGA | 6FAM-TCTCATACCG CTCAAAATCC AAACCG-BHQ-1 | Eads, C. A. et al. Cancer Res 61, 3410-3418 (2001) |
| MUTYH | MUTYH-M1B | HB-088 | MutY (E. coli) homolog; MYH | N | N | 1p34.3-p32.1 | TCGGGTGGAT TCGAGTTACG | AAAATTACCT CCCGCGAACT CTA | 6FAM-CGCGCCCGAC TTTCCGACG-BHQ-1 | GenBank Number AL359540; Amplicon Location: 54075-54149 |
| MYOD1 | MYOD1-M1B | HB-154 | Myogenic determining factor 3; MYF3 | Y | N | 11p15.4 | GAGCGCGCGT AGTTAGCG | TCCGACACGC CCTTTCC | 6FAM-CTCCAACACC CGACTACTAT ATCCGCGAA A-BHQ-1 | Eads, C. A. et al. Cancer Res 61, 3410-3418 (2001) |
| NCL | NCL-M1B | HB-077 | Nucleolin | N | N | 2q12-qter | CGTGTCGTTT CGGTTCGTT | ACCAAAACTC GCGACCGTC | 6FAM-CCATAAACCA ATCGGCGAACC TCTAACCGT-BHQ-1 | GenBank Number M60858; Amplicon Location: 886-975 |
| NEUROD1 | NEUROD1-M1B | HB-259 | Neurogenic differentiation 1; NeuroD; BETA2. BHF-1 | Y | N | 2q32 | GTTTTTTGCG TGGGCGAAT | CCGGCTTAA CATCACTAAC TAAA | 6FAM-CGCGGCACCA CGACACGAA A-BHQ-1 | GenBank Number AC013733; Amplicon Location: 78576-78657 |
| NEUROD2 | NEUROD2-M1B | HB-260 | Neurogenic differentiation 2; NDRF | Y | N | 17q12 | GGTTGGTAT AGAGGTTGGT ATTTCGT | ACGAACGCCG ACGTCTTC | 6FAM-CGCCATACGA ACCGGGAAAC GAATATAA-BHQ-1 | GenBank Number AC087491; Amplicon Location: 38463-38551 |
| NEUROG1 | NEUROG1-M1B | HB-261 | Neurogenin 1 NEUROD3; AKA | Y | Y | 5q23-q31 | CGTGTAGCGT TCGGGTATTT | CGATAATTAC GAACACACTC | 6FAM-CGATAACGAC | GenBank Number AC005738; |

TABLE 1-continued (supplementary table 1): Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| | | | | | | | GTA | CGAAT | CTCCCGCGAA CATAAA-BHQ-1 | Amplicon Location: 75342-75429 |
| NR3C1 | NR3C1-M1B | HB-067 | Glucocorticoid Receptor/Nuclear receptor subfamily 3, group C, member 1; GRL; GR | Y | Y | 5q31 | GGGTGGAAGG AGACGTCGTA G | AACTTCCGA ACGCGCG | 6FAM-GTCCCGATCC CAACTACTTC GACCG-BHQ-1 | GenBank Number AY436590; Amplicon Location: 1786-1861 |
| NTF3 | NTF3-M1B | HB-251 | Neurotrophin 3 | N | | 12p13 | TTTCGTTTTT GTATTTTATG GAGGATT | CCGTTTCCGC CGTAATATTC | 6FAM-TCGCCACCAC GAAACTACCC ACG-BHQ-1 | GenBank Number AC135585; Amplicon Location: 7503-7576 |
| NTHL1 | NTHL1-M1B | HB-089 | Nth (E. coli endonuclease III)-like 1; NTH1; OCTS3 | N | | 16p13.3 | CGGGACGTCG TCGGAAG | CCGACCTTTC CGCCAAA | 6FAM-CGACCCTCCG CGCAATACC G-BHQ-1 | GenBank Number AC005600; Amplicon Location: 24563-24676 |
| OGG1 | OGG1-M1B | HB-087 | 8-oxoguanine DNA glycosylase | N | | 3p26.2 | TAGGGTGGGC GGGTCG | CCGCGAAACG CCCAA | 6FAM-CAATACCGAC CAACCGCGCG A-BHQ-1 | GenBank Number AJ131341; Amplicon Location: 1723-1854 |
| ONECUT2 | ONECUT2-M1B | HB-242 | One cut domain, family member 2. OC-2 | N | | 18q21.1-18q21.2 | ACGGGCGTTA AGCGTAATTA TTT | CCACAACCAC TAATAACTTC CCGTA | 6FAM-CCCGCCTCCC GAAACAACTA CGA-BHQ-1 | GenBank Number AC090340; Amplicon Location: 75559-75639 |
| OPCML[b] | OPCML-M1B | HB-209 | Opioid binding protein/cell adhesion molecule-like; OPCM, OBCAM | Y | | 11q25 | CGTTTCGAGG CGGTATCG | CGAACCGCCG AAATTATCAT | 6FAM-AACAACTCCA TCCCTAACCG CCACTTTCT-BHQ-1 | GenBank Number AC027631; Amplicon Location: 157489-157560 |
| PARP1[c] | PARP1-M1B | HB-093 | Poly (ADP-ribose) polymerase family member 1; PPOL; ADPRT; PARP | N | | 1q41-q42 | CGGGTTTAGG GAGCGAGC | AAACGACCGC GAACCCATA | 6FAM-CGTCCGAAA ACCGACCG AA-BHQ-1 | GenBank Number AL359704; Amplicon Location: 146947-147015 |

TABLE 1-continued (supplementary table 1): Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| PARP2 | PARP2-M1B | HB-094 | Poly(ADP-ribose) polymerase) family, member 2; ADPRTL2 | N | N | 14q11.2-q12 | GGGCGAGAGG TTCGGAGT | TCGTTCCTTT CTAACTACCC GC | 6FAM-CCCGCATACC GTCCCGCGAT A-BHQ-1 | GenBank Number AL355075; Amplicon Location: 176220-176286 |
| PAX8 | PAX8-M2B | HB-211 | Paired Box Gene 8; Paired Domain Gene 8 | N | N | 2q12 | GTTCGTAGTT CGTCGGAGGGT TC | CGCATCTCAT ACCCTTCTCC TAAAT | 6FAM-CAAACGCGAC CCGAACCTAC GAAAA-BHQ-1 | GenBank Number AC016683; Amplicon Location: 115663-115758 |
| PENK | PENK-M1B | HB-163 | ppENK/ Proenkephalin precursor | Y | N | 8q23-q24 | GGTTAATTAT AAAGTGGTTT TAGTAGTCGT TAAG | CAACGTCTCT ACGAAATCAC GAAC | 6FAM-AACGCCTACC TCGCCGTCCC G-BHQ-1 | GenBank Number AC012349; Amplicon Location: 81412-81510 |
| PGR | PGR-M1B | HB-149 | Progesterone Receptor A; PR; NR3C3 | Y | N | 11q22-q23 | GGCGGTGACG GTCGTATTC | ACAAACCGTC CCGCGAA | 6FAM-AACAACCGCTC GCGGCCGA-BHQ-1 | Woodson, K. et al Cancer Epidemiol Biomarkers Prev 14, 1219-1223 (2005) |
| PITX2 | PITX2-M2B | HB-235 | Paired-like homeodomain transcription factor 2; IRID2; IHG2; RIEG; RGS; IGDS | Y | N | 4q25-27 | AGTTCGGTTG CGCGGTT | TACTTCCCTC CCCTACCTCG TT | 6FAM-CGACGCTCGC CCGAACGCT A-BHQ-1 | GenBank Number AC017068; Amplicon Location: 117302-117404 |
| PLAGL1 | PLAGL1-M1B | HB-199 | Pleiomorphic adenoma gene-like 1; LOT1 | N | N | 6q24-q25 | ATCGACGGGT TGAATGATAA ATG | CTCGACGCAA CCATCCCTCTT | 6FAM-ACTACCGCGA ACGACAAAAC CCACG-BHQ-1 | GenBank Number AL109755; Amplicon Location: 52969-53045 |
| PMS2 | PMS2-M1B | HB-098 | Postmeiotic segregation increased 2 (S. cerevisiae); PMSL2 | N | N | 7p22 | TCGTGGTTTG GCGTGGAT | CCTAATACAT CGAAATAACG CGTACC | 6FAM-CCAACGATCG AAAACCGCCA AACA-BHQ-1 | GenBank Number AC005073; Amplicon Location: 150898-150982 |
| POLD1 | POLD1-M1B | HB-139 | Polymerase (DNA directed), delta 1, | N | N | 19q13.3 | GGGACGCGGA GGATGC | GATCTAAACG CCGCGATTCT | 6FAM-TCCTCCCACC | GenBank Number AC073646; |

TABLE 1-continued (supplementary table 1): Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| | | | catalytic subunit (125 kD); POLD | | | | | AT | CTCGAATATT ACGCG-BHQ-1 | Amplicon Location: 123366-123435 |
| PPARG | PPARG-M1B | HB-060 | Peroxisome proliferative activated receptor, gamma isoform 1; PPARG1; PPARG2; NR1C3 | N | | 3p25 | GCGTTCGCGT TCGTTTTC | CGCCCCAAAC GACGAC | 6FAM-CCCGCCTACC CGGACGAA A-BHQ-1 | GenBank Number AC091492; Amplicon Location: 138096-138211 |
| PRKAR1A | PRKAR1A-M1B | HB-214 | protein kinase, cAMP-dependent, regulatory, type I, alpha (tissue specific extinguisher 1); TSE; PRKAR1 | N | | 17q23 | CGGATTTGTA GTAGTTGCGT TGC | ACCGAACACA AAATACGC GAC | 6FAM-CATCCCGACC ATCCGCCCG-BHQ-1 | GenBank Number AC079210; Amplicon Location: 118231-118314 |
| PSAT1 | PSAT1-M1B | HB-231 | Phosphoserine aminotransferase 1 | N | | 9q21 | TGGGTTTGGT TTCGTTAAGT TGT | ACGTACTCCC GCCTAAACCT C | 6FAM-ACGCCCGCTC GCGAAAACTT ACTAAATA-BHQ-1 | GenBank Number AL353594; Amplicon Location: 5511-5591 |
| PSEN1 | PSEN1-M1B | HB-262 | Presenilin 1 (Alzheimer disease 3); AD3 | N | | 14q24.3 | GTCGGGTGGA GAGAGATTTC G | AACACCTACG GCCCTAAAA CGTC | 6FAM-TCGAACAAAC AACATTTCCG AACCAAAAC T-BHQ-1 | GenBank Number AF205592; Amplicon Location: 6663-6739 |
| PSEN2 | PSEN2-M1B | HB-262 | Presenilin 2 (Alzheimer disease 4); AD4 | N | | 1q31-q42 | GAGGGCGTGTA GTAGGCGGG | CCGATACTAA AAACCGAATA AACTCG | 6FAM-CGCAACGAAA ATCTCCGACG AAAAAA-BHQ-1 | GenBank Number U50871; Amplicon Location: 26196-26284 |
| PTEN | PTEN-M1B | HB-157 | Phosphatase and tensin homolog (mutated in multiple advanced cancers 1); MMAC1; BZS; MHAM | N | | 10q23.3 | GTTTCGCGTT GTTGTAAAAG TCG | CAATATAACT ACCTAAAACT TACTCGAACC G | 6FAM-TTCCCAACCG CCAACTACA ACTACACTT A-BHQ-1 | GenBank Number AF143312; Amplicon Location: 1060-1147 |
| PTGS2 | PTGS2-M1B | HB-065 | prostaglandin-endoperoxide synthase 2 (prostaglandin G/H | N | | 1q25.2-q25.3 | CGGAAGCGTT CGGGTAAAG | AATTCCACCG CCCCAAAC | 6FAM-TTTCCGCCAA ATATCTTTTCT TCTTCGCA- | Fiegl, H. et al Cancer Epidemiol Biomarkers |

TABLE 1-continued (supplementary table 1); Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| | | | synthase and cyclooxygenase); COX2 | | | | | | BHQ-1 | Prev 13, 882-888 (2004) |
| PTTG1 | PTTG1-M1B | HB-052 | Pituitary tumor-transforming 1; TUTR1; SECURIN; PTTG; HPTTG | N | | 5q35.1 | GCGTTCGTTT ATCGCGGT | CCGCGACCC TCCCATT | 6FAM-ACTCACGCAA ATCTTAACAA CCGCATTCA-BHQ-1 | GenBank Number AC091842; Amplicon Location: 88212-88281 |
| PYCARD | PYCARD-M1B | HB-228 | PYD and CARD domain containing ASC; TMS1; CARD5; MGC10332 | Y | | 16p12-p11.2 | TTGGAGATTT ACGGCGTCG | ACCCTAATAC GTACCGCCT ACAA | 6FAM-CATCTCCTAC AAACCCATAT CGGGCAA-BHQ-1 | GenBank Number AC009088; Amplicon Location: 85330-85425 |
| RAD23A | RAD23A-M1B | HB-101 | RAD23 (S. cerevisiae) homolog A; HHR23A | N | | 19p13.2 | TATCGATAAC GGGTATGGCG TT | GCAAACTAAA CTCCGCGCTA TAA | 6FAM-TTACTCGACCC GCACACGTAAT CTCCTAAA-BHQ-1 | GenBank Number AD000092; Amplicon Location: 92213-92298 |
| RARB | RARB-M1B | HB-176 | retinoic acid receptor, beta; HAP; RRB2; NR1B2 | Y | | 3p24 | TTTATGCGAG TTGTTTGAGG ATTG | CGAATCCTAC CCCGACGATA C | 6FAM-CTCGAATCGC TCGCGTTCTC GACAT-BHQ-1 | GenBank Number X56849; Amplicon Location: 921-1006 |
| RARRES1 | RARRES1-M1B | HB-322 | Retinoic acid receptor, responder (tazarotene induced) 1; TIG1 | Y | | 3q25.31-3q26.1 | GGGCGAGTCGG ATCGGAA | CGCAAACTCC TACAACAAAC GA | 6FAM-CGCGGACGC TTCACTTCTT CAA-BHQ-1 | GenBank Number AC080013; Amplicon Location: 66080-66144 |
| RASSF1 | RASSF1A-M1B | HB-044 | Ras association (RalGDS/AF-6) domain family 1; NORE2A; REH3P21; RDA32 | Y | | 3p21.3 | ATTGAGTTGC GGGAGTTGGT | ACACGCTCCA ACCGAATACG | 6FAM-CCCTTCCCAA CGCGCCCA-BHQ-1 | Previously described as RASSF1A in Ehrlich, M. et al. Oncogene 21, 6694-6702 (2002) |
| RB1 | RB1-M1B | HB-245 | Retinoblastoma 1 (including osteosarcoma); OSRC | N | | 13q14.2 | TTAGTTCGCG TATCGATTAG CG | ACTAAACGCC GCGTCCAA | 6FAM-TCACGTCCGC GAAACTCCCG A-BHQ-1 | Eads, C. A. et al. Cancer Res 61, 3410-3418 (2001) |

TABLE 1-continued (supplementary table 1); Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| RBP1 | RBP1-M1B | HB-185 | Retinol binding protein 1, cellular | Y | N | 3q23 | CGCGTTGGGA ATTTAGTTGT C | GATACTACGC GAATAATAAA CGACCC | 6FAM-ACGCCCTCCG AAACAAAAA ACTCTACG-BHQ-1 | GenBank Number AC046134; Amplicon Location: 137423-137512 |
| RNR1 | RNR1-M1B | HB-071 | Ribosomal RNA | N | N | 13p12 | CGTTTTGGAG ATACGGGTCG | AAACAACGCC GAACCGAA | 6FAM-ACCGCCCGTA CCACACGCAA A-BHQ-1 | Muller, H. M. et al. Cancer Lett209, 231-236 (2004) |
| RPA2 | RPA2-M1B | HB-103 | Replication protein A2 (32 kD) | Y | N | 1p35 | TGGCGCGAAT TTGAGTACG | CGTATAATCC CACCCTCGTC A | 6FAM-CGCGACTTCT ACCGTCACTT CCTTTATTC G-BHQ-1 | GenBank Number AL109927; Amplicon Location: 71845-71919 |
| RPA3 | RPA3-M1B | HB-104 | Replication protein A3 (14 kD) | Y | N | 7p22 | AGCGCGATTG CGATTTAGG | TTTCTCGACA CCAATCAACG AA | 6FAM-TCCAACTTCG CCAATTAAAT ACGCGAAA-BHQ-1 | GenBank Number AC004948 Amplicon Location: 23978-24056 |
| RUNX3 | RUNX3-M1B | HB-181 | Runt-related transcription factor 1 (acute myeloid leukemia 1; aml1 oncogene); CBFA3; AML2 | Y | Y | 1p36 | CGTTCGATGG TGGACGTGT | GACGAACAAC GTCTTATTAC AACGC | 6FAM-CGCACGAACT CGCCTACGTA ATCCG-BHQ-1 | GenBank Number AL023096; Amplicon Location: 64646-64762 |
| S100A2 | S100A2-M1B | HB-061 | S100 calcioum binding protein A2; S100L; CAN19 | N | N | 1q21 | TGTTTGAGTC GTAAGTAGGG CGT | CGTATCATTA CAATACCGAC CTCCT | 6FAM-ATCCTCCCTT TCTTATCCGC CAAACCCT-BHQ-1 | Muller, H. M. et al. Cancer Lett209, 231-236 (2004) |
| SASH1 | H-SASSH1-M1B | HB-220 | SAM and SH3 domain containing; KIAA0790 | N | N | 6q23 | TGGAAGAGTT TATTTTGAAG AGAGGG | GCGACTCGTT CCTTCTAACA AATC | 6FAM-AAACCCGACA AAAATAACCG CGAAACCT-BHQ-1 | GenBank Number AL513164; Amplicon Location: 97419-97530 |
| SCAM-1 | SCAM-1-M1B | HB-064 | Vinexin beta (SH3-containing adaptor molecule-1 | Y | N | 8p21 | GTTTCGGTTG TCGTTGGGTT | ACGCCGACGA ACTCTACGC | 6FAM-ACGACGCAAT CAAAACCCGC | GenBank Number AC037459; Amplicon |

TABLE 1-continued (supplementary table 1): Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| | | | | | | | | | GA-BHQ-1 | Location: 86568-86640 |
| SCGB3A1 | SCGB3A1-M1B | HB-194 | Secretoglobin family 3A, member 1; HIN-1; HIN1; LU105; UGRP2 | Y | N | 5q35-qter | GGCGTAGCGG GCGTC | CTACGTAACC CTATCCTACA ACTCCG | 6FAM-CGAACTCCTA ACGCGCACGA TAAACCTA-BHQ-1 | GenBank Number AC122714; Amplicon Location: 80825-80911 |
| SERPINB5 | SERPINB5-M1B | HB-208 | Serine (or cysteine) proteinase inhibitor, clade B (ovalbumin), member 5; PI5; MASPIN | N | N | 18q21.3 | GAAAAGGAAT AGGTAAGCGA GGAGT | ATAAACCACC GCTACTTCTA CCCA | 6FAM-CACGATGCC TCCACATCCA AATCTTT-BHQ-1 | GenBank Number AC036176; Amplicon Location: 51709-51788 |
| SEZ6L | SEZ6L-M1B | HB-184 | Seizure related 6 homolog (mouse)-like; KIAA0927 | Y | N | 22q12.1 | GCGTTAGTAG GGAGAGAAAA CGTTC | ATACCAACCG CCTCCTCTAA CC | 6FAM-CCGTCGACCC TACAAAATTT AACGCCA-BHQ-1 | GenBank Number AL022337; Amplicon Location: 87324-87426 |
| SFN | SFN-M1B | HB-174 | Stratifin; 14-3-3 sigma | N | N | 1p35.3 | GAGGAGGGTT CGGAGAGAA | ATCGCACACG CCCTAAAACT | 6FAM-TCTCCCGATA CTACGGCACC TCGAA-BHQ-1 | GenBank Number AF029081; Amplicon Location: 8848-8928 |
| SFRP1 | SFRP1-M1B | HB-201 | Secreted frizzled-related protein 1; FRP-1; SARP2 | Y | N | 8p12-p11.1 | GAATTCGTTC GCGAGGGA | AAACGAACCG CACTCGTTAC C | 6FAM-CCGTCACCGA CGCGAAAACC AAT-BHQ-1 | GenBank Number AC104393; Amplicon Location: 1133-1202 |
| SFRP2 | SFRP2-M2B | HB-280 | Secreted frizzled-related protein 2; FRP-2; SARP1; SDF-5 | Y | N | 4q31.3 | GCGTTTTAGT CGTCGTTGT TAGT | AAACGACCGA AATTCGAACT TATC | 6FAM-CGAACCCGCT CTCTTCGCTA AATACGA-BHQ-1 | GenBank Number AC020703; Amplicon Location: 71046-71137 |
| SFRP4 | SFRP4-M1B | HB-281 | Secreted frizzled-related protein 4; FRP-4 | Y | N | 7p14-p13 | GTTGTTCGGG CGGGTTC | GCGAAACTCC GCCGTCTA | 6FAM-AAACACGAAC AACGCCAACT CTCAACCT-BHQ-1 | GenBank Number AC018634; Amplicon Location: 76448-76526 |

TABLE 1-continued (supplementary table 1); Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| SFRP5 | SFRP5-M1B | HB-282 | Secreted frizzled-related protein 5; SARP3 | Y | N | 10q24.1 | GCGTTTGTAG TTTATCGTGT GGTAGA | GAACCGCTAC ACGACCGCT | 6FAM-CGCCGCAATA CCTTAACATC CCTACCG-BHQ-1 | GenBank Number AL358938; Amplicon Location: 45204-45296 |
| SLC6A20 | SLC6A20-M1B | HB-079 | solute carier family 6 (proline IMINO transporter), member 20; XT3 | Y | N | 3p21.3 | AGGCGAATAC GAATTGTAGC G | TAAAACGACG CGCCTAACG | 6FAM-CCCGCGACTA AAACTACCGT ACCGAA-BHQ-1 | GenBank Number AJ289880 Amplicon Location: 85407-85541 |
| SMAD2 | SMAD2-M1B | HB-275 | SMAD, mothers against DPP homolog 2 (Drosophila); MADH2 | N | N | 18q21.1 | CGAGGCGGTA GGTTTTTATA GGT | CGCATTAAAA CGATTCCCGA T | 6FAM-CCGATCCCTC GCCAACGTCG TAA-BHQ-1 | GenBank Number AC120349; Amplicon Location: 27348-27425 |
| SMAD3 | SMAD3-M1B | HB-053 | SMAD, mothers against DPP homolog 3 (Drosophila); MADH3 | N | N | 15q22-15q23 | CGTGAAGCGT TTGTTGGGT | TTAACCGCCT TCTCGCACC | 6FAM-TCCTCCTACC CGTTCTACTC GCCCTTCTT-BHQ-1 | Previously described as MADH3 in Ehrlich, M. et al. Oncogene 21, 6694-6702 (2002) |
| SMAD4 | SMAD4-M1B | HB-277 | SMAD, mothers against DPP homolog 4 (Drosophila); MADH4; DPC4 | N | N | 18q21.1 | GTTTGCGTAG AGCGATTTTT TTC | GCAACTTTCC TTTCTCCCGA CT | 6FAM-CCCGCCTCCC GCTCCGAAT A-BHQ-1 | GenBank Number AB043547; Amplicon Location: 119423-119492 |
| SMAD6 | SMAD6-M1B | HB-278 | SMAD, mothers against DPP homolog 6 (Drosophila); MADH6; Hs17432 | Y | N | 15q21.3-22.2 | ATGTTAGTTT AGATATTTTG GCGGTTTC | CGACCCTACA ATAAAACGTA TTCTCCT | 6FAM-AAACCTTATT TACGCAACAA TCAACGCCG-BHQ-1 | GenBank Number AC013564; Amplicon Location: 57206-57309 |
| SMAD9 | SMAD9-M1B | HB-315 | SMAD, mothers against DPP homolog 9 (Drosophila); MADH9 | N | N | 13q12-q14 | CGCGAAGTTT TATCGTTCGT ATTAG | CGAAAACGAA CCGCAAACA | 6FAM-AACTCCCTAA CCGCTTTCCA AATCGACG-BHQ-1 | GenBank Number AL138706; Amplicon Location: 77288-77362 |
| SMUG1 | SMUG1-M1B | HB-086 | Single-strand selective monofunctional | N | N | 12q13.11-q13.3 | GGATTATAGG CGCGCGTTAT T | TCACACCCGT AATCCGAACA | 6FAM-ACCGAAACGA ACGAATACACG | GenBank Number AC023794; Amplicon |

TABLE 1-continued (supplementary table 1): Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| | | | uracil DNA glycosylase | | | | | | AAATCAAA-BHQ-1 | Location: 156022-156167 |
| SOCS1 | SOCS1-M1B | HB-042 | Suppressor of cytokine signaling 1; SPCS-1; SSI-1; JAB; TIP3; Cish1 | Y | Y | 16p13.13 | GCGTCGAGTT CGTGGGTATT T | CCGAAACCA TCTTCACGC TAA | 6FAM-ACAATTCCGC TAACGACTAT CGGCA-BHQ-1 | Fiegl, H. et al Cancer Epidemiol Biomarkers Prev 13, 882-888 (2004) |
| STAT1 | STAT1-M1B | HB-063 | Signal transducer and activator of transcription 1, 91 kDa; STAT91 | N | N | 2q32.2 | GCGTAGGATT CGGAAGGGTT A | AACAAACCC CAAACCGAA CA | 6FAM-AACGACCCAA CGCGCTCGAA AA-BHQ-1 | GenBank Number AY865620; Amplicon Location: 2091-2179 |
| STK11 | STK11-M2B | HB-183 | Serine/threonine kinase 11 (Peutz-Jeghers syndrome); PJS; LKB1 | N | N | 19p13.3 | AATTAACGGG TGGGTACGTC G | GCCATCTTAT TTACCTCCCT CCC | 6FAM-CGCACGCCCG ACCGCAA-BHQ-1 | GenBank Number AC011544; Amplicon Location: 26084-26187 |
| SYK | SYK-M2B | HB-241 | Spleen tyrosine kinase | N | N | 9q22 | AGGGTCGTTG GGTGTTTGTG | AACATAAACC GCATCGATCC C | 6FAM-CGCCAACGCG ATAACTTCTA TAACTACCC AA-BHQ-1 | GenBank Number AL354862; Amplicon Location: 50529-50613 |
| TERT | TERT-M1B | HB-074 | Telomerase reverse transcriptase; TRT; TPS; TCS1; EST2 | Y | N | 5p15.33 | GGATTCGCGG GTATAGACGT T | CGAAATCCGC GCGAAA | 6FAM-CCCAATCCCT CCGCCACGTA AAA-BHQ-1 | Fiegl, H. et al Cancer Epidemiol Biomarkers Prev 13, 882-888 (2004) |
| TFAP2A | TFAP2A-M1B | HB-314 | Transcription factor AP-2 alpha (activating enhancer binding protein 2 alpha); AP-2; TFAP2; AP2TF | Y | N | 6p24 | CGTTAATTTT TAAAGTATTT TTATGGATCG | CCGACAACCA ACACTTTACG C | 6FAM-CGAAAACCGAA AAAAACATAT CCGTTCACG-BHQ-1 | GenBank Number AL138885; Amplicon Location: 105985-106093 |

TABLE 1-continued (supplementary table 1): Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| TFF1 | TFF1-M1B | HB-145 | Trefoil factor 1 (breast cancer; estrogen-inducible sequence expressed in); BCE1; D21S21 | N | | 21q22.3 | TAAGGTTACG GTGGTTATTT CGTGA | ACCTTAATCC AAATCCTACT CATATCTAAA A | 6FAM-CCCTCCCGCC AAAATAAATA CTATACTCAC TACAAAA-BHQ-1 | Fiegl, H. et al Cancer Epidemiol Biomarkers Prev 13, 882-888 (2004) |
| TGFBR1 | TGFBR1-M1B | HB-192 | Transforming growth factor, beta receptor I (activin A receptor) type II-like kinase, 53kDa); ALK-5 | N | | 9q22 | ACGCGCGTTT ATTGGTTGTC | ACGAACCCGC AAACGAAA | 6FAM-TAAATCCCGC TTAACAACTC GCGACGA-BHQ-1 | GenBank Number AL162427; Amplicon Location: 88267-88365 |
| TGFBR2 | TGFBR2-M1B | HB-246 | Transforming growth factor, beta receptor II (70/80 kDa); MFS2 | N | | 3p22 | GCGCGGAGCG GTAGTTAGG | CAAACCCCGC TACTCGTCAT | 6FAM-CACGAACGAC GCCTTCCCGA A-BHQ-1 | Eads, C. A. et al. Cancer Res 61, 3410-3418 (2001) |
| THBS1 | THBS1-M1B | HB-247 | Thrombospondin 1; TSP1 | N | | 15q15 | CGACGCACCA ACCTACCG | GTTTTGAGTT GGTTTTACGT TCGT | 6FAM-ACGCCGCGCT CACCTCCCT-BHQ-1 | Widschwendter, M. et al Cancer Res 64, 3807-3813 (2004) |
| THRB | THRB-M1B | HB-247 | Thyroid hormone receptor, beta (erythroblastic leukemia viral (v-erb-a) oncogene homolog 2, avian); ERBA2; THRB1; THRB2; NR1A2 | Y | | 3p24.3 | TCGTCGTCGT TATCGTCGC | GCGTCTACGA ACCGATAACC TAAT | 6FAM-CCCTCCAACC CTCACGACTA TCCGACTTA-BHQ-1 | GenBank Number AC012087; Amplicon Location: 123758-123833 |
| TIMP3 | TIMP-3 | HB-167 | TIMP metallopeptidase inhibitor 3 (Sorsby fundus dystrophy, pseudoinflaminatory); SFD | Y | | 22q12.3 | GCGTCGGAGG TTAAGGTTGT T | CTCTCCAAAA TTACCGTACG CG | 6FAM-AACTCGCTCG CCCGCCGAA-BHQ-1 | Eads, C. A. et al. Cancer Res 61, 3410-3418 (2001) |
| TITF1 | TITF1-M1B | HB-213 | Thyroid transcription factor 1; NKX2A; BCH; TTF-1 | Y | | 14q13 | CGAAATAAAC CGAATCCTCC TTAA | TGTTTTGTTG TTTTAGCGTT TACGT | 6FAM-CTCGCGTTTA TTTTAACCCG ACGCCA-BHQ-1 | Fiegl, H. et al Cancer Epidemiol Biomarkers Prev 13,882-888 (2004) |

TABLE 1-continued (supplementary table 1): Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| TMEFF2 | TMEFF2-M1B | HB-274 | Transmembrane protein with EGF-like and two follistatin-like domains 2; TENB2 | Y | N | 2q32.3 | CGACGAGGAG GTGTAAGGAT G | CAACGCCTAA CGAACGAACC | 6FAM-TATAACTTCC GCGACCGCCT CCTCCT-BHQ-1 | GenBank Number AC092644; Amplicon Location: 149017-149089 |
| TNFRSF10A | TNFRSF10A-M1B | HB-306 | Tumor necrosis factor receptor superfamily, member 10a; DR4; Apo2; TRAILR-1; CD261 | N | N | 8p21 | AGTTTTTGGT ATTTAGTAGG CGTTCG | CAAACCCCGC AATAACCTCT ATATC | 6FAM-ATTCCGCCAC CCATCCGTCC A-BHQ-1 | GenBank Number AC100861; Amplicon Location: 53847-53923 |
| TNFRSF10B | TNFRSF10B-M1B | HB-307 | Tumor necrosis factor receptor superfamily, member 10b; DR5; KILLER; TRICK2A; TRAIL-R2; TRICKB; CD262 | N | N | 8p22-p21 | TTTTGGCGGT TGCGTTTC | CTCATTTCCC CCAAATTTCG AT | 6FAM-ATCCTAACGC GAACAAAACC CAAAAACAA-BHQ-1 | GenBank Number AC107959; Amplicon Location: 131919-132001 |
| TNFRSF10C | TNFRSF10C-M1B | HB-308 | Tumor necrosis factor receptor superfamily, member 10c, decoy without an intracellular domain; DcR1; TRAILR3; LIT; TRID; CD263 | Y | N | 8p22-p21 | GGGAAGAGCG TATTTGGCG | TCCCCTAACT CCGACGACG | 6FAM-CGAACATACC CGACCGCAAA TAACCA-BHQ-1 | GenBank Number AC107959; Amplicon Location: 165904-166026 |
| TNFRSF10D | TNFRSF10D-M1B | HB-309 | Tumor necrosis factor receptor superfamily, member 10d, decoy with truncated death domain; DcR2; TRUNDD; TRAILR4; CD264 | N | N | 8p21 | GGGAAGAGCG TATTTGGCG | TCCCCTAACT CCGAGGACG | 6FAM-TACCCGACCG CAAACGACCC G-BHQ-1 | GenBank Number AC100861; Amplicon Location: 115508-115632 |
| TNFRSF25 | TNFRSF25-M1B | HB-080 | TNF receptor superfamily, member 25, TNFRSF12; DR3; APO-3 | N | N | 1p36.2 | GCGGAATTAC GACGGGTAGA | ACTCCATAAC CCTCCGACGA | 6FAM-CGCCCAAAAA CTTCCCGACT CCGTA-BHQ-1 | Formerly described as TNFRSF12 in Ehrlich, M. et al. Oncogene 21, 6694-6702 (2002) |
| TP53 | TP53-M1B | HB-217 | Tumor protein p53 | N | N | 17p13.1 | TTTGTTGTCG CGGGATTTC | CGAATTCCGT AAATCGCCC | 6FAM-TAATCCGAAA TACGACGACC AATCGAAAA C-3'BHQ | GenBank Number AC087388; Amplicon Location: 66667-66749 |

TABLE 1-continued (supplementary table 1): Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| TP73 | TP73-M1B | HB-177 | Tumor protein p73 | Y | N | 1p36.3 | GGGTCGGGTAGTTCGTTTTG | CGATTTCGCTACGTCCCCT | 6FAM-AACCTCCGAACGAATACGCGAACGAA-BHQ-1 | GenBank Number AF235000; Amplicon Location: 3977-4058 |
| TSHR[d] | TSHR-M1B | HB-141 | Thyroid stimulating hormone receptor; LGR3 | Y | N | 14q31 | TTGAGGGTTAGAGGCGGGTA | ACAACGAAAATCCTCCTCCAAAAATACA | 6FAM-AACGACGACTTCGACCGCACCG-BHQ-1 | GenBank Number AC010072; Amplicon Location: 103024-103110 |
| TWIST1 | TWIST1-M1B | HB-047 | Twist homolog (acrocephalosyndactyly 3; Saethre-Chotzen syndrome) (Drosophila) | Y | N | 7p21.2 | GTAGCGCGGCGAACGT | AAACGCAACGAATCATAACCAAC | 6FAM-CCAACGCACCCAATCGCTAAACGA-BHQ-1 | Muller, H. M. et al. Cancer Lett 209, 231-236 (2004) |
| TYMS | TYMS-M1B | HB-248 | Thymidylate Synthase | N | N | 18p11.32 | CGGCGTTAGGAAGGACGAT | TCTCAAACTATAACGCGCCTACAT | 6FAM-CCGAATACCGACAAAATACCGATACCCGT-BHQ-1 | Eads, C. A. et al. Cancer Res 61, 3410-3418 (2001) |
| UNG | UNG-M1B | HB-082 | Uracil-DNA glycosylase DGU; UDG; UNG1 | N | N | 12q23-q24.1 | GTTTGACGGAGGGCGTGTA | ACAACGACGACTATTTTAAACACGTAA | 6FAM-CCCGAATTTACCGAATCAAAAACGCGA-BHQ-1 | GenBank Number AC007637; Amplicon Location: 4765-4860 |
| UQCRH | UQCRH-M1B | HB-224 | Ubiquitinol cytochrome c reductase hinge protien | N | N | 1p33.1 | TTCGGTTTCGGGTTTTAACG | CCCATATAAACGCTCACCGC | 6FAM-CCCGCACAACTCGAACAAAAGAAA-BHQ-1 | GenBank Number AL122001; Amplicon Location: 120731-120802 |
| VDR | VDR-M1B | HB-068 | Vitamin D (1,25-dihydroxy vitamin D3) receptoR; NR1I1 | N | N | 12q12-q14 | ACGTATTTGGTTTAGGCGTTCGTA | CGCTTCAACCTATATTAATCGAAAATACA | 6FAM-CCCACCCTTCCTACCGTAATTCTACCCAA-BHQ-1 | Muller, H. M. et al. Cancer Lett 209, 231-236 (2004) |
| VHL | VHL-M1B | HB-191 | Von Hippel-Lindau syndrome tumor | N | N | 3p26-p25 | CGGGAGCGCGTACGTAGTT | CTCCGAAACATTCCCTCCG | 6FAM-CGAACCGAAC | GenBank Number AF010238; |

TABLE 1-continued (supplementary table 1); Complete list of all MethyLight™ reactions.

| HUGO Gene Name (If Available) | Reaction ID | Reaction Design Code | Aliases | Cancer Specific? (Y/N) | 14 CIMP and 5 Toyota Markers? (Y/N) | Chromosomal Location | Forward Primer Sequence | Reverse Primer Sequence | Probe Oligo Sequence[a] | Source |
|---|---|---|---|---|---|---|---|---|---|---|
| | | | suppressor; VHL1 | | | | | | GCCGCGAAA-BHQ-1 | Amplicon Location: 632-725 |
| XAB2 | XAB2-M1B | HB-115 | XPA binding protein 2; HCNP | N | N | 19p13.2 | GACGGATAGG TTTACGTTAT TGATTTT | CGCATCTTCT AACGCCTCTA TTC | 6FAM-ACTTCCGATC GCTAACGTCG TCGAAA-BHQ-1 | GenBank Number AC008763; Amplicon Location: 60446-60523 |
| XPA | XPA-M1B | HB-102 | Xeroderma pigmentosum, complementation group A; XPAC; XP1 | N | N | 9q22.3 | CGCGGAGTTG TTTGTTTCG | CAACATCAAT ACCCGCTACC G | 6FAM-CCGCTCGATA CTCGCCCGC A-BHQ-1 | GenBank Number AL445531; Amplicon Location: 26708-26771 |
| XpC | XPC-M1B | HB-100 | Xeroderma pigmentosum, complementation group C; XPCC | N | N | 3p25.3 | GTCGGGTGCG TTATTCGC | CTACGCAATT CGCGTCCC | 6FAM-ACCGCGCGTT TCCGAACCAT ATTACT-BHQ-1 | GenBank Number AC093495 Amplicon Location: 81528-81625 |
| XRCC1 | XRCC1-M1B | HB-092 | X-ray repair complementing defective repair Chinese hamster cells; RCC | N | N | 19q13.2 | CGTTGTTAAG GAACGTAGCG TTTT | GCGCGAAACT TCGAACCTTT | 6FAM-CCAATCGCGC CTCTCCAAAA CG-BHQ-1 | GenBank Number L34079; Amplicon Location: 4045-4154 |
| COL2A1 | COL2A1-C1B | HB-057 | Collagen, type II, alpha 1 (primary osteoarthritis, spondyloepiphyseal dysplasia, congenital) | N/A | N/A | 12q13.11-q13.2 | TCTAACAATT ATAAACTCCA ACCACCAA | GGGAAGATGG GATAGAAGGG AATAT | 6FAM-CCTTCATTCT AACCCAATAC CTATCCCACC TCTAAA-BHQ-1 | Widschwendter, M. et al Cancer Res 64, 3807-3813 (2004) |
| ALU | ALU-C4M | HB-313 | Interspersed ALU repeat sequence | N/A | N/A | N/A | GGTTAGGTAT AGTGGTTTAT ATTTGTAATT TTAGTA | ATTAACTAAA CTAATCTTAA ACTCCTAACC TCA | 6FAM-CCTACCTTAA CCTCCC-MGBNFQ | Weisenberger D. J. et al Nucleic Acids Res 33, 6823-6836 (2005). |

TABLE 2

(supplemental table 2). New CIMP Classification Panel. The first five
reactions are methylation-specific, bisulfite conversion-specific
markers that together form the new diagnostic panel used for CIMP
classification. Putative DNA methylation sites (CpGs indicated as
"CG" in the sequence) are indicated in bold in the oligonucleotide
sequences. The sixth reactions is a non-methylation-specific,
bisulfite-conversion-specific normalization reactions used to
calculate PMR values.

| HUGO NAME | RXN ID | PURPOSE | FORWARD PRIMER | REVERSE PRIMER | PROBE |
|---|---|---|---|---|---|
| CACNA1G | HB-158 | CIMP Marker | TTTTTTCGTTTCGCGTTTAGGT | CTCGAAACGACTTCGCCG | 6FAM-AAATAACGCCGAATCCGACAACCGA-BHQ |
| IGF2 | HB-319 | CIMP Marker | GAGCGGTTTCGGTGTCGTTA | CCAACTCGATTTAAACCGACG | 6FAM-CCCTCTACCGTCGCGAACCCGA-BHQ |
| NEUROG1 | HB-261 | CIMP Marker | CGTGTAGCGTTCGGGTATTTGTA | CGATAATTACGAACACACTCCGAAT | 6FAM-CGATAACGACCTCCCGCGAACATAAA-BHQ-1 |
| RUNX3 | HB-181 | CIMP Marker | CGTTCGATGGTGGACGTGT | GACGAACAACGTCTTATTACAACGC | 6FAM-CGCACGAACTCGCCTACGTAATCCG-BHQ-1 |
| SOCS1 | HB-042 | CIMP Marker | GCGTCGAGTTCGTGGGTATTT | CCGAAACCATCTTCACGCTAA | 6FAM-ACAATTCCGCTAACGACTATCGCGCA-BHQ-1 |
| ALU | HB-313 | Normalization control | GGTTAGGTATAGTGGTTTATATTTGTAATTTTAGTA | ATTAACTAAACTAATCTTAAACTCCTAACCTCA | 6FAM-CCTACCTTAACCTCC-MGBNFQ |

Example 2

Cancer-Specific DNA Methylation Markers were Selected

The initial (original) definition of CIMP was based on concordant methylation of Type C loci, and specifically excluded markers that showed evidence of age-associated methylation in normal tissues, referred to as "Type A" loci[1]. Therefore, applicants performed a first screen of all 195 unique MethyLight™ markers available in applicants' laboratory against ten colorectal normal-tumor pairs (TABLE 1; under Methods above) to eliminate markers that did not show evidence of tumor-associated methylation. To avoid bias either for or against markers associated with CIMP, five tumors previously characterized as CIMP+ (see Methods above; "Tissue Samples") were used, and five CIMP– tumors, and only those markers that failed to show tumor-specific methylation in either of the two groups of tumors (FIG. 1) were eliminated. It is important to note that this initial filter did not introduce a bias for or against CIMP. It merely eliminated the 103 markers that would not be informative in subsequent analyses since they are not tumor-specifically methylated (see Methods above "Selection of Type C Markers" and FIG. 1).

Three criteria were used to select markers for further evaluation. The excluded markers represent the 105 markers shown at the top, while included markers refer to the lower 92 markers in FIG. 2. First, any marker, for which the highest PMR value among these 20 samples was not at least 2 was excluded. Second, any marker for which the mean PMR for tumor samples was at least twice that of normal samples was included. Third, any marker for which all normal samples had a PMR<2, and for which all tumor samples had a PMR>2 was included. Both the second and third criteria were applied separately to both the CIMP+ tumors and CIMP– tumors, and to all ten cases collectively. A marker was included if it passed at least one of the two criteria in any of the three sample comparisons. This resulted in a collection of 92 reactions that passed this first relaxed screen for tumor-specificity. Among these 92 reactions were five methylation markers (CDKN2A (p16), MLH1, MINT1, MINT2, and MINT31) that have been commonly used to define CIMP status.

Example 3

CIMP-Specific DNA Methylation Markers were Selected

Figure 2:
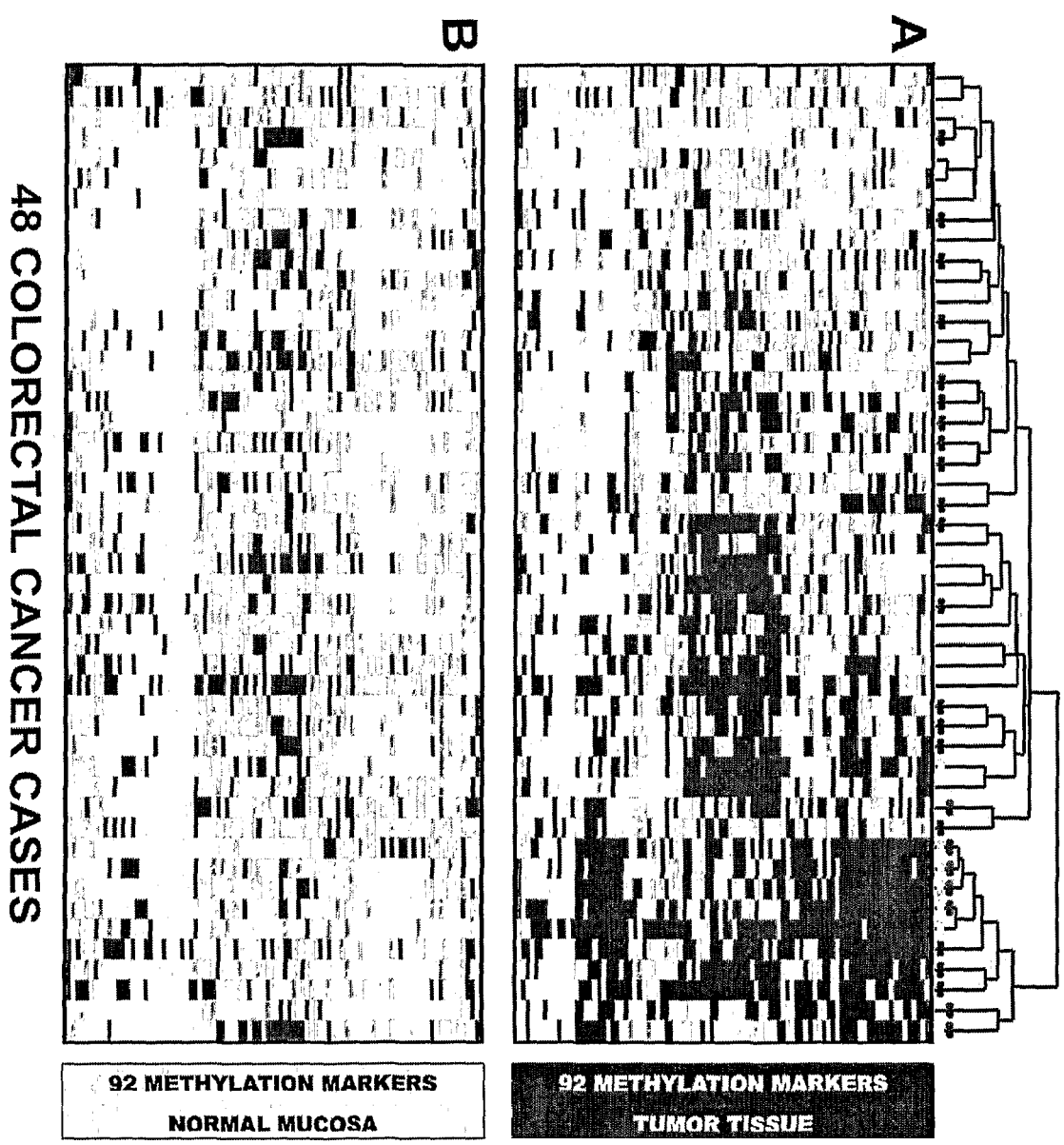
FIG. 2 shows identification of tumor clusters. Hierarchical cluster analysis of DNA samples from 48 colorectal tumor and matched normal mucosae and 92 methylation markers, performed as described in Methods (Example 1). Clustering of the cases was based on the tumor methylation data shown in the upper heatmap (Panel A). The resulting dendrogram of the cases is shown at the top, with tumors containing KRAS mutation indicated by a red rectangle overlaying the branch, while BRAF mutations are indicated by a green rectangle, and MSI-H cases are designated with a blue rectangle. Clustering of the methylation markers was performed separately for the matched normal mucosal samples (Panel B). DNA methylation quartiles are shown from very light blue-white (lowest), through light yellow (next lowest), dark yellow (third lowest) to dark red (highest methylation quartile.

Applicants next determined the methylation status of the remaining 92 tumor-specific markers in 48 independent colorectal cancer cases, and conducted a hierarchical two-dimensional unsupervised clustering of the data in order to assess if distinct subsets of methylation behavior among groups of tumors would emerge (FIG. 2). A well-defined subgroup of tumors is evident on the right-hand side of the dendrogram. Other cluster analyses, such as an index of the number of methylated loci, a Gaussian mixture model, and partitioning around medioids (PAM)[7,8] all yielded similar results (see Methods). Although applicants argue above that the initial screen that gave rise to the 92 markers used in this cluster analysis was unbiased with respect to CIMP, applicants sought additional evidence to support this contention by repeating the initial screen in FIG. 1 using only CIMP– tumors, and then repeating the cluster analysis using the resulting 50 markers. This analysis identified the same clusters as the entire subset of 92 markers. Therefore, tumor-specific markers that were selected using only CIMP– tumors were able to correctly resolve the distinct cluster, indicating that the CIMP cluster is not an anomaly caused by a bias introduced by the inclusion of CIMP+ tumors in the initial filter. Since many of the classic CIMP markers, such as CDKN2A (p16), MINT1, MINT2, MINT31, and MLH1[1,2] are more frequently methylated in the distinct subset of tumors on the right side of the dendrogram, applicants conclude that this cluster is similar to the CIMP+grouping originally identified on the basis of bimodal distribution of methylation frequency by Toyota et al.[1,2].

It is interesting to note that a different subset of CpG islands located near the center of the tumor heatmap in FIG. 2 appears to be more frequently methylated in tumor samples that do not belong to the CIMP cluster, but nevertheless show increased methylation in tumor samples compared to their matched normal mucosal counterparts. Inclusion of such markers in panels used to define CIMP could reduce the classification power of the panel, and possibly even lead one to conclude that CpG island hypermethylation is a continuous trait in colorectal cancer and that CIMP does not exist as a distinct feature[3].

Since CIMP+ tumors form a distinct subgroup of colorectal tumors, it will be important to accurately identify these tumors without having to perform cluster analysis, so that the etiology and clinical correlates of CIMP can be investigated. In order to select the best markers that could be used to identify CIMP+ tumors, applicants used the cluster routines described above to classify tumors as either CIMP+ or CIMP−. Applicants then applied four different selection algorithms to these classifications to find the markers that best identify CIMP for each algorithm (see Methods above "CIMP Marker Selection"). This resulted in nine top CIMP− predicting markers, which were selected for further study. Applicants also retained the five best additional Type-C markers as a precaution, since the CIMP marker selection described above was driven by a relatively small number of CIMP+ tumors.

To select the best possible five-marker panel from these 14 markers, applicants evaluated all 2,002 possible five-marker panels by determining each panel's bimodality, which is an intrinsic trait of each panel and does not rely on prior CIMP definitions (see Methods above; "New CIMP Classification Panel"). Applicants also considered the MethyLight™ reaction performance characteristics of each individual marker (see Methods above; "New CIMP Classification Panel"), since the robustness of the assay can significantly impact successful implementation in studies using challenging paraffin-embedded, formalin-fixed tissues. The five-marker panel that best satisfied the reaction performance criteria, and retained a high ranking (86$^{th}$ percentile) for bimodality among the 2,002 possible five-marker panels, consisted of CACNA1G, IGF2 (a non-imprinted island at this locus), NEUROG1, RUNX3, and SOCS1 (TABLE 2 (supplemental table 2) above).

Figure 3:
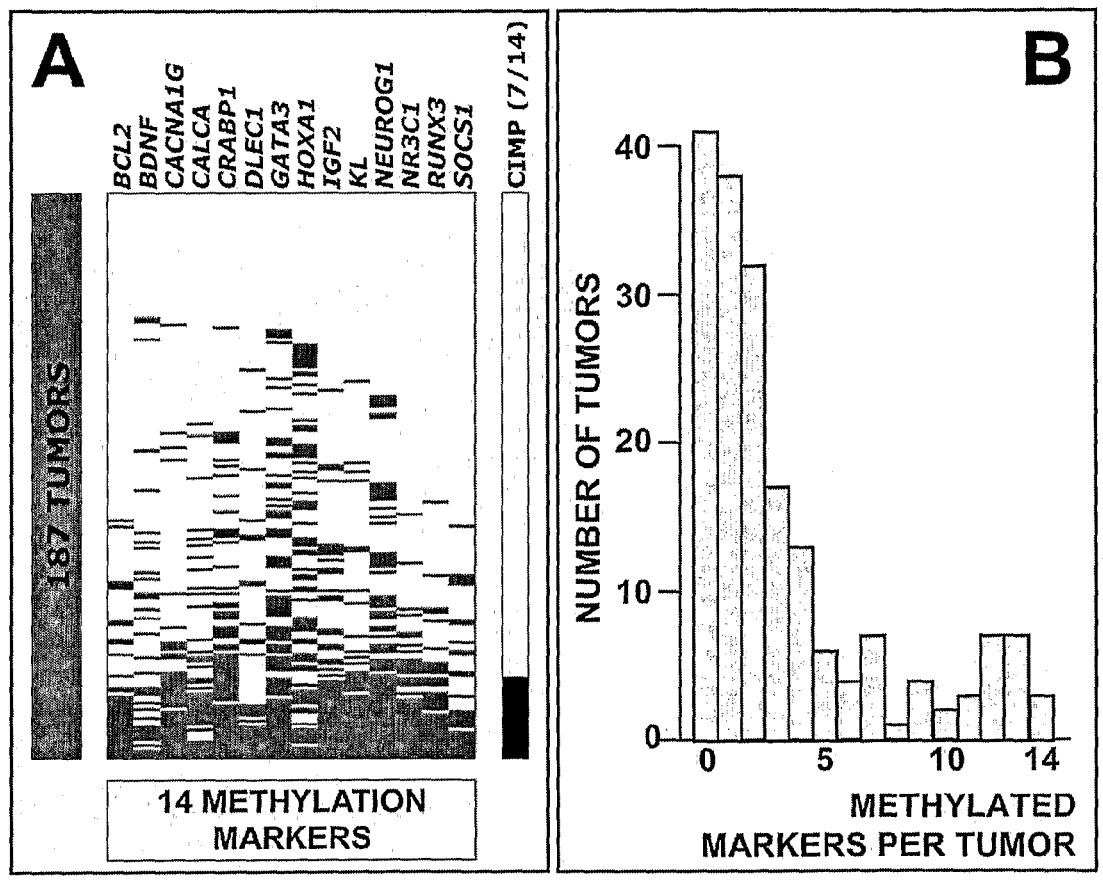
FIG. 3 shows independent testing of 14 methylation markers. The best nine CIMP markers and best five Type C markers were selected based on the data in FIG. 2 as described in Methods (Example 1) and tested on an independent set of consecutive 187 colorectal tumors. Panel A: Dichotomous heatmap of the DNA methylation data, with tumors with increasing frequency of DNA methylation sorted to the bottom. Methylation markers are arranged alphabetically. Red bars indicate PMR≧10, whereas very light blue bars indicate PMR<10. The optimal threshold for CIMP+ based on minimizing the within group sum of squared errors was 7 or more methylated markers out of 14. CIMP status defined as such is indicated for each tumor in black (CIMP+) or gray (CIMP−) to the right of the heatmap. Panel B: Histogram showing the distribution of the numbers of tumors with different numbers of methylated markers.
Figure 4:
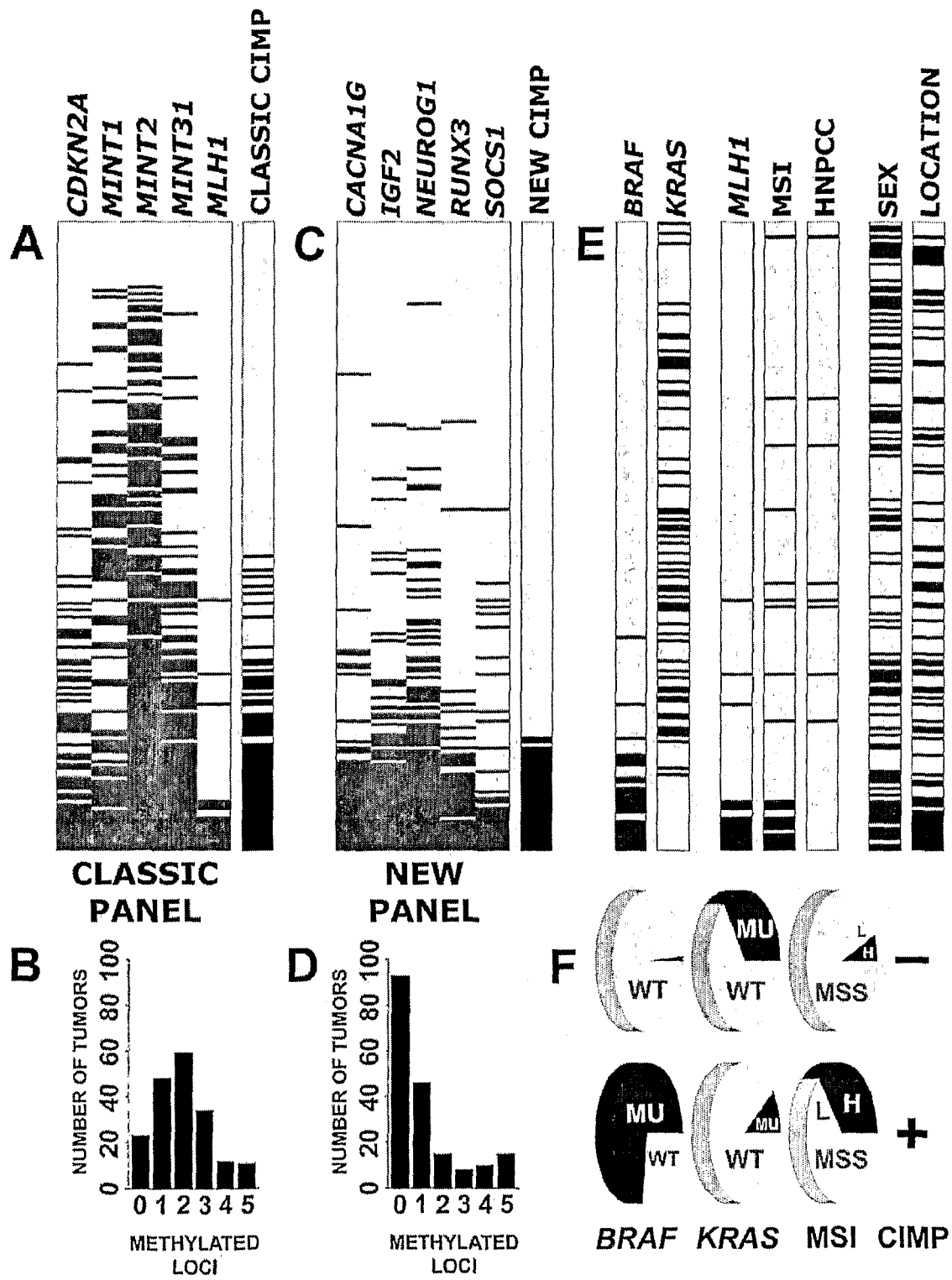
FIG. 4 shows comparison of CIMP panel performance. The 187 tumors shown in FIG. 3 were screened against two sets of CIMP markers as described in the Methods (Example 1). The data are represented as in FIG. 3A. The alignment of each tumor is maintained across panels A, C, and E. Panel A: Dichotomous heatmap representing DNA Methylation data using a classic set of CIMP markers. Panel B: Histogram of the methylation frequency distribution for the set of classic CIMP markers. Panel C: Dichotomous heatmap representing DNA Methylation data using a newly developed set of CIMP markers. Panel D: Histogram of the methylation frequency distribution for the new set of CIMP markers. For both marker panels, a tumor was considered CIMP+ if at least 3 of 5 markers were methylated. CIMP status determined by each panel is indicated to the right of each panel heatmap, with light gray indicating CIMP− and black indicating CIMP+. Panel E: Covariate status of each tumor is shown on the right, with the presence of BRAF and KRAS mutations indicated with blue bars and wild-type alleles indicated in green. Microsatellite instability (MSI) status is indicated as MSI-high (MSI-H) (blue bars), MSI-low (MSI-L) (very light blue bars), and microsatellite stable (MSS) (green bars). Cases consistent with Hereditary Non-Polyposis Colorectal Cancer (HNPCC) are indicated by blue bars. Female and proximal colonic location cases are indicated with blue bars, while male and distal colonic location cases are indicated with green bars. Panel F: Pie charts illustrating the relative frequencies of BRAF and KRAS mutations and MSI status categories for CIMP− (Top) and CIMP+ (Bottom) tumors are shown on the lower right, with color codings as described above.

Applicants used three methods to compare this new candidate diagnostic panel to a classic CIMP panel consisting of five traditional CIMP markers (CDKN2A (p16), MINT1, MINT2, MINT31, and MLH1) (FIG. 4). First, applicants determined that 99% of the 2,002 five-marker panel combinations described above showed a better bimodal distribution than the classic CIMP panel, whereas our new panel was among the top 14% of panels. Second, applicants compared the cross-panel classification error rates among various panels compiled from the 14 markers analyzed in FIG. 3 plus the five traditional CIMP markers that comprise the classic panel shown in FIG. 4 (TABLE 3 (supplemental table 3) below).

TABLE 3

(supplemental table 3).

| | Panel-19 | Panel-14 (w/o Classic) | Panel-14 (w/o New) | Panel-9 | Classic | New |
|---|---|---|---|---|---|---|
| Panel-19 (19 CIMP Genes) | 0 | 1.1 | 2.1 | 3.7 | 13.4 | 2.7 |
| Panel-14 (w/o Classic) | 1.1 | 0 | 2.1 | 3.7 | 14.4 | 2.7 |
| Panel-14 (w/o New) | 2.1 | 2.1 | 0 | 2.7 | 13.4 | 4.8 |
| Panel-9 (w/o New & w/o Classic) | 3.7 | 3.7 | 2.7 | 0 | 16.0 | 6.4 |
| Classic Panel | 13.4 | 14.4 | 13.4 | 16.0 | 0 | 15.0 |
| New Panel | 2.7 | 2.7 | 4.8 | 6.4 | 15.0 | 0 |

Cross-panel classification error rates among various CIMP classification panels, expressed as percentages. For each panel, the threshold distinguishing CIMP+ from CIMP− samples was chosen by minimizing the within group sum of squared errors. For the panels of 5 markers, samples containing at least 3 methylated markers were considered CIMP+, 4 methylated markers for panels of 9, 7 methylated markers for panels of 14, and 9 methylated markers for the panel of 19. If all panels are capturing the same information, then one would expect to find relatively low cross-panel classification error rates. The new panel of five markers outperforms the panel of classic CIMP loci in every comparison. It even gives lower classification error than the classic panel against a panel of 14 markers that includes the classic panel, but excludes the new panel. This suggests that the new panel captures the group concordance better than the classic panel.

Example 4

Assembly and Evaluation of CIMP Panels

To obtain further insight into the relative performance of these 14 markers in the classification of CIMP+ tumors, applicants analyzed a third independent set of 187 tumors using these markers, and observed a strongly bimodal distribution of tumors by number of methylated markers (FIG. 3).

The new panel of five markers outperformed the panel of classic CIMP loci in every comparison. The third strategy that applicants used to evaluate the performance of panels was to compare their associations with characteristics of colorectal cancer that have previously been reported to be associated with CIMP+ status. It is assumed that if this association reflects an important underlying biological relationship, then a superior CIMP classification would result in a stronger association. The relationships between the methylation behavior of the two panels and BRAF mutation, KRAS mutation, MSI status, HNPCC status, sex, and proximal colonic location are represented graphically in FIG. 4, while the statistical analyses using the new CIMP panel classification are summarized in TABLE 4.

TABLE 4

Distribution of covariates by New CIMP Panel.

| VARIABLE | | OVERALL | | CIMP+ (3-5 loci) | | CIMP− (0-2 loci) | | P-value |
|---|---|---|---|---|---|---|---|---|
| | | N | % | N | % | N | % | |
| TOTAL | | 187 | 100% | 33 | 18% | 154 | 82% | |
| SEX | Male | 103 | 55% | 13 | 39% | 90 | 58% | |
| | Female | 84 | 45% | 20 | 61% | 64 | 42% | 0.05 |
| SUBSITE | Proximal | 57 | 33% | 19 | 59% | 38 | 27% | |
| | Distal | 118 | 67% | 13 | 41% | 105 | 73% | 0.0005 |
| | No Info | 12 | | | | | | |
| MSI | MSI-high | 21 | 11% | 12 | 36% | 9 | 6% | |
| STATUS | MSI-low | 19 | 10% | 4 | 12% | 15 | 10% | |
| | MSS | 147 | 79% | 17 | 52% | 130 | 84% | $3.1^{-5}$ |
| HNPCC | Yes | 8 | 4% | 0 | 0% | 8 | 5% | |
| STATUS | No | 179 | 96% | 33 | 100% | 146 | 95% | 0.35 |
| MLH1 | Yes | 16 | 9% | 13 | 39% | 3 | 2% | |
| METHYLATION | No | 171 | 91% | 20 | 61% | 151 | 98% | $2.6^{-9}$ |
| BRAF | Mutant | 26 | 14% | 24 | 73% | 2 | 1% | |
| MUTATION | WT | 161 | 86% | 9 | 27% | 152 | 99% | $1.6^{-21}$ |
| KRAS | Mutant | 55 | 31% | 3 | 10% | 52 | 35% | |
| MUTATION | WT | 123 | 69% | 28 | 90% | 95 | 65% | .002 |
| | No Info | 9 | | | | | | |
| MEAN AGE (SD)* | | 65.5 (12.9) | | 68.6 (12.7) | | 64.8 (12.9) | | 0.13 |

P-values are for likelihood ratio tests from logistic regression with CIMP status as the outcome. For the variable HNPCC we report the p-value from Fisher's exact test.
*Four CIMP− subjects are missing age.

Of particular note is the extremely strong relationship between CIMP and BRAF mutation ($P=1.6\times10^{-21}$). The Odds Ratio for this association is 203 (95% CI 41, 995), a far stronger association of CIMP and BRAF mutation than any reported so far in the literature[5,9], and is a further indication of the classification accuracy of applicants' new five-marker panel.

Applicants' tight definition of CIMP appears to exclude tumors with KRAS mutation, which has been reported by others to be associated with CIMP[5,10]. To investigate this further, applicants determined the KRAS mutation status of the tumors clustered in FIG. 2. KRAS mutant tumors are distributed across the dendrogram, but show some minor clusters, which appear to be less homogeneous with respect to their methylation profile than the major CIMP cluster (FIG. 2). Interestingly, in this analysis, all of the CIMP+ tumors, with one exception, have either a BRAF or KRAS mutation.

To further investigate the association between KRAS or BRAF mutation status and methylation behavior, applicants investigated the individual associations of the 14 markers shown in FIG. 3, plus the five classic CIMP markers TABLE 4 (supplemental table 4).

All 19 markers were significantly associated with BRAF mutation. Three markers (CDKN2A, CRABP1 and NEUROG1) were positively associated with KRAS mutation after exclusion of BRAF mutant tumors, indicating that a separate KRAS-associated CIMP subgrouping exists with an overlapping set of methylation markers. The biological significance of the very tight association between the major CIMP and BRAF mutation is not clear, but it is interesting to note that transformation of fibroblasts by fos or ras oncogenes involves upregulation of DNA methyltransferase DNMT1 expression and increased global DNA methylation[11,12].

Applicants find that microsatellite instability (MSI-H), with the exception of one tumor, is fully explained by either a confirmed HNPCC association or CIMP+ associated MLH1 methylation (FIG. 4). Since MLH1 methylation-associated microsatellite instability generally does not occur among sporadic cases outside the context of CIMP, it appears that the underlying basis for mismatch repair deficiency in sporadic colorectal cancer is a broader epigenetic control defect that affects MLH1 in some but not all CIMP tumors. Therefore, an accurate classification of CIMP+ tumors will be essential to understanding the etiology of sporadic MSI-H colorectal tumors. CIMP and BRAF mutation are highly associated with the serrated pathway of colorectal cancer development[9], and therefore an epigenetic regulatory defect may be implicated in the genesis of serrated neoplasia. Dissecting the separate clinical and etiological features associated with mismatch repair deficiency, CIMP, proximal tumor location, and BRAF mutation status will further elucidate this mechanism.

Figure 5:
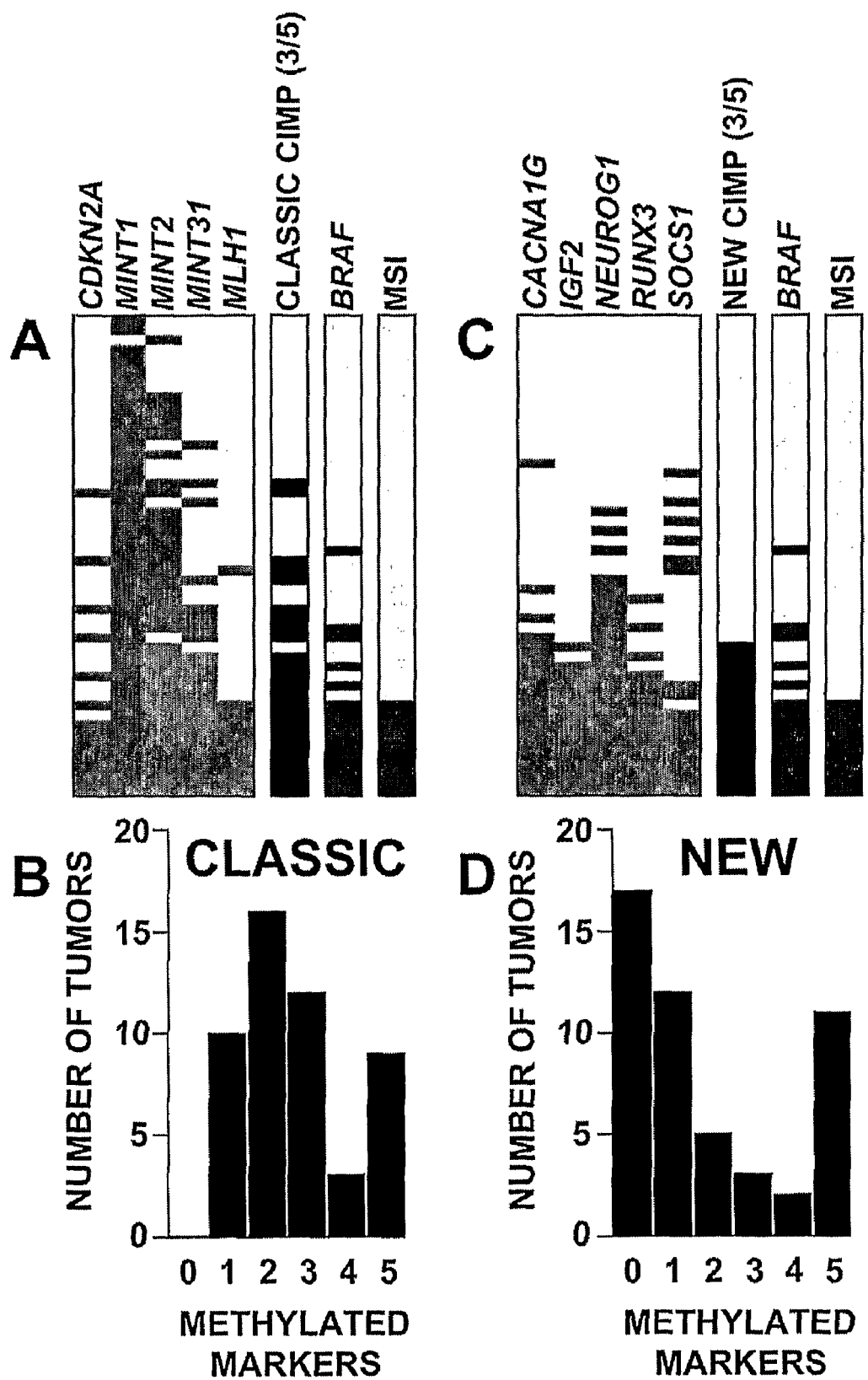
FIG. 5 shows a final independent test of CIMP panels. The classic and new CIMP panels were screened against 50 colorectal tumors obtained from the Mayo Clinic and Foundation, Rochester, Minn. These tumors were selected to include 40 MSS cases and 10 MSI-H, non-HNPCC cases to most efficiently compare the associations of the two panels on a modest number of tumors. Panel A: Dichotomous heatmap representing DNA Methylation data using a classic set of CIMP markers. Panel B: Histogram of the methylation frequency distribution for the set of classic CIMP markers. Panel C: Dichotomous heatmap representing DNA Methylation data using a newly developed set of CIMP markers. Panel D: Histogram of the methylation frequency distribution for the new set of CIMP markers. For both marker panels, a tumor was considered CIMP+ if at least 3 of 5 markers were methylated. CIMP status determined by each panel, BRAF mutation status, and MSI status is indicated to the right of each panel heatmap, with black indicating CIMP+, BRAF mutant, and MSI-H status and light gray marking CIMP−, BRAF wildtype, and MSS status.

Since the panel of tumors shown in FIGS. 3 and 4 contributed to the development of applicants' new CIMP diagnostic panel, we evaluated the new CIMP panel and the classic panel on a fourth set of independent tumors (FIG. 5). This analysis confirmed that the new panel outperforms the classic panel and easily recognizes a distinct, heavily methylated subset of colorectal tumors that encompasses almost all BRAF mutant, and sporadic MSI-H colorectal tumors.

In summary, applicants have provided definitive evidence for the existence of CIMP as a distinct trait among colorectal adenocarcinomas. Additionally, applicants have developed an improved method for the classification of CIMP (See TABLE 5 for representative preferred markers). Furthermore, applicants have found that CIMP underlies almost all cases of sporadic MSI-H colorectal cancer and tumors with mutation of the BRAF oncogene.

TABLE 4

(supplemental table 4). Methylation frequency by KRAS and BRAF status.

| Reaction | Overall (N = 187) N | % | KRAS−/ BRAF− (N = 98) N | % | KRAS+/ BRAF− (N = 55) N | % | Fisher's exact test p* | KRAS−/ BRAF+ (N = 25) N | % | Fisher's exact test p$ | Heterogeneity test p# |
|---|---|---|---|---|---|---|---|---|---|---|---|
| BCL2.M1B..HB.140. | 34 | 18% | 11 | 11% | 3 | 5% | 0.381 | 18 | 72% | 4.5E-09 | 5.6E-11 |
| BDNF.M2B..HB.258. | 32 | 17% | 11 | 11% | 7 | 13% | 0.798 | 13 | 52% | 3.1E-05 | 4.4E-05 |
| CACNA1G.M1B..HB.158. | 39 | 21% | 11 | 11% | 5 | 9% | 0.788 | 20 | 80% | 5.2E-11 | 3.2E-12 |
| CALCA.M1B..HB.166. | 37 | 20% | 10 | 10% | 9 | 16% | 0.311 | 16 | 64% | 9.7E-08 | 1.9E-07 |
| CRABP1.M1B..HB.197. | 62 | 33% | 15 | 15% | 21 | 38% | 0.003 | 23 | 92% | 6.7E-13 | 1.1E-12 |
| IGF2.M2B..HB.319. | 48 | 26% | 14 | 14% | 10 | 18% | 0.644 | 22 | 88% | 4.9E-12 | 3.7E-12 |
| KLM1B..HB.175. | 40 | 21% | 11 | 11% | 5 | 9% | 0.788 | 21 | 84% | 4.2E-12 | 2.5E-13 |
| NR3C1.M1B..HB.067. | 37 | 20% | 5 | 5% | 6 | 11% | 0.204 | 25 | 100% | 1.7E-21 | 7.8E-23 |
| RUNX3.M1B..HB.181. | 34 | 18% | 3 | 3% | 4 | 7% | 0.252 | 24 | 96% | 3.4E-21 | 5.7E-23 |
| GATA3.M1B..HB.327. | 74 | 40% | 26 | 27% | 22 | 40% | 0.103 | 25 | 100% | 3.0E-12 | 9.1E-12 |
| HOXA1.M2B..HB.268. | 69 | 37% | 36 | 37% | 15 | 27% | 0.285 | 15 | 60% | 4.2E-02 | 2.2E-02 |
| NEUROG1.M1B..HB.261. | 66 | 35% | 17 | 17% | 22 | 40% | 0.003 | 24 | 96% | 1.5E-13 | 3.6E-13 |
| SOCS1.M1B..HB.042. | 28 | 15% | 11 | 11% | 2 | 4% | 0.137 | 13 | 52% | 3.1E-05 | 8.0E-07 |
| DLEC1.M1B..HB.225. | 28 | 15% | 9 | 9% | 3 | 5% | 0.539 | 14 | 56% | 1.5E-06 | 1.9E-07 |
| MINT31.M1B..HB.162. | 82 | 44% | 29 | 30% | 24 | 44% | 0.111 | 25 | 100% | 2.0E-11 | 6.7E-11 |
| MINT1.M1B..HB.161. | 77 | 41% | 41 | 42% | 15 | 27% | 0.082 | 17 | 68% | 2.5E-02 | 2.9E-03 |
| MINT2.M1B..HB.187. | 141 | 75% | 68 | 69% | 43 | 78% | 0.264 | 24 | 96% | 4.4E-03 | 1.1E-02 |
| CDKN2A.M2B..HB.081. | 55 | 29% | 13 | 13% | 20 | 36% | 0.002 | 20 | 80% | 3.1E-10 | 4.4E-10 |
| MLH1.M2B..HB.150. | 16 | 9% | 3 | 3% | 0 | 0% | 0.553 | 12 | 48% | 1.2E-07 | 7.3E-10 |

*comparing proportion KRAS+/BRAF− to KRAS−/BRAF−
$comparing proportion KRAS−/BRAF+ to KRAS−/BRAF−
using Fisher's exact test

TABLE 5

Representative preferred markers.

| HUGO RXNNAME | RXN ID | PURPOSE | FORWARD PRIMER | REVERSE PRIMER | PROBE |
|---|---|---|---|---|---|
| 1 CACNA1G | HB-158 | CIMP Marker | TTTTTTCGTTTCGCGTTTAGGT | CTCGAAACGACTTCGCCG | 6FAM-AAATAACGCCGAATCCGACAACCGA-BHQ |
| 2 IGF2 | HB-319 | CIMP Marker | GAGCGGTTTCGGTGTCGTTA | CCAACTCGATTTAAACCGACG | 6FAM-CCCTCTACCGTCGCGAACCCGA-BHQ |
| 3 NEUROG1 | HB-261 | CIMP Marker | CGTGTAGCGTTCGGGTATTTGTA | CGATAATTACGAACACACTCCGAAT | 6FAM-CGATAACGACCTCCCGCGAACATAAA-BHQ-1 |
| 4 RUNX3 | HB-181 | CIMP Marker | CGTTCGATGGTGGACGTGT | GACGAACAACGTCTTATTACAACGC | 6FAM-CGCACGAACTCGCCTACGTAATCCG-BHQ-1 |
| 5 SOCS1 | HB-042 | CIMP Marker | GCGTCGAGTTCGTGGGTATTT | CCGAAACCATCTTCACGCTAA | 6FAM-ACAATTCCGCTAACGACTATCGCGCA-BHQ-1 |
| 6 ALU | HB-313 | Normalization Control | GGTTAGGTATAGTGGTTTATATTTGTAATTTTAGTA | ATTAACTAAACTAATCTTAAACTCCTAACCTCA | 6FAM-CCTACCTTAACCTCCC-MGBNFQ |
| 7 COL2A1 | HB-057 | Normalization Control | TCTAACAATTATAAACTCCAACCACCAA | GGGAAGATGGGATAGAAGGGAATAT | 6FAM-CCTTCATTCTAACCCAATACCTATCCCACCTCTAAA-BHQ-1 |
| 8 COL2A1 | HD-005 | Bisulfite Conversion Control | GAAGATGGGATAGAAGGGAATACATCT | CTCCAACCACCAAACCTTCATT | 6FAM-GGCCCAATGCCTGTCCCACCT-BHQ-1 |

Example 5

Use of the Colon Cooperative Family Registry (CFR) for a Population-Based Study of CIMP Further aspects of the present invention provide a foundation for a population-based study of CIMP, by providing a novel panel of very carefully selected methylation markers representing the CIMP subgroup, and having utility to classify CIMP.

Specifically, as described herein above, particular aspects of the present invention provide novel methods and compositions for determining the relationship between CIMP status and other molecular features of the cancers including, but not limited to BRAF mutation, KRAS mutation and MSI status.

Additional aspects provide novel methods and compositions for determining the relationship between CIMP status and other variables including, but not limited to age, sex, tumor location, family history, race, country of origin, tumor characteristics (including, tumor type, tumor grade, invasive margin characteristics, lymphocyte infiltration characteristics, direct spread, lymph node spread, venous spread and type of residual adjacent polyp, if present).

Yet additional aspects provide novel methods and compositions for determining, between subgroups defined by CIMP status and BRAF mutations, effects of selected risk factors including, but not limited to body mass index, smoking history, alcohol intake, dietary folate intake, folate metabolic enzyme polymorphisms and history of hormonal use.

Overview of the Colon Cooperative Family Registry (CFR)

The Cooperative Family Registry for Colorectal Cancer Studies, referred to herein (and as known in the art) as the "Colon CFR", is an NCI-supported consortium initiated in 1997 through a competitive RFA. This consortium is dedicated to the establishment of a comprehensive collaborative infrastructure for interdisciplinary studies in the genetics and genetic epidemiology of colorectal cancer. The cooperating institutions are collecting epidemiological information and laboratory specimens from families who represent the continuum of risk for CRC. Families are recruited through the participating Registry sites, and as of July, 2002, the CFR registry included data and biospecimens from approximately 7,773 probands plus selected close relatives, both affected and unaffected, and, in some centers, additional unrelated controls.

The CFR is an international consortium of six research institutions and an Informatics Center. The participating centers are at the: Fred Hutchinson Cancer Research Center, Seattle, Wash. (P.I.: John Potter); Mayo Clinic, Rochester, Minn. (P.I.: Noralane Lindor); University of Southern California, Los Angeles (P.I.: Robert Haile); University of Queensland, Brisbane, Australia (P.I.: John Hopper); Cancer Care Ontario, Ontario, Canada (P.I.: Steve Gallinger); and the University of Hawaii Cancer Research Center, Honolulu, Hi. (P.I.: Loïc Le Marchand). The Informatics Center (IC) is located at the University of California, Irvine (P.I.: Hoda Anton Culver).

The six Registry centers use standardized instruments and protocols to collect family history information, epidemiological and clinical data, screening behavior, and related biological specimens (blood samples and tumor blocks), with a strong emphasis on quality control (QC) a and privacy measures throughout the collection, processing, and storage of data and samples (see below for key components). The CFR investigators have substantially enriched the resource beyond the scope of the original RFA by obtaining two collaborative supplements, one to characterize colorectal tumors for microsatellite instability (MSI), and the other to establish lymphoblastoid cell lines for particularly informative registry participants.

The Colon CFR also developed a relevant core questionnaire that is administered to all CFR participants, including cases, controls, and affected and unaffected relatives. This standardized instrument contains core questions asked by all centers, covering established and suspected risk factors for colorectal cancer, including medical history and medication use, reproductive history (for female participants), family history, physical activity, demographics, alcohol and tobacco use, and limited dietary factors. Centers are allowed to customize questions for local usage, in particular for different language usage and brand names, and to add additional questions of interest. The method of administration of the questionnaire is allowed to vary by center and has been administered by face-to-face interview, over the telephone using a Computer-Assisted Telephone Interview (CATI), or by mail for self-administration. Detailed question-by-question manuals for administration were developed for further standardization.

In addition to the risk factor questionnaire, which includes a section on consumption of selected food items, all centers except FHCRC and Mayo also administered a detailed food frequency questionnaire. Australia used a version developed specifically for Australia. The other centers used a well validated food frequency questionnaire (FFQ) developed at the Cancer Research Center of Hawaii (CRCH) (Stram, 2000). Expertise in dietary assessment has been a strength of the Hawaii group for many years. The CRCH's Nutrition Support Shared Resource consists of faculty nutritionists, dietitians and computer programmers and includes an extensive food composition database to accommodate the diets of several US ethnic groups. This database contains more than 3,200 food items and more than 100 components (nutrients and non-nutrients) and is continuously updated with information from standard sources (such as the USDA), other sources (such as international organizations), local recipes, and special food analyses. This resource was used to develop a food composition table for the CFR FFQ which is the same as the one used in the Multiethnic Cohort Study.

The different sites of the CFR are collaborating on creating a virtual data-analysis group to take advantage of the expertise across the collaborating centers and to avoid duplication of effort. The group will develop data-analysis strategies that are suitable for the Colon CFR study population, will divide development and analytic tasks according to specific expertise, will oversee analysis for Colon CFR studies, and will contribute to the final interpretation and write-up of findings. The data analysis group includes Drs. Duncan Thomas (USC consortium), Kim Siegmund (USC consortium, and co-Investigator on this application), John Hopper (Australasian CFR), and Li Hsu (FHCRC). Drs. Hopper and Thomas serve as co-directors of this unit. They report on their activities to the Epidemiology and Analysis Working Group.

The University of Melbourne Consortium (J. Hopper, Ph.D., P. I.) recruits clinic-based families from family cancer clinics and population-based families from cancer registries and electoral rolls. During Phase I (1997-2002) 250 clinic-based families were recruited in Brisbane, Melbourne, Adelaide, Sydney, and Perth, Australia, and in Auckland, New Zealand. Clinic-based families included those with HNPCC or HNPCC-like family histories. In addition, 627 population-based CRC cases selected from the Victorian Cancer Registry in Melbourne, aged between 18 and 59 years at diagnosis, and their first- and second-degree relatives have been recruited. Also, 260 non-cancer population-based controls selected through the electoral roll and their first- and second-degree relatives have been recruited. Epidemiology/family history questionnaires were completed on all respondents by either in-person or telephone interview. Tumor blocks and blood samples have been collected on approximately 800 cases. Blood samples were collected from approximately 3,800 cases, controls and their relatives. There were 1,351 population-based probands selected and eligible. Of these, 141 were deceased and the physician refused permission to contact 85, leaving 1,125 (83%) that they were allowed to contact. Of these, they were unable to contact 174, leaving 951 probands who were selected and eligible. Of these 951, 324 (34%) refused and the remaining 627 (66%) joined the CFR. There were 1545 siblings of these 627 probands. They had permission to contact 840. Only 2 of these 840 refused to participate. Of the 705 siblings whom they had no permission to contact, they have proxy questionnaires completed by a participating relative for 675.

University of Hawaii Cancer Research Center (P.I.: Loïc Le Marchand, U01 CA74806): The Hawaii CFR site has focused on recruiting multi-case CRC families in the multiethnic population of Hawaii. This approach was originally selected in order to increase the study's efficiency by enriching the sample for genetic risk factors. All new incident CRC cases diagnosed in the state of Hawaii in 1997-2001 (n=1, 800) were screened through personal interview for family history. Those with a positive history of CRC among first-degree relatives were invited to participate in the CFR, along with their first-degree relatives. In addition, 60 multi-case families identified in a recently completed population-based, case-control family study of CRC were invited to participate in the Registry. These families were prospectively ascertained through contact with all CRC incident cases under age 60 years diagnosed between 1987 and 1996 among Japanese, Caucasian, Hawaiian and Chinese residents of Oahu (where 85% of the population of the state reside). Pedigrees have been expanded to include second-degree relatives for some large multiplex families. Epidemiology and family history questionnaires were obtained from 950 participants. In addition, 155 tumor blocks and 767 blood samples were collected. For probands, there were 2,245 selected and eligible cases. Of these, they received permission to contact 1,988 (89%). Of these 1988, they were unable to contact 41, leaving 1,947 cases. Of these 1,947 cases, 140 refused, 57 were deceased, and they lost contact with 54, so 1,696 (87%) completed a family history screening questionnaire. Of these 1,696, 1,397 were not eligible for the CFR by virtue of their family history and 51 were not selected for further recruitment, leaving 248 eligible and selected for recruitment. Of these 248, 64 refused, 8 were deceased, and they lost contact with 1, leaving 175 (70%) who participated in the CFR. The total number of siblings was 879, of whom 852 were eligible. Of these siblings, 439 (52%) participated.

The Fred Hutchinson Cancer Research Center (J. Potter, M. D., Ph.D., P. I.) identifies colorectal cancer (CRC) cases through the population-based Puget Sound SEER (NCI) Program. During Phase I (1997-2002), all incident CRC cases diagnosed between the ages of 20 and 74 in three Washington state counties and their first-degree relatives were ascertained. Age and gender-matched population-based controls were ascertained from two population lists-controls under age 65 years were recruited through driver's license lists; controls 65-74 years were selected from Health Care Finance Administration (HCFA, currently CMS) files.

Epidemiology/family history questionnaires were completed on all respondents over the telephone using a computer-assisted telephone interview (CATI) format. Tumor blocks were collected on all cases and CRC-affected family members (diagnosed less than 5 years prior to recruitment). Blood samples were collected from all cases, all family members in high-risk families, a sample of family members in non-high-risk families, and a sample of controls. During Phase I, 1,831 cases, 4,325 family members, and 1,531 population-based controls were enrolled. In addition, 1,570 tumor blocks and 2,713 blood samples were collected. For probands, initially there were 2,959 eligible. Of these, they received permission to contact 2, 733 (92%) Of these 2,733, they were unable to contact 22 and 364 were determined to be ineligible, leaving 2,347 selected and eligible. Of these 2,347, 267 refused, 185 were deceased, and they lost contact with 64, so 1,831 (78%) participated in the CFR. There were 2,225 siblings who were eligible and selected. Of these 2,225, 173 refused, 7 were deceased, and they lost contact with 66, so 1,979 siblings (89%) participated in the CFR.

The Mayo Clinic (N. M. Lindor, M.D., Principal Investigator) recruited 479 probands from high or intermediate risk families from the population-based Minnesota Cancer Surveillance System (MCSS), selected from 4,471 incident cases diagnosed over a four-year period from 1997 through 2000. Cases were surveyed for family history and high/intermediate risk families were defined as those with two or more cases of CRC, those with known familial adenomatous polyposis (FAP), those in which the proband was diagnosed under the age of 50 years, and families reporting an hereditary non-polyposis colon cancer-like (HNPCC-like) tumor spectrum. In addition, a random sampling of respondents from the MCSS was conducted until 215 randomly selected participants were identified and recruited. An additional 245 high- or intermediate-risk families were also accrued from two non-population-based sources: other Mayo Clinic Rochester patients and the North Central Cancer Treatment Group. Recruitment of high-risk families was extended to parents, affected and unaffected siblings (up to four, aiming for same sex, oldest sibs); if a parent was affected, aunts and uncles on that side of the family were also invited to enroll. Overall, 2,469 relatives of CRC probands were enrolled (provided informed consent, blood specimens, medical record access, and completed the epidemiology risk factor questionnaire). Unaffected relatives of probands can serve as controls. Spouses of individuals with cancer were also recruited as another type of control. Tumor blocks from 633 CRC participants (probands and affected relatives) and 161 non-CRC were collected and tested for microsatellite instability and immunohistochemistry for the main DNA mismatch repair gene proteins. For the population-based probands, there were initially 5,002 potentially eligible cases. Of these, the physician refused contact for 115 and 428 were deceased, so they had permission to contact 4,459. Of these 4,459,748 refused, 83 were deceased, and they lost contact with 1,776, so 1,852 (42%) completed the screening questionnaire. Of these 1,852 cases, 8 were deemed ineligible and 1,308 were not selected for further recruitment, leaving 536 selected and eligible. Of these 536 cases, 52 refused and 2 were deceased, so 482 (90%) participated in the CFR. They invited 844 siblings to participate in the CFR. Of these 844, 572 (68%) agreed to participate.

Cancer Care Ontario (S. Gallinger, M.D., P. I.): The Cancer Care Ontario site is a consortium that includes eight Regional Cancer Centers covering the entire province of Ontario. During Phase I, 8,818 incident CRC cases, diagnosed between 1997-2000, were identified from the population-based Ontario Cancer Registry. Family histories were obtained on 3,780 cases and stratified by risk (high-meets Amsterdam criteria for HNPCC; intermediate=HNPCC-like and/or other specific features such as young age, multiple polyps; low=none of the above). Recruitment (at least one core element) was successful for 70 high-risk families, 845 intermediate-risk families and 430 low-risk families (which is a 25% random sample of this larger latter group). In addition, 2,679 first- and second-degree relatives of registered probands were recruited, and 890 non-cancer, age and gender-matched population controls using residential telephone lists and 1,021 population controls using the Ontario ministry of finance property assessment file for year 2000 were also recruited. Blood samples have been obtained for 1,052 probands, 2,080 relatives, 1,289 controls, and 1,372 tumors (mostly CRC specimens from probands) have been processed. For probands, there were 8,726 eligible cases. Of these, they received permission to contact 7,229 (83%). Of these 7,229, 24 were deemed ineligible and they were unable to contact 164, leaving 7,041 who were eligible and selected. Of these 7,041 cases, 2,960 refused and 301 were deceased, leaving 3,780 (54%) who completed the screening questionnaire. Of these 3,780 cases, 1 was ineligible and 1,929 were not selected for further recruitment based on their family history, leaving 1,850 selected and eligible. Of these 1,850 cases, 217 refused, 27 were deceased, and they lost contact with 7, so 1,599 (86%) participated in the CFR. They invited 1565 siblings to join the CFR and 837 (53.5%) of these siblings participated.

The University of Southern California Consortium (R. Haile, Dr PH., P. I.) includes the Universities of Southern California, North Carolina, Colorado, Arizona, and Minnesota, Dartmouth Medical School, and the Cleveland Clinic. From the population based cancer registries of all but the last of these sub-centers, this group contacted 33% of CRC cases diagnosed in Whites over a one and a half-year period. In addition, sixty-six percent of CRC cases in African-American, Asian, and Hispanic families plus all CRC cases diagnosed under age 50 years over the preceding three years were contacted. These cases were screened for a family history of CRC. Sixteen percent of single-case families and all multiple-case families were invited to participate in the CFR. A total of 633 families from these population-based sources were recruited into the Registry. The majority (about 60%) are from multiple-case families and a substantial proportion are from racial minorities. These are supplemented by 120 HNPCC (Amsterdam criteria positive), or HNPCC-like families from the Cleveland Clinic. USC serves as the coordinating center and Dartmouth the data center for this consortium. Unaffected relatives of probands are selected as controls. For the population-based probands, there were initially 5,684 potentially eligible cases. The physician refused permission to contact 103 cases, so they had permission to contact 5,581 (98%) of these cases. Of these 5,581, they were unable to contact 191 and 656 were deemed ineligible, leaving 4,734 eligible for a screening questionnaire. Of these 4,734,413 refused, 927 were deceased, and they lost contact with 291, so 3,103 (66%) completed the family history screening questionnaire. Of these 3,103,105 were ineligible, and 1,943 were not selected for further recruitment based on their family history, leaving 1,055 selected and eligible. Of these 1,055 cases, 325 refused, 75 were deceased, and they lost contact with 22, so 633 participated in the CFR. There were 746 siblings. Of these 746, 96 were excluded (deceased, cognitively impaired, language barrier and other reasons). Of the remaining 650, 247 refused and they lost contact with 14, so 389 (60%) siblings participated in the CFR.

Informatics Center (H. Anton-Culver, Ph.D., P.I.). The NCI has designated the University of California Irvine's Epidemiology Division as the Informatics Center to support the CFR. The Informatics Center:

The CFR Informatics Center (IC) has designed and maintained a secure, data processing, storage, and retrieval system that contains the core Cancer Family Registries data with the flexibility to integrate data generated through additional studies into the core schema structure;

The IC has provided guidelines for data standardization, established methods for data transmission, developed computerized validation checks, monitors quality of data, and prepares data for reporting;

Provides statistical and study design support for the CFR investigators and generates reports for special requests and descriptive summary statistics;

Helps facilitate CFR-wide communication, coordination, and administration;

Developed and maintains a secure web site to provide relevant information to CFR members;

Developed web-based software tools allowing CFR members to query database for family characteristics, view pedigrees, download files, and create tables and charts using data from the CFR database housed at the IC; and Developed web-based software to enter, process, and tracking investigator applications to use CFR data and includes automated notifications to management when new applications are received, as well as notifications to applicants, SC and AC members and others regarding the steps in the application process.

| 47675-189 Sequence Listing Table | |
|---|---|
| Grouping | SEQ ID NOs |
| Forward/Reverse Primers (14 Select) | 1-28 |
| Forward/Reverse Primers (other genes) | 29-67 |
| Probes (14 Select) | 68-81 |
| Probes (other genes) | 82-99 |
| Amplicons (14 Select) | 100-113 |
| CpG Islands (14 Select) | 114-127 |
| Genomic DNA (14 Select) | 128-141 |
| CpG Bisulfite Up (14 Select) | 142-169 |
| Genomic Bisulfite Up (14 Select) | 170-197 |
| CpG Bisulfite Down (14 Select) | 198-225 |
| Genomic Bisulfite Down (14 Select) | 226-253 |
| Gene Coding Sequences (14 Select) | 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334 |
| Protein Sequences (14 Select) | 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335 |

| Gene | Sequence Type | SEQ ID NO |
|---|---|---|
| BCL2 | Forward Primer | 1 |
| BCL2 | Reverse Primer | 2 |
| BDNF | Forward Primer | 3 |
| BDNF | Reverse Primer | 4 |
| CACNA1G | Forward Primer | 5 |
| CACNA1G | Reverse Primer | 6 |
| CALCA | Forward Primer | 7 |
| CALCA | Reverse Primer | 8 |
| CRABP1 | Forward Primer | 9 |
| CRABP1 | Reverse Primer | 10 |
| DLEC1 | Forward Primer | 11 |
| DLEC1 | Reverse Primer | 12 |
| GATA3 | Forward Primer | 13 |
| GATA3 | Reverse Primer | 14 |
| HOXA1 | Forward Primer | 15 |
| HOXA1 | Reverse Primer | 16 |
| IGF2 | Forward Primer | 17 |
| IGF2 | Reverse Primer | 18 |
| KL | Forward Primer | 19 |
| KL | Reverse Primer | 20 |
| NEUROG1 | Forward Primer | 21 |
| NEUROG1 | Reverse Primer | 22 |
| NR3C1 | Forward Primer | 23 |
| NR3C1 | Reverse Primer | 24 |
| RUNX3 | Forward Primer | 25 |
| RUNX3 | Reverse Primer | 26 |
| SOCS1 | Forward Primer | 27 |

-continued

| Gene | Sequence Type | SEQ ID NO |
|---|---|---|
| SOCS1 | Reverse Primer | 28 |
| CDH13 | Forward Primer | 29 |
| CDH13 | Reverse Primer | 30 |
| CDKN2A | Forward Primer | 31 |
| CDKN2A | Reverse Primer | 32 |
| GATA4 | Forward Primer | 33 |
| GATA4 | Reverse Primer | 34 |
| GDNF | Forward Primer | 35 |
| GDNF | Reverse Primer | 36 |
| ITGA4 | Forward Primer | 37 |
| ITGA4 | Reverse Primer | 38 |
| MINT1 | Forward Primer | 39 |
| MINT1 | Reverse Primer | 40 |
| MINT2 | Forward Primer | 41 |
| MINT2 | Reverse Primer | 42 |
| MINT31 | Forward Primer | 43 |
| MINT31 | Reverse Primer | 44 |
| MLH1 | Forward Primer | 45 |
| MLH1 | Reverse Primer | 46 |
| NEUROD2 | Forward Primer | 47 |
| NEUROD2 | Reverse Primer | 48 |
| OPCML | Forward Primer | 49 |
| OPCML | Reverse Primer | 50 |
| PENK | Forward Primer | 51 |
| PENK | Reverse Primer | 52 |
| SCGB3A1 | Forward Primer | 53 |
| SCGB3A1 | Reverse Primer | 54 |
| SFRP2 | Forward Primer | 55 |
| SFRP2 | Reverse Primer | 56 |
| TFAP2A | Forward Primer | 57 |
| TFAP2A | Reverse Primer | 58 |
| ALU | Forward Primer | 59 |
| ALU | Reverse Primer | 60 |
| BRAF | Primer 1 | 61 |
| BRAF | Primer 2 | 62 |
| BRAF | Primar 3 | 63 |
| COL2A1 | Forward Primer | 64 |
| COL2A1 | Reverse Primer | 65 |
| COL2A1 (2) | Forward Primer | 66 |
| COL2A1 (2) | Reverse Primer | 67 |
| BCL2 | Probe | 68 |
| BDNF | Probe | 69 |
| CACNA1G | Probe | 70 |
| CALCA | Probe | 71 |
| CRABP1 | Probe | 72 |
| DLEC1 | Probe | 73 |
| GATA3 | Probe | 74 |
| HOXA1 | Probe | 75 |
| IGF2 | Probe | 76 |
| KL | Probe | 77 |
| NEUROG1 | Probe | 78 |
| NR3C1 | Probe | 79 |
| RUNX3 | Probe | 80 |
| SOCS1 | Probe | 81 |
| CDH13 | Probe | 82 |
| CDKN2A | Probe | 83 |
| GATA4 | Probe | 84 |
| GDNF | Probe | 85 |
| ITGA4 | Probe | 86 |
| MINT1 | Probe | 87 |
| MINT2 | Probe | 88 |
| MINT3 | Probe | 89 |
| MLH1 | Probe | 90 |
| NEUROD2 | Probe | 91 |
| OPCML | Probe | 92 |
| PENK | Probe | 93 |
| SCGB3A1 | Probe | 94 |
| SFRP2 | Probe | 95 |
| TFAP2A | Probe | 96 |
| ALU | Probe | 97 |
| COL2A1 | Probe | 98 |
| COL2A1 (2) | Probe | 99 |
| BCL2 | Amplicon | 100 |
| BDNF | Amplicon | 101 |
| CACNA1G | Amplicon | 102 |
| CALCA | Amplicon | 103 |
| CRABP1 | Amplicon | 104 |
| DLEC1 | Amplicon | 105 |
| GATA3 | Amplicon | 106 |
| HOXA1 | Amplicon | 107 |
| IGF2 | Amplicon | 108 |
| KL | Amplicon | 109 |
| NEUROG1 | Amplicon | 110 |
| NR3C1 | Amplicon | 111 |
| RUNX3 | Amplicon | 112 |
| SOCS1 | Amplicon | 113 |
| BCL2 | CpG Island | 114 |
| BDNF | CpG Island | 115 |
| CACNA1G | CpG Island | 116 |
| CALCA | CpG Island | 117 |
| CRABP1 | CpG Island | 118 |
| DLEC1 | CpG Island | 119 |
| GATA3 | CpG Island | 120 |
| HOXA1 | CpG Island | 121 |
| IGF2 | CpG Island | 122 |
| KL | CpG Island | 123 |
| NEUROG1 | CpG Island | 124 |
| NR3C1 | CpG Island | 125 |
| RUNX3 | CpG Island | 126 |
| SOCS1 | CpG Island | 127 |
| BCL2 | Genomic DNA | 128 |
| BDNF | Genomic DNA | 129 |
| CACNA1G | Genomic DNA | 130 |
| CALCA | Genomic DNA | 131 |
| CRABP1 | Genomic DNA | 132 |
| DLEC1 | Genomic DNA | 133 |
| GATA3 | Genomic DNA | 134 |
| HOXA1 | Genomic DNA | 135 |
| IGF2 | Genomic DNA | 136 |
| KL | Genomic DNA | 137 |
| NEUROG1 | Genomic DNA | 138 |
| NR3C1 | Genomic DNA | 139 |
| RUNX3 | Genomic DNA | 140 |
| SOCS1 | Genomic DNA | 141 |
| BCL2 | CpG Island Bisulphite Up Sense | 142 |
| BCL2 | CpG Island Bisulphite Up Antisense | 143 |
| BDNF | CpG Island Bisulphite Up Sense | 144 |
| BDNF | CpG Island Bisulphite Up Antisense | 145 |
| CACNA1G | CpG Island Bisulphite Up Sense | 146 |
| CACNA1G | CpG Island Bisulphite Up Antisense | 147 |
| CALCA | CpG Island Bisulphite Up Sense | 148 |
| CALCA | CpG Island Bisulphite Up Antisense | 149 |
| CRABP1 | CpG Island Bisulphite Up Sense | 150 |
| CRABP1 | CpG Island Bisulphite Up Antisense | 151 |
| DLEC1 | CpG Island Bisulphite Up Sense | 152 |
| DLEC1 | CpG Island Bisulphite Up Antisense | 153 |
| GATA3 | CpG Island Bisulphite Up Sense | 154 |
| GATA3 | CpG Island Bisulphite Up Antisense | 155 |
| HOXA1 | CpG Island Bisulphite Up Sense | 156 |
| HOXA1 | CpG Island Bisulphite Up Antisense | 157 |
| IGF2 | CpG Island Bisulphite Up Sense | 158 |
| IGF2 | CpG Island Bisulphite Up Antisense | 159 |
| KL | CpG Island Bisulphite Up Sense | 160 |
| KL | CpG Island Bisulphite Up Antisense | 161 |
| NEUROG1 | CpG Island Bisulphite Up Sense | 162 |
| NEUROG1 | CpG Island Bisulphite Up Antisense | 163 |
| NR3C1 | CpG Island Bisulphite Up Sense | 164 |
| NR3C1 | CpG Island Bisulphite Up Antisense | 165 |
| RUNX3 | CpG Island Bisulphite Up Sense | 166 |
| RUNX3 | CpG Island Bisulphite Up Antisense | 167 |
| SOCS1 | CpG Island Bisulphite Up Sense | 168 |
| SOCS1 | CpG Island Bisulphite Up Antisense | 169 |
| BCL2 | Genomic Bisulphite Up Sense | 170 |
| BCL2 | Genomic Bisulphite Up Antisense | 171 |
| BDNF | Genomic Bisulphite Up Sense | 172 |
| BDNF | Genomic Bisulphite Up Antisense | 173 |
| CACNA1G | Genomic Bisulphite Up Sense | 174 |
| CACNA1G | Genomic Bisulphite Up Antisense | 175 |
| CALCA | Genomic Bisulphite Up Sense | 176 |
| CALCA | Genomic Bisulphite Up Antisense | 177 |
| CRABP1 | Genomic Bisulphite Up Sense | 178 |
| CRABP1 | Genomic Bisulphite Up Antisense | 179 |
| DLEC1 | Genomic Bisulphite Up Sense | 180 |
| DLEC1 | Genomic Bisulphite Up Antisense | 181 |
| GATA3 | Genomic Bisulphite Up Sense | 182 |
| GATA3 | Genomic Bisulphite Up Antisense | 183 |

-continued

| Gene | Sequence Type | SEQ ID NO |
|---|---|---|
| HOXA1 | Genomic Bisulphite Up Sense | 184 |
| HOXA1 | Genomic Bisulphite Up Antisense | 185 |
| IGF2 | Genomic Bisulphite Up Sense | 186 |
| IGF2 | Genomic Bisulphite Up Antisense | 187 |
| KL | Genomic Bisulphite Up Sense | 188 |
| KL | Genomic Bisulphite Up Antisense | 189 |
| NEUROG1 | Genomic Bisulphite Up Sense | 190 |
| NEUROG1 | Genomic Bisulphite Up Antisense | 191 |
| NR3C1 | Genomic Bisulphite Up Sense | 192 |
| NR3C1 | Genomic Bisulphite Up Antisense | 193 |
| RUNX3 | Genomic Bisulphite Up Sense | 194 |
| RUNX3 | Genomic Bisulphite Up Antisense | 195 |
| SOCS1 | Genomic Bisulphite Up Sense | 196 |
| SOCS1 | Genomic Bisulphite Up Antisense | 197 |
| BCL2 | CpG Island Bisulphite Down Sense | 198 |
| BCL2 | CpG Island Bisulphite Down Antisense | 199 |
| BDNF | CpG Island Bisulphite Down Sense | 200 |
| BDNF | CpG Island Bisulphite Down Antisense | 201 |
| CACNA1G | CpG Island Bisulphite Down Sense | 202 |
| CACNA1G | CpG Island Bisulphite Down Antisense | 203 |
| CALCA | CpG Island Bisulphite Down Sense | 207 |
| CALCA | CpG Island Bisulphite Down Antisense | 205 |
| CRABP1 | CpG Island Bisulphite Down Sense | 206 |
| CRABP1 | CpG Island Bisulphite Down Antisense | 207 |
| DLEC1 | CpG Island Bisulphite Down Sense | 208 |
| DLEC1 | CpG Island Bisulphite Down Antisense | 209 |
| GATA3 | CpG Island Bisulphite Down Sense | 210 |
| GATA3 | CpG Island Bisulphite Down Antisense | 211 |
| HOXA1 | CpG Island Bisulphite Down Sense | 212 |
| HOXA1 | CpG Island Bisulphite Down Antisense | 213 |
| IGF2 | CpG Island Bisulphite Down Sense | 214 |
| IGF2 | CpG Island Bisulphite Down Antisense | 215 |
| KL | CpG Island Bisulphite Down Sense | 216 |
| KL | CpG Island Bisulphite Down Antisense | 217 |
| NEUROG1 | CpG Island Bisulphite Down Sense | 218 |
| NEUROG1 | CpG Island Bisulphite Down Antisense | 219 |
| NR3C1 | CpG Island Bisulphite Down Sense | 220 |
| NR3C1 | CpG Island Bisulphite Down Antisense | 221 |
| RUNX3 | CpG Island Bisulphite Down Sense | 222 |
| RUNX3 | CpG Island Bisulphite Down Antisense | 223 |
| SOCS1 | CpG Island Bisulphite Down Sense | 224 |
| SOCS1 | CpG Island Bisulphite Down Antisense | 225 |
| BCL2 | Genomic Bisulphite Down Sense | 226 |
| BCL2 | Genomic Bisulphite Down Antisense | 227 |
| BDNF | Genomic Bisulphite Down Sense | 228 |
| BDNF | Genomic Bisulphite Down Antisense | 229 |
| CACNA1G | Genomic Bisulphite Down Sense | 230 |
| CACNA1G | Genomic Bisulphite Down Antisense | 231 |
| CALCA | Genomic Bisulphite Down Sense | 232 |
| CALCA | Genomic Bisulphite Down Antisense | 233 |
| CRABP1 | Genomic Bisulphite Down Sense | 234 |
| CRABP1 | Genomic Bisulphite Down Antisense | 235 |
| DLEC1 | Genomic Bisulphite Down Sense | 236 |
| DLEC1 | Genomic Bisulphite Down Antisense | 237 |
| GATA3 | Genomic Bisulphite Down Sense | 238 |
| GATA3 | Genomic Bisulphite Down Antisense | 239 |
| HOXA1 | Genomic Bisulphite Down Sense | 240 |
| HOXA1 | Genomic Bisulphite Down Antisense | 241 |
| IGF2 | Genomic Bisulphite Down Sense | 242 |
| IGF2 | Genomic Bisulphite Down Antisense | 243 |
| KL | Genomic Bisulphite Down Sense | 244 |
| KL | Genomic Bisulphite Down Antisense | 245 |
| NEUROG1 | Genomic Bisulphite Down Sense | 246 |
| NEUROG1 | Genomic Bisulphite Down Antisense | 247 |
| NR3C1 | Genomic Bisulphite Down Sense | 248 |
| NR3C1 | Genomic Bisulphite Down Antisense | 249 |
| RUNX3 | Genomic Bisulphite Down Sense | 250 |
| RUNX3 | Genomic Bisulphite Down Antisense | 251 |
| SOCS1 | Genomic Bisulphite Down Sense | 252 |
| SOCS1 | Genomic Bisulphite Down Antisense | 253 |
| BCL2 | Alpha isoform mRNA | 254 |
| BCL2 | Alpha isoform protein | 255 |
| BCL2 | Beta isoform mRNA | 256 |
| BCL2 | Beta isoform protein | 257 |
| BDNF | mRNA | 258 |
| BDNF | Protein | 259 |
| CACNA1G | mRNA Sequence for alpha 1G subunit (isoform 1) | 260 |

-continued

| Gene | Sequence Type | SEQ ID NO |
|---|---|---|
| CACNA1G | Protein sequence for alpha 1G subunit (isoform 1) | 261 |
| CACNA1G | mRNA Sequence for alpha 1G subunit (isoform 2) | 262 |
| CACNA1G | Protein Sequence for alpha 1G subunit (isoform 2) | 263 |
| CACNA1G | mRNA Sequence for alpha 1G subunit (isoform 3) | 264 |
| CACNA1G | Protein Sequence for alpha 1G subunit (isoform 3) | 265 |
| CACNA1G | mRNA Sequence for alpha 1G subunit (isoform 4) | 266 |
| CACNA1G | Protein Sequence for alpha 1G subunit (isoform 4) | 267 |
| CACNA1G | mRNA Sequence for alpha 1G subunit (isoform 5) | 268 |
| CACNA1G | Protein Sequence for alpha 1G subunit (isoform 5) | 269 |
| CACNA1G | mRNA Sequence for alpha 1G subunit (isoform 6) | 270 |
| CACNA1G | Protein Sequence for alpha 1G subunit (isoform 6) | 271 |
| CACNA1G | mRNA Sequence for alpha 1G subunit (isoform 7) | 272 |
| CACNA1G | Protein Sequence for alpha 1G subunit (isoform 7) | 237 |
| CACNA1G | mRNA Sequence for alpha 1G subunit (isoform 8) | 274 |
| CACNA1G | Protein Sequence for alpha 1G subunit (isoform 8) | 275 |
| CACNA1G | mRNA Sequence for alpha 1G subunit (isoform 9) | 276 |
| CACNA1G | Protein Sequence for alpha 1G subunit (isoform 9) | 277 |
| CACNA1G | mRNA Sequence for alpha 1G subunit (isoform 10) | 278 |
| CACNA1G | Protein Sequence for alpha 1G subunit (isoform 10) | 279 |
| CACNA1G | mRNA Sequence for alpha 1G subunit (isoform 11) | 280 |
| CACNA1G | Protein Sequence for alpha 1G subunit (isoform 11) | 281 |
| CACNA1G | mRNA Sequence for alpha 1G subunit (isoform 12) | 282 |
| CACNA1G | Protein Sequence for alpha 1G subunit (isoform 12) | 283 |
| CACNA1G | mRNA Sequence for alpha 1G subunit (isoform 13) | 284 |
| CACNA1G | Protein Sequence for alpha 1G subunit (isoform 13) | 285 |
| CACNA1G | mRNA Sequence for alpha 1G subunit (isoform 14) | 286 |
| CACNA1G | Protein Sequence for alpha 1G subunit (isoform 14) | 287 |
| CACNA1G | mRNA Sequence for alpha 1G subunit (isoform 15) | 288 |
| CACNA1G | Protein Sequence for alpha 1G subunit (isoform 15) | 289 |
| CALCA | Transcript variant 1 mRNA | 290 |
| CALCA | Transcript variant 1 protein | 291 |
| CALCA | Transcript variant 2 mRNA | 292 |
| CALCA | Transcript variant 2 protein | 293 |
| CALCA | Transcript variant 3 mRNA | 294 |
| CALCA | Transcript variant 3 protein | 295 |
| CRABP1 | mRNA | 296 |
| CRABP1 | protein | 297 |
| DLEC1 | Transcript variant DLEC1-N1 mRNA | 298 |
| DLEC1 | Transcript variant DLEC1-N1 protein | 299 |
| GATA3 | Isoform 1 mRNA | 300 |
| GATA3 | Isoform 1 protein | 301 |
| GATA3 | Isoform 2 mRNA | 302 |
| GATA3 | Isoform 2 protein | 303 |
| HOXA1 | Transcript variant 1 mRNA | 304 |
| HOXA1 | Transcript variant 1 protein | 305 |
| HOXA1 | Transcript variant 2 mRNA | 306 |
| HOXA1 | Transcript variant 2 protein | 307 |
| IGF2 | mRNA | 308 |
| IGF2 | protein | 309 |

125
-continued

| Gene | Sequence Type | SEQ ID NO |
|---|---|---|
| KL | Transcript variant 1 mRNA | 310 |
| KL | Transcript variant 1 protein | 311 |
| KL | Transcript variant 2 mRNA | 312 |
| KL | Transcript variant 2 protein | 313 |
| NEUROG1 | mRNA | 314 |
| NEUROG1 | protein | 315 |
| NR3C1 | Transcript variant 1 mRNA | 316 |
| NR3C1 | Transcript variant 1 protein | 317 |
| NR3C1 | Transcript variant 2 mRNA | 318 |
| NR3C1 | Transcript variant 2 protein | 319 |
| NR3C1 | Transcript variant 3 mRNA | 320 |
| NR3C1 | Transcript variant 3 protein | 321 |
| NR3C1 | Transcript variant 4 mRNA | 322 |
| NR3C1 | Transcript variant 4 protein | 323 |

126
-continued

| Gene | Sequence Type | SEQ ID NO |
|---|---|---|
| NR3C1 | Transcript variant 5 mRNA | 324 |
| NR3C1 | Transcript variant 5 protein | 325 |
| NR3C1 | Transcript variant 6 mRNA | 326 |
| NR3C1 | Transcript variant 6 protein | 327 |
| NR3C1 | Transcript variant 7 mRNA | 328 |
| NR3C1 | Transcript variant 7 protein | 329 |
| RUNX1 | Isoform 1 mRNA | 330 |
| RUNX1 | Isoform 1 protein | 331 |
| RUNX1 | Isoform 2 mRNA | 332 |
| RUNX1 | Isoform 2 protein | 333 |
| SOCS1 | mRNA | 334 |
| SOCS1 | protein | 335 |

Amplicon Table

| HUGO Gene Name | Amplicon Sequence | Accession No. | Amplicon Location | Amplicon Length |
|---|---|---|---|---|
| BCL2 | CCGCATCCCGGGACCCGGTC GCCAGGACCTCGCCGCTGCA GACCCCGGCTGCCCCCGGCG CCGCCGCGGGGCCTGCGCTC AGCC (SEQ ID NO: 100) | Widschwendter, M. et al Cancer Res 64, 3807-3813 (2004); GenBank Number NM00633 | 672-755 (in GenBank entry) | 82 |
| BDNF | CGCACCGGGCTGGCTCCTCT GTCCGGCCCGGGAGCCCGAG GCGCTACGGGGTGCGCGGGA CAGCGAGCGGGCG (SEQ ID NO: 101) | GenBank Number AC103796 | 3794-3866 | 72 |
| CACNA1G | CTTCTTCGCTTCGCGCCCAG GCTCCGGTTGCCGGATTCGG CGCTACCTTCGGCGAAGCCG CCCCGAG (SEQ ID NO: 102) | GenBank Number AC021491 | 48345-48411 | 66 |
| CALCA | GTTCTGGAAGCATGAGGGTG ACGCAACCCAGGGGCAAAGG ACCCCTCCGCCCATTGGTTG CTGTGCACTGGCGGAACTTT CCCGACCCACAGCGGCGGGA A (SEQ ID NO: 103) | GenBank Number X15943 | 1706-1806 | 100 |
| CRABP1 | TCGAAATTCTCGCTGCTGCG CATCTTCCAGGTGCCGGCGA AGTTGGGCATGGTGGCGGTG GCGGCGGCGGCAGGTACGGA CA (SEQ ID NO: 104) | GenBank Number AC011270 | 122142-122223 | 81 |
| DLEC1 | TCGCTGCGCACCCAAGATAT CTCGCACTTGCTCACCGGCG TCTTCCGCAACTTGTACTCA GCCGAGGTCATCGGCGACGA AGTGAGCGCAAGCTTGATCA AGGCCCGCGGCAGCGAGAAT GAGCGCCACG (SEQ ID NO: 105) | GenBank Number AP006309 | 19959-20088 | 129 |
| GATA3 | TGCACCGGGACGGAATCGTC CACCCGACCCGAATGAATTG GCAGGAGCCGCGGCCACATT TAAAGGGCCAGAGCGCGCGT (SEQ ID NO: 106) | GenBank Number AL390294 | 51880-51959 | 79 |
| HOXA1 | CTGCCCACTAGGAAGCGGTC GTCGCCGCCGCAACTGTTGG CGCTGACCGCGCACGACTGG AAAGTTGTAATCCTATGGTC CGA (SEQ ID NO: 107) | GenBank Number AC004079 | 78138-78220 | 82 |

-continued

Amplicon Table

| HUGO Gene Name | Amplicon Sequence | Accession No. | Amplicon Location | Amplicon Length |
|---|---|---|---|---|
| IGF2 | GAGCGGCCCCGGTGCCGCCACCGCCTGTCCCCCTCCCGAGGCCCGGGCTCGCGACGGCAGAGGGCTCCGTCGGCCCAAACCGAGCTGG (SEQ ID NO: 108) | GenBank Number AC132217 | 108633-108720 | 87 |
| KL | AGCCTGGCTCCCGCGCAGCATGCCCGCCAGCGCCCCGCCGCGCCGCCCGCGGCCGCCGCCGCAGTCGCTGTCGCTGCTGCTGGTGCTGCTGGGCCTGGGCGGCCGCCGCCTGCGTGCGGAGCCGGGCG (SEQ ID NO: 109) | GenBank Number AB009667 | 2062-2189 | 127 |
| NEUROG1 | CGTGCAGCGCCCGGGTATTTGCATAATTTATGCTCGCGGGAGGCCGCCATCGCCCCTCCCCCAACCCGGAGTGTGCCCGTAATTACCG (SEQ ID NO: 110) | GenBank Number AC005738 | 75342-75429 | 87 |
| NR3C1 | GGGTGGAAGGAGACGCCGCAGCCGGAGCGGCCGAAGCAGCTGGGACCGGGACGGGGCACGCGCGCCCGGAAGCCC (SEQ ID NO: 111) | GenBank Number AY436590 | 1786-1861 | 75 |
| RUNX3 | GACGGGCAGCGTCTTGTTGCAGCGCCAGTGCGAGGGCAGCACGGAGCAGAGGAAGTTGGGGCTGTCGGTGCGCACGAGCTCGCCTGCGTGGTCCGCCAGCACGTCCACCATCGAGCG (SEQ ID NO: 112) | GenBank Number AL023096 | 64646-64762 | 116 |
| SOCS1 | CGAGCCCGTGGGCACCTTCCTGGTGCGCGACAGCCGCCAGCGGAACTGCTTTTTCGCCCTTAGCGTGAAGATGGCCTCGG (SEQ ID NO: 113) | Fiegl, H. et al Cancer Epidemiol Biomarkers Prey 13,882-888 (2004); GenBank Number DQ086801 | 2808-2887 | 79 |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08110361B2). An electronic copy of the "Sequence Listing" will also be available from the USPTO upon request and payment of the fee set forth in 37 CFR 1.19(b)(3).

The invention claimed is:

1. A method for detecting and/or classifying a colorectal cancer belonging to a distinct colorectal cancer subgroup having frequent CpG island hypermethylation (CIMP colorectal cancer), comprising:
determining, by analyzing a human subject biological sample comprising colon cancer cell genomic DNA, a CpG methylation status of at least one gene or genomic sequence selected from the NEUROG1 sequence group consisting of NEUROG1, SEQ ID NOS:138, 124 and 110, wherein CpG hypermethylation, relative to normal controls, is indicative of a colorectal cancer belonging to a distinct colorectal cancer subgroup having frequent CpG island hypermethylation (CIMP colorectal cancer), wherein a method for detecting and/or classifying a CIMP colorectal cancer is afforded.

2. The method of claim 1, wherein CIMP colorectal cancer is distinguished from a colorectal cancer subgroup not having frequent CpG island hypermethylation (non-CIMP colorectal cancer), said method characterized in that the presence of CpG hypermethylation, relative to normal controls, is indicative of CIMP colorectal cancer and the absence or relative absence thereof, relative to normal controls, is indicative of non-CIMP colorectal cancer.

3. The method of claim 1, wherein the CIMP colorectal cancer comprises a cell proliferative condition and/or cancer.

4. The method of claim 3, wherein the CIMP colorectal cancer comprises colorectal carcinoma.

5. The method of claim 1, comprising: contacting genomic DNA isolated from a biological sample obtained from a subject with at least one reagent, or series of reagents that distinguishes between methylated and non-methylated CpG dinucleotides within at least one target region of the genomic DNA, wherein the at least one target region comprises, or hybridizes under stringent conditions to a sequence of at least 16 contiguous nucleotides of at least one sequence selected from the NEUROG1 sequence group consisting of NEUROG1, SEQ ID NOS:138, 124 and 110, wherein said contiguous nucleotides comprise at least one CpG dinucleotide sequence.

6. The method of claim 1, comprising:
obtaining genomic DNA from a biological sample obtained from a subject;
treating the genomic DNA, or at least one fragment thereof, with one or more reagents to convert cytosine bases that are unmethylated in the 5-position thereof to uracil or to another base that is detectably dissimilar to cytosine in terms of hybridization properties;
contacting the treated genomic DNA, or the at least one treated fragment thereof, with an amplification enzyme and at least one primer comprising, a contiguous sequence of at least 9 nucleotides that is complementary to, or hybridizes under moderately stringent or stringent conditions to at least one sequence selected from the NEUROG1 sequence group consisting of NEUROG1, SEQ ID NOS:138, 124 110, 190, 191, 246, 247, 162, 163, 218, 219, and complements thereof, wherein the treated genomic DNA or the at least one fragment thereof is either amplified to produce at least one amplificate, or is not amplified; and
determining, based on a presence or absence of, or on a property of said amplificate, the methylation state or level of at least one CpG dinucleotide, or a value based on an average methylation state or level of a plurality of CpG dinucleotides, of a sequence selected from the NEUROG1 sequence group consisting of NEUROG1, SEQ ID NOS:138, 124 and 110.

7. The method of any one of claims 5 and 6, wherein contacting or treating the genomic DNA, or the fragment thereof, comprises use of a reagent selected from the group consisting of bisulfite, hydrogen sulfite, disulfite, and combinations thereof.

8. The method of claim 5, further comprising contacting the genomic DNA with at least one reagent, or series of reagents that distinguishes between methylated and non-methylated CpG dinucleotides within additional target regions of the genomic DNA, wherein the additionally target regions comprise, or hybridize under stringent conditions to a sequence of at least 16 contiguous nucleotides of at least one sequence selected from each gene sequence group of the combination of gene sequence groups consisting of: CACNA1G sequence group of CACNA1G, SEQ ID NOS: 130, 116 and 102; IGF2 sequence group of IGF2, SEQ ID NOS:136, 122 and 108; RUNX3 sequence group of RUNX3, SEQ ID NOS:140, 126 and 112; and SOCS1 sequence group of SOCS1, SEQ ID NOS:141, 127 and 113, wherein said contiguous nucleotides comprise at least one CpG dinucleotide sequence.

9. The method of claim 8, comprising determining a CpG methylation status of a gene or genomic sequence combination selected from the combination group consisting of:
NEUROG1, CACNA1G, IGF2, RUNX3 and SOCS1;
SEQ ID NOS:138, 130, 136, 140 and 141;
SEQ ID NOS:124, 116, 122, 126 and 127; and
SEQ ID NOS:110, 102, 108, 112 and 113.

10. The method of claim 6, wherein contacting or amplifying comprises: use of at least one method selected from the group consisting of: use of a heat-resistant DNA polymerase as the amplification enzyme; use of a polymerase lacking 5'-3' exonuclease activity; use of a polymerase chain reaction (PCR); and generation of an amplificate nucleic acid molecule carrying a detectable label.

11. The method of claim 6, further comprising, for determining, the use of at least one nucleic acid molecule or peptide nucleic acid molecule comprising in each case a contiguous sequence at least 9 nucleotides in length that is complementary to, or hybridizes under moderately stringent or stringent conditions to a sequence selected from the NEUROG1 sequence group consisting of SEQ ID NOS:190, 191, 246, 247, 162, 163, 218, 219, and complements thereof, wherein said nucleic acid molecule or peptide nucleic acid molecule suppresses amplification of the nucleic acid to which it is hybridized.

12. The method of claim 11, further comprising, for determining, the use of at least one nucleic acid molecule or peptide nucleic acid molecule comprising in each case a contiguous sequence at least 9 nucleotides in length that is complementary to, or hybridizes under moderately stringent or stringent conditions to at least one sequence selected from each gene sequence group of the combination of gene sequence groups consisting of: CACNA1G sequence group of SEQ ID NOS:174, 175, 230, 231, 146, 147, 202, 203 and complements thereof; IGF2 sequence group of SEQ ID NOS: 186, 187, 242, 243, 158, 159, 214. 215 and complements thereof; RUNX3 sequence group of SEQ ID NOS:194, 195, 250, 251, 166, 167, 222, 223 and complements thereof; and SOCS1 sequence group of SEQ ID NOS:196, 197, 252, 253, 168, 169, 224, 225 and complements thereof, wherein said nucleic acid molecule or peptide nucleic acid molecule suppresses amplification of the nucleic acid to which it is hybridized.

13. The method of claim 6, wherein determining comprises hybridization of at least one nucleic acid molecule or peptide nucleic acid molecule in each case comprising a contiguous sequence at least 9 nucleotides in length that is complementary to, or hybridizes under moderately stringent or stringent conditions to a sequence selected from the NEUROG1 sequence group consisting of SEQ ID NOS:190, 191, 246, 247, 162, 163, 218, 219, and complements thereof.

14. The method of claim 13, wherein at least one such hybridizing nucleic acid molecule or peptide nucleic acid molecule is bound to a solid phase.

15. The method of claim 13, further comprising extending at least one such hybridized nucleic acid molecule by at least one nucleotide base.

16. The method of claim 13, wherein determining further comprises hybridization of at least one nucleic acid molecule or peptide nucleic acid molecule in each case comprising a contiguous sequence at least 9 nucleotides in length that is complementary to, or hybridizes under moderately stringent or stringent conditions to at least one sequence selected from each gene sequence group of the combination of gene sequence groups consisting of: CACNA1G sequence group of SEQ ID NOS:174, 175, 230, 231, 146, 147, 202, 203 and complements thereof; IGF2 sequence group of SEQ ID NOS: 186, 187, 242, 243, 158, 159, 214. 215 and complements thereof; RUNX3 sequence group of SEQ ID NOS:194, 195, 250, 251, 166, 167, 222, 223 and complements thereof; and SOCS1 sequence group of SEQ ID NOS:196, 197, 252, 253, 168, 169, 224, 225 and complements thereof.

17. The method of claim 6, wherein determining in comprises sequencing of the amplificate.

18. The method of claim 6, wherein contacting or amplifying comprises use of methylation-specific primers.

19. The method of claim 6, further comprising contacting the treated genomic DNA, or the at least one treated fragment thereof, with an amplification enzyme and at least one primer comprising, a contiguous sequence of at least 9 nucleotides that is complementary to, or hybridizes under moderately stringent or stringent conditions to at least one sequence selected from each gene sequence group of the combination of gene sequence groups consisting of: CACNA1G sequence group of CACNA1G, SEQ ID NOS:130, 116, 102, 174, 175, 230, 231, 146, 147, 202, 203, and complements thereof; IGF2 sequence group of IGF2, SEQ ID NOS:136, 122, 108, 186, 187, 242, 243, 158, 159, 214. 215, and complements thereof; RUNX3 sequence group of RUNX3, SEQ ID NOS:140, 126, 112, 194. 195, 250, 251, 166, 167, 222, 223, and complements thereof; and SOCS1 sequence group of SOCS1, SEQ ID NOS:141, 127, 113, 196, 197, 252, 253, 168, 169, 224, 225, and complements thereof, wherein the treated genomic DNA or the at least one fragment thereof is either amplified to produce at least one amplificate, or is not amplified; and
    determining, based on a presence or absence of, or on a property of said amplificate, the methylation state or level of at least one CpG dinucleotide, or a value based on an average methylation state or level of a plurality of CpG dinucleotides, of at least one sequence selected from each gene sequence group of the combination of gene sequence groups consisting of NEUROG1 sequence group of NEUROG1, SEQ ID NOS:138, 124 and 110, CACNA1G sequence group of CACNA1G, SEQ ID NOS:130, 116 and 102, IGF2 sequence group of IGF2, SEQ ID NOS:136, 122 and 108, RUNX3 sequence group of RUNX3, SEQ ID NOS:140, 126 and 112, and SOCS1 sequence group of SOCS1, SEQ ID NOS:141, 127 and 113.

20. The method of claim 1, wherein the human subject biological sample is selected from the group consisting of cell lines, histological slides, biopsies, paraffin-embedded tissue, body fluids, stool, colonic effluent, urine, blood plasma, blood serum, whole blood, isolated blood cells, cells isolated from the blood, and combinations thereof.

21. The method of claim 1, wherein CIMP KRAS mutant, BRAF wildtype tumors colorectal cancer is identified or distinguished.

22. The method of claim 1, further comprising relating CIMP status to at least one selected from the group consisting of age, sex, tumor location, family history, race, country of origin, and tumor characteristics including, tumor type, tumor grade, invasive margin characteristics, lymphocyte infiltration characteristics, direct spread, lymph node spread, venous spread and type of residual adjacent polyp, if present.

23. The method of claim 1, wherein detecting and/or classifying a colorectal cancer belonging to a distinct colorectal cancer subgroup having frequent CpG island hypermethylation (CIMP colorectal cancer), comprises determining, between subgroups defined by CIMP status and BRAF mutations, effects of selected risk factors including, but not limited to body mass index, smoking history, alcohol intake, dietary folate intake, folate metabolic enzyme polymorphisms and history of hormonal use.

24. The method of claim 1, further comprising determining a CpG methylation status of at least one sequence selected from each gene sequence group of the combination of gene sequence groups consisting of: CACNA1G sequence group of CACNA1G, SEQ ID NOS:130, 116 and 102; IGF2 sequence group of IGF2, SEQ ID NOS:136, 122 and 108; RUNX3 sequence group of RUNX3, SEQ ID NOS:140, 126 and 112; and SOCS1 sequence group of SOCS1, SEQ ID NOS:141, 127 and 113, wherein CpG hypermethylation, relative to normal controls, is indicative of a colorectal cancer belonging to a distinct colorectal cancer subgroup having frequent CpG island hypermethylation (CIMP colorectal cancer).

25. The method of claim 24, comprising determining a CpG methylation status of a gene or genomic sequence combination selected from the combination group consisting of:
    NEUROG1, CACNA1G, IGF2, RUNX3 and SOCS1;
    SEQ ID NOS:138, 130, 136, 140 and 141;
    SEQ ID NOS:124, 116, 122, 126 and 127; and
    SEQ ID NOS:110, 102, 108, 112 and 113.

26. A method for detecting and/or classifying a colorectal cancer belonging to a distinct colorectal cancer subgroup having frequent CpG island hypermethylation (CIMP colorectal cancer), comprising:
    digesting genomic DNA obtained from a human subject biological sample comprising colon cancer cell genomic DNA, or a fragment thereof, with one or more methylation sensitive restriction enzymes;
    contacting the DNA restriction enzyme digest with an amplification enzyme and at least two primers suitable for the amplification of a sequence comprising at least one CpG dinucleotide of a sequence selected from the NEUROG1 sequence group consisting of NEUROG1, SEQ ID NOS:138, 124 and 110; and
    determining, based on a presence or absence of an amplificate the methylation state or level of at least one CpG dinucleotide of at least one gene or genomic sequence selected from the NEUROG1 sequence group consisting of NEUROG1, SEQ ID NOS:138, 124 and 110, wherein CpG hypermethylation, relative to normal controls, is indicative of a colorectal cancer belonging to a distinct colorectal cancer subgroup having frequent CpG island hypermethylation (CIMP colorectal cancer), wherein a method for detecting and/or classifying a CIMP colorectal cancer is afforded.

27. The method of claim 26, wherein the presence or absence of an amplificate is determined by means of hybridization to at least one nucleic acid or peptide nucleic acid which is identical, complementary, or hybridizes under stringent or highly stringent conditions to an at least 16 base long contiguous segment of at least one sequence selected from the NEUROG1 sequence group consisting of NEUROG1, SEQ ID NOS:138, 124 and 110.

28. The method of claim 27, wherein the presence or absence of an amplificate is determined by means of hybridization to at least one nucleic acid or peptide nucleic acid which is identical, complementary, or hybridizes under stringent or highly stringent conditions to an at least 16 base long contiguous segment of at least one sequence selected from each gene sequence group of the combination of gene sequence groups consisting of NEUROG1 sequence group of NEUROG1, SEQ ID NOS:138, 124 and 110, CACNA1G sequence group of CACNA1G, SEQ ID NOS:130, 116 and 102, IGF2 sequence group of IGF2, SEQ ID NOS:136, 122 and 108, RUNX3 sequence group of RUNX3, SEQ ID NOS: 140, 126 and 112, and SOCS1 sequence group of SOCS1, SEQ ID NOS:141, 127 and 113.

29. The method of claim 26, further comprising contacting the DNA restriction enzyme digest with an amplification enzyme and at least two primers suitable for the amplification of at least one sequence selected from each gene sequence group of the combination of gene sequence groups consisting of: CACNA1G sequence group of CACNA1G, SEQ ID NOS: 130, 116 and 102; IGF2 sequence group of IGF2, SEQ ID NOS:136, 122 and 108; RUNX3 sequence group of RUNX3, SEQ ID NOS:140, 126 and 112; and SOCS1 sequence group of SOCS1, SEQ ID NOS:141, 127 and 113; and determining, based on a presence or absence of an amplificate, the methylation state or level of at least one sequence selected from each gene sequence group of the combination of gene sequence groups consisting of NEUROG1 sequence group of NEUROG1, SEQ ID NOS:138, 124 and 110, CACNA1G sequence group of CACNA1G, SEQ ID NOS:130, 116 and 102, IGF2 sequence group of IGF2, SEQ ID NOS:136, 122 and 108, RUNX3 sequence group of RUNX3, SEQ ID NOS: 140, 126 and 112, and SOCS1 sequence group of SOCS1, SEQ ID NOS:141, 127 and 113.

\* \* \* \* \*